US009850309B2

(12) United States Patent
Shibuya et al.

(10) Patent No.: US 9,850,309 B2
(45) Date of Patent: *Dec. 26, 2017

(54) MEDICAMENT COMPRISING ACTIVITY MODULATOR FOR CD300A-EXPRESSING CELL ASSOCIATED WITH ALLERGIC DISEASE, CD300A GENE-DEFICIENT MOUSE, AND USE OF ACTIVITY MODULATOR FOR CD300A-EXPRESSING CELL

(71) Applicant: UNIVERSITY OF TSUKUBA, Tsukuba-shi, Ibaraki (JP)

(72) Inventors: Akira Shibuya, Tsukuba (JP); Chigusa Oda, Tsukuba (JP); Udayanga Sanath Kankanam Gamage, Tsukuba (JP); Haruka Miki, Tsukuba (JP)

(73) Assignee: UNIVERSITY OF TSUKUBA, Tsukuba-shi (JP)

( * ) Notice: Subject to any disclaimer, the term of this patent is extended or adjusted under 35 U.S.C. 154(b) by 54 days.

This patent is subject to a terminal disclaimer.

(21) Appl. No.: 14/441,109

(22) PCT Filed: Nov. 5, 2013

(86) PCT No.: PCT/JP2013/079890
§ 371 (c)(1),
(2) Date: May 6, 2015

(87) PCT Pub. No.: WO2014/073529
PCT Pub. Date: May 15, 2014

(65) Prior Publication Data
US 2015/0299332 A1   Oct. 22, 2015

(30) Foreign Application Priority Data

Nov. 7, 2012  (JP) ................................. 2012-245816

(51) Int. Cl.

| | |
|---|---|
| *C07K 16/28* | (2006.01) |
| *A61K 39/395* | (2006.01) |
| *G01N 33/50* | (2006.01) |
| *A61K 38/17* | (2006.01) |
| *A61K 38/39* | (2006.01) |
| *A61K 45/06* | (2006.01) |
| *A01K 67/027* | (2006.01) |
| *C07K 14/705* | (2006.01) |
| *A61K 31/00* | (2006.01) |

(52) U.S. Cl.
CPC ...... *C07K 16/2896* (2013.01); *A01K 67/0276* (2013.01); *A61K 31/00* (2013.01); *A61K 38/177* (2013.01); *A61K 38/39* (2013.01); *A61K 45/06* (2013.01); *C07K 14/70503* (2013.01); *C07K 14/70596* (2013.01); *C07K 16/2803* (2013.01); *G01N 33/5023* (2013.01); *G01N 33/5088* (2013.01); *A01K 2217/075* (2013.01); *A01K 2227/105* (2013.01); *A01K 2267/0387* (2013.01); *G01N 2333/70596* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 7,741,271 B2 * | 6/2010 | Kuchroo | A61K 38/177 424/278.1 |
| 2005/0261224 A1 | 11/2005 | Kuchroo et al. | |
| 2006/0121484 A1 | 6/2006 | Kitamura et al. | |
| 2008/0219980 A1 | 9/2008 | Levi-Schaffer et al. | |
| 2009/0035314 A1 | 2/2009 | Kim et al. | |
| 2010/0041762 A1 | 2/2010 | Bohnert et al. | |
| 2011/0152169 A1 | 6/2011 | Motamed et al. | |
| 2015/0047059 A1 * | 2/2015 | Shibuya | A61K 38/16 800/3 |

FOREIGN PATENT DOCUMENTS

| | | |
|---|---|---|
| AU | 2007201759 A1 | 5/2007 |
| JP | 2004-173531 A | 6/2004 |
| JP | 2007-297379 A | 11/2007 |

(Continued)

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
McIntire J.J. et al.: "TIM-1, a novel allergy and asthma susceptibility gene", Springer Seminar in Immunopathology, Springer Verlag, DE, vol. 25, Feb. 1, 2004, pp. 335-348.
Extended (supplementary) European Search Report dated May 19, 2016, issued in European Patent Application No. 13852528.2. (12 pages).
International Search Report dated Dec. 24, 2013 issued in corresponding application No. PCT/JP2013/079890.

(Continued)

*Primary Examiner* — Hong Sang
(74) *Attorney, Agent, or Firm* — Westerman, Hattori, Daniels & Adrian

(57) ABSTRACT

The present invention provides medicaments for allergic diseases (atopic dermatitis, asthma, and the like), and a tool useful for pathology analysis of allergic diseases. A medicament containing as an effective component an activity modulator for suppressing inhibitory signal transduction of a CD300a-expressing myeloid cell, which activity modulator contains a substance that inhibits binding of CD300a to phosphatidyl serine, can be used for treatment or prophylaxis of an allergic disease. A CD300a gene-deficient mouse can be used as a model mouse in which the allergic disease is hardly induced after administration of a substance that induces the allergic disease, which may be used for carrying out pathology analysis of an allergic disease, or for screening of a possible candidate substance for an effective component of a therapeutic agent or prophylactic agent for the disease.

4 Claims, 55 Drawing Sheets

(56) References Cited

FOREIGN PATENT DOCUMENTS

| | | |
|---|---|---|
| JP | 2011-516609 A | 5/2011 |
| KR | 2012-0100468 A | 9/2012 |
| WO | 2004/039981 A1 | 5/2004 |
| WO | 2004/048574 A1 | 6/2004 |
| WO | 2005/090573 A2 | 9/2005 |
| WO | 2005095460 A2 | 10/2005 |
| WO | 2006080756 A1 | 8/2006 |
| WO | 2006/122327 A2 | 11/2006 |
| WO | 2007101254 A2 | 9/2007 |
| WO | 2008064031 A2 | 5/2008 |
| WO | 2008/103310 A1 | 8/2008 |
| WO | 2008/133851 A1 | 11/2008 |
| WO | 2013/077186 A1 | 5/2013 |
| WO | WO2013077186 A1 * | 5/2013 |

OTHER PUBLICATIONS

Chae et al., "The association of the exon 4 variations of Tim-1 gene with allergic diseases in a Korean population", Biochemical Biophysical Research Communications, vol. 312, No. 2, 2003, pp. 346-350.

Umetsu et al., "99th Dahlem Conference on Infection, Inflammation and Chronic Inflammatory Disorders: Microbes, apoptosis and TIM-1 in the development of asthma", Clinical and Expertimental Immunology, vol. 160, No. 1, 2010, pp. 125-129.

Atabai et al., "Mfge8 Regulates Airway Smooth Muscle Contraction in Allergic Airway Disease in Mice", American Journal of Respiratory and Critical Care Medicine, vol. 183, No. 1, May 1, 2011, Supplemental Meeting Abstracts A3594; 1 page.

Kobayashi et al., "TIM-1 and TIM-4 Glycoproteins Bind Phosphatidylserine and Mediate Uptake of Apoptotic Cells", Immunity, vol. 27, No. 6, Dec. 2007, pp. 927-940.

Park et al., "Rapid cell corpse clearance by stabilin-2, a membrane phosphatidylserine receptor", Cell Death and Differentiation, vol. 15, No. 1, 2008, pp. 192-201.

Nakahashi-Oda et al., "Identification of phosphatidylserine as a ligand for the CD300a immunoreceptor", Biochemical Biophysical Research Commununications, vol. 417, No. 1, 2012, pp. 646-650.

Oda (Nakahashi) et al., "Activation of Mast Cells by Myeloid-associated Ig like receptor-I (MAIR-I)", Clinical Immunology & Allergology, vol. 54, No. 2, 2010, pp. 142-148; w/ English Translation.

Nunomura et al., "Na-Tosyl-Phe chloromethyl ketone prevents granule movement and mast cell synergistic degranulation elicited by costimulation of antigen and adenosine", Life Sciences, vol. 83, 2008, pp. 242-249.

Kudo et al., "Mfge8 suppresses airway hyperresponsiveness in asthma by regulating smooth muscle contraction", Proceedings of the National Academy of Sciences of the United States of America, vol. 110, No. 2, Jan. 8, 2013, pp. 660-665; Epub Dec. 26, 2012.

Nakahashi-Oda et al., "Apoptotic cells suppress mast cell inflammatory responses via the CD300a immunoreceptor", The Journal of Experimental Medicine, vol. 209, No. 8, Jul. 23, 2012, pp. 1493-1503.

Simhadri et al., "Human CD300a binds to phosphatidylethanolamine and phosphatidylserine, and modulates the phagocytosis of dead cells", Immunobiology, vol. 119, No. 12, Mar. 22, 2012, pp. 2799-2809.

Yotsumoto et al., "Paired Activating and Inhibitory Immunoglobulin-like Receptors, MAIR-I and MAIR-II, Regulate Mast Cell and Macrophage Activation", The Journal of Experimental Medicine, vol. 198, No. 2, Jul. 21, 2003, pp. 223-233.

Okoshi et al., "Requirement of the tyrosines at residues 258 and 270 of MAIR-I in inhibitory effect on degranulation from basophilic leukemia RBL-2H3", International Immunology, vol. 17, No. 1, Nov. 29, 2004, pp. 65-72.

Masuoka et al., "Periostin promotes chronic allergic inflammation in response to Th2 cytokines", The Journal of Clinical Investigation, vol. 122, No. 7, Jul. 2012, pp. 2590-2600.

Kumagai et al., "Identification and characterization of a new pair of immunoglobulin-like receptors LMIR1 and 2 derived from murine bone marrow-derived mast cells", Biochemical and Biophysical Research Communications, vol. 307, Aug. 1, 2003, pp. 719-729.

Chung et al., "CMRF-35-Like Molecule-1, a Novel Mouse Myeloid Receptor, Can Inhibit Osteoclast Formation", The Journal of Immunology, vol. 171, Dec. 15, 2003, pp. 6541-6548.

Hanayama et al., "Identification of a factor that links apoptotic cells to phagocytes", Nature, vol. 417, May 9, 2002, pp. 182-187.

Miyanishi et al., "Identification of Tim4 as a phosphatidylserine receptor", Nature, vol. 450, Nov. 15, 2007, pp. 435-439.

Kobayashi et al., "T cell Immunoglobulin Mucin Protein (TIM)-4 binds phosphatidylserine and mediates uptake of apoptotic cells", Immunity, vol. 27, No. 2, Dec. 2007, pp. 927-940.

Park et al., "Rapid cell corpse clearance by stabilin-2, a membrane phosphatidylserine receptor", Cell Death and Differentiation, vol. 15, Jan. 2008, pp. 192-201.

Park et al., "Ba11 is an engulfment receptor for apoptotic cells upstream of the ELMO/Dock180/Rac module", Nature, vol. 450, Nov. 15, 2007, pp. 430-435.

Scott et al., "Phagocytosis and clearance of apoptotic cells is mediated by MER", Nature, vol. 411, May 10, 2001, pp. 207-211.

Fadok et al., "Exposure of Phosphatidylserine on the Surface of Apoptotic Lymphocytes Triggers Specific Recognition and Removal by Macrophages", The Journal of Immunology, vol. 148, No. 7, Apr. 1, 1992, pp. 2207-2216.

Savill et al., "A Blast From the Past: Clearance of Apoptotic Cells Regulates Immune Responses", Immunology, vol. 2, Dec. 2002, pp. 965-975.

Nagata, "DNA Degradation in Development and Programmed Cell Death", Annual Review of Immunology, vol. 23, 2005, pp. 853-875.

Kuchroo et al., "New roles for TIM family members in immune regulation", Immunology, vol. 8, Aug. 2008, pp. 577-580.

Marshall, "Mast-Cell Responses to Pathogens", Immunology, vol. 4, Oct. 2004, pp. 787-799.

Echtenacher et al., "Critical protective role of mast cells in a model of acute septic peritonitis", Nature, vol. 381, May 2, 1996, pp. 75-77.

Malaviya et al., "Mast cell modulation of neutrophil influx and bacterial clearance at sites of infection through TNF-alpha", Nature, vol. 381, May 2, 1996, pp. 77-80.

Matsukawa et al., "Endogenous Monocyte Chemoattractant Protein-1 (MCP-1) Protects Mice in a Model of Acute Septic Peritonitis: Cross-Talk Between MCP-1 and Leukotriene B4", The Journal of Immunology, vol. 163, 1999, pp. 6148-6154.

Baumhofer et al., "Gene transfer with IL-4 and IL-13 improves survival in lethal endotoxemia in the mouse and ameliorates peritoneal macrophages immune competence", Eur. J. Immunol., vol. 28, 1998, pp. 610-615.

Hotchkiss et al., "Apoptosis and caspases regulate death and inflammation in sepsis", Immunology, vol. 6, Nov. 2006, pp. 813-822.

Grimbaldeston et al., "Mast Cell-Deficient W-sash c-kit Mutant KitW-sh/W-sh Mice as a Model for Investigating Mast Cell Biology in Vivo" American Journal of Pathology, vol. 167, No. 3, Sep. 2005, pp. 835-848.

Hanayama et al., "Autoimmune Disease and Impaired Uptake of Apoptotic Cells in MFG-E8-Deficient Mice", Science, vol. 304, 1147, May 21, 2004, pp. 1147-1150.

Bischoff, "Role of mast cells in allergic and non-allergic immune responses: comparison of human and murine data", Immunology, vol. 7, Feb. 2007, pp. 93-104.

Abraham et al., "Mast cell-orchestrated immunity to pathogens", Immunology, vol. 10, Jun. 2010, pp. 440-452.

Tahara-Hananoka et al., "Functional characterization of DNAM-1 (CD226) interaction with its ligands PVR (CD155) and nectin-2 (PRR-2/CD112)", International Immunology, vol. 16, No. 4, 2004, pp. 533-538.

Plitas et al., "Toll-like receptor 9 inhibition reduces mortality in polymicrobial sepsis", The Journal of Experimental Medicine, vol. 205, No. 6, May 12, 2008, pp. 1277-1283.

(56) References Cited

OTHER PUBLICATIONS

Yamanishi et al., "TIM1 is an endogenous ligand for LMIR5/CD300b: LMIR5 deficiency ameliorates mouse kidney ischemia/reperfusion injury", The Journal of Experimental Medicine, vol. 207, No. 7, Jun. 21, 2010, pp. 1501-1511.

An et al., "SHP-2 Phosphatase Negatively Regulates the TRIF Adaptor Protein-Dependent Type 1 Interferon and Proinflammatory Cytokine Production", Immunity, vol. 25, Dec. 2006, pp. 919-928.

Yang et al., "Site-specific gene targeting in mouse embryonic stem cells with intact bacterial artificial chromosomes", Nature Biotechnology, vol. 21, Apr. 2003, pp. 447-451.

Van Rooijen, "The liposome-mediated macrophage 'suicide' technique", Journal of Immunological Methods, vol. 124, Nov. 13, 1989, pp. 1-6.

Asano et al., "A genome-wide association study identifies three new susceptibilty loci for ulcerative colitis in the Japanese population", Nature Genetics, vol. 41, No. 12, Dec. 2009, pp. 1325-1331.

Kayama et al., "Intestinal CX3C chemokine receptor 1high (CX3CR1high) myeloid cells prevent T-cell-dependent colitis", Proceedings of the National Academy of Sciences of the United States of America, vol. 109, No. 13, Mar. 27, 2012, pp. 5010-5015.

Wong et al., "Activation of Eosinophils Interacting with Dermal Fibroblasts by Pruritogenic Cytokine IL-31 and Alarmin IL-33: Implications in Atopic Dermatitis", PLoS One, vol. 7, Issue 1, Jan. 17, 2012, pp. 1-13.

Nakajima et al., "Langerhans cells are critical in epicutaneous sensitization with protein antigen via thymic stromal lymphopoietin receptor signaling", J. Allegy Clin Immunol, vol. 129, No. 4, Apr. 2012, pp. 1048-1055.e6; Epub Mar. 3, 2012.

Otsuka et al., "Requirement of Interaction between Mast Cells and Skin Dendritic Cells to Establish Contact Hypersensitivity", PLoS One, vol. 6, Issue 9, Sep. 30, 2011, pp. 1-10.

Rakoff-Nahoum et al., "Recognition of Commensal Microflora by Toll-Like Receptors is Required for Intestinal Homeostasis", Cell, vol. 118, Jul. 23, 2004, pp. 229-241.

Freitag et al., "Gliadin-primed CD4+CD45RBlowCD25—T cells drive gluten-dependent small intestinal damage after adoptive transfer into lymphopenic mice" Gut., vol. 58, No. 12, Dec. 2009, pp. 1597-1605.

Ohta et al., "IL-15-Dependent Activation-Induced Cell Death-Resistant Th1 Type CD8 αβ+NK1.1+ T Cells for the Development of Small Intestinal Inflammation", The Journal of Immunology, vol. 169, 2002, pp. 460-468.

Depaolo et al., "Co-adjuvant effects of retinoic acid and IL-15 induce inflammatory immunity to dietary antigens", Nature, vol. 471, Mar. 10, 2011, pp. 220-225.

Denning et al., "Lamina propria macrophages and dendritic cells differentially induce regulatory and interleukin 17-producing T cell responses", Nature Immunology, vol. 8, No. 10, Oct. 2007, pp. 1086-1094.

Wang et al., "A PCR primer bank for quantitative gene expression analysis", Nucleic Acids Research, 2003, vol. 31, No. 24; e154, pp. 1-8.

Maiuri et al., "Association between innate response to gliadin and activation of pathogenic T cells in coeliac disease", The Lancet, vol. 362, Jul. 5, 2003, pp. 30-37.

Thomas et al., "Gliadin Stimulation of Murine Macrophage Inflammatory Gene Expression and Intestinal Permeability are MyD88-Dependent: Role of the Innate Immune Response in Celiac Disease", The Journal of Immunology, Vo. 176, 2006, pp. 2512-2521.

Weber et al., "Intestinal macrophages: differentiation and involvement in intestinal immunopathologies", Semin Immunopathol, vol. 31, 2009, pp. 171-184.

Serbina et al., "Monocyte-Mediated Defense Against Microbial Pathogens" Annu Rev Immunol., vol. 26, 2008, pp. 421-452.

Reinke et al., "Impairment of protein trafficking by direct interaction of gliadin peptides with actin" Experimental Cell Research, vol. 317, Jun. 1, 2011, pp. 2124-2135.

Barone et al., "Gliadin Peptide P31-43 Localises to Endocytic Vesicles and Interferes with Their Maturation", PLoS One, vol. 5, Issue 8, Aug. 2010, e12246; pp. 1-12.

Barone et al., "Gliadin-Mediated Proliferation and Innate Immune Activation in Celiac Disease Are Due to Alterations in Vesicular Trafficking", PLoS One, vol. 6, Issue 2, Feb. 2011, e17039; pp. 1-12.

Oda-Nakahashi, C. et al., A novel therapeutic approach for sepsis using a monoclonal antibody against MAIR-I (CD300a), Proceedings of the Japanese Society for Immunology, 2009, vol. 39, p. 90, 1-K-W19-2-O/P.

Oda (Nakahashi), C. et al., "Activation of Mast Cells by Myeloid-associated Ig like Receptor-I (MAIR-I) mi yoru Mast Saibo no kaseika", Clinical Immunology & Alllergology, 2005, vol. 54, No. 2, pp. 142-148, with English translation.

Asano, K. et al., "Impaired Phagocytosis of Apoptotic Cells by Phagocytes and Autoimmune Diseases—Shoku Saibo ni yoru Apootosis Saibo no Donshoku Ijo to, Jiko Menreki Shikkan", Molcular Medicine, 2004, vol. 41, specical extra issue, pp. 171-177, with English translation.

Lavo, B. et al., "Challenge with Gliadin Induces Eosinophil and Mast Cell Activation in the Jejunum of patients with Celiac Disease", The American Journal of Medicine, Dec. 1989, vol. 87, No. 6, pp. 655-660.

Karra, L. et al., "Are we ready to downregulate mast cells?", Current Opinion in Immunology, 2009, vol. 21, No. 6, pp. 708-714.

Bachelet, I. et al., "A Novel Ige-cd300a Bispecific Antibody Fragment Abolishes Allergic Responses", Journal of Allergy and Clinical Immunology, Feb. 2006, vol. 117, No. 2, pp. S88.

Bachelet, I. et al., "The Inhibitory Receptor IRp60 (CD300a) is Expressed and Functional on Human Mast Cells", The Journal of Immunology, The American Association of Immunologists, Dec. 1, 2005, vol. 75, No. 12, pp. 7989-7995.

Munitz, A. et al., "Reversal of airway inflammation and remodeling in asthma by a bispecific antibody fragment linking CCR3 to CD300a", Journal of Allergy and Clinical Immunology, Nov. 6, 2006, vol. 118, No. 5, pp. 1082-1088.

Partial Supplementary European Search Report dated Nov. 24, 2015, issued in European Patent Application No. 12851748.9. (11 pages).

Eastaff-Leung, N. et al., Foxp3+ Regulatory T Cells, Th17 Effector Cells, and Cytokine Environment in Inflammatory Bowel Disease, J. Clin. Immunol., 2010, vol. 30, pp. 80-89.

Woodruff, S. et al., "Role of Eosinophils in Inflammatory Bowel and Gastrointestinal Diseases", JPGN, vol. 52, No. 6, Jun. 2011, pp. 650-661.

Bachelet, I. et al., "Mast Cell Costimulation by CD226/CD112 (DNAM-1/Nectin-2) A Novel Interface in the Allergic Process", The Journal of Biological Chemistry, vol. 281, No. 37, Sep. 15, 2006, pp. 27190-27196.

Bachelet, I. et al., "Abrogation of allergic reactions by a bispecific antibody fragment linking IgE to CD300a", Journal of Allergy and Clinical Immunology, vol. 117, Issue 6, Jun. 2006, pp. 1314-1320.

Choi, S. et al "Cutting Edge: Mouse CD300f (CMRF-35-Like Molecule-1) Recognizes Outer Membrane-Exposed Phosphatidylserine and Can Promote Phagocytosis", The Journal of Immunology, Aug. 2011, vol. 187, pp. 3483-3487.

"Immunoglobulin E", Wikipedia, the free encyclopedia, https://en.wikipedia.org/wiki/Immunoglobulin_E, Feb. 27, 2017.

* cited by examiner

[Fig. 1]
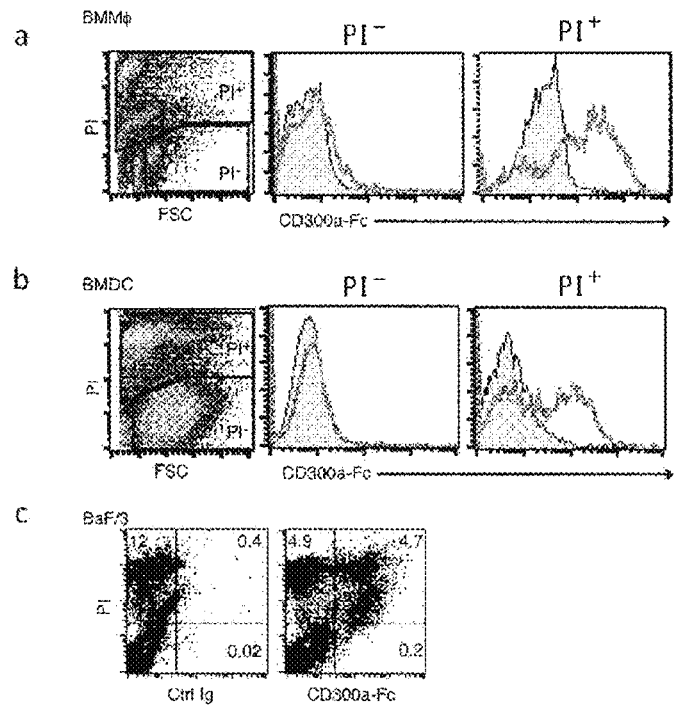
[Fig. 2A]
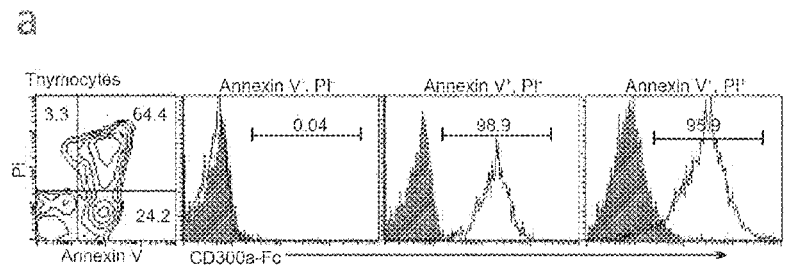
[Fig. 2B]
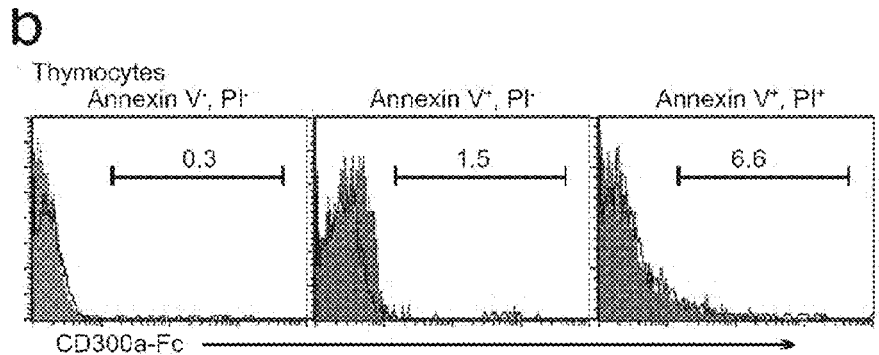

[Fig. 2C]
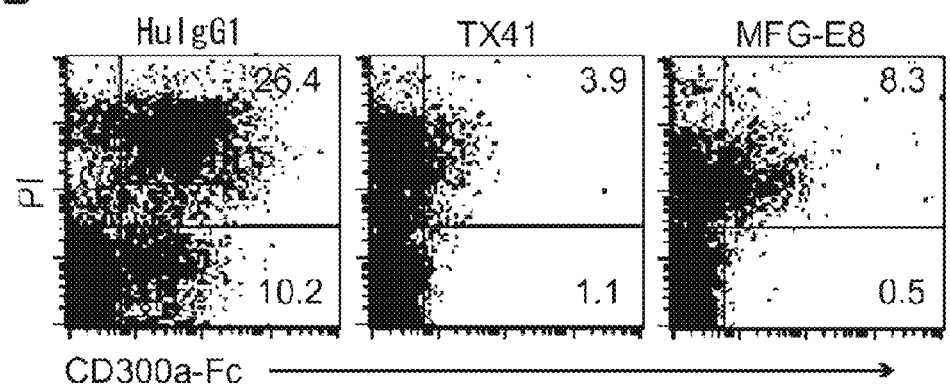
[Fig. 2D]
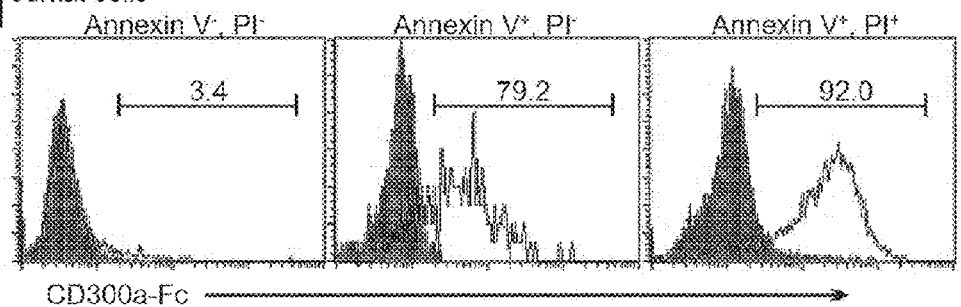
[Fig. 2E]
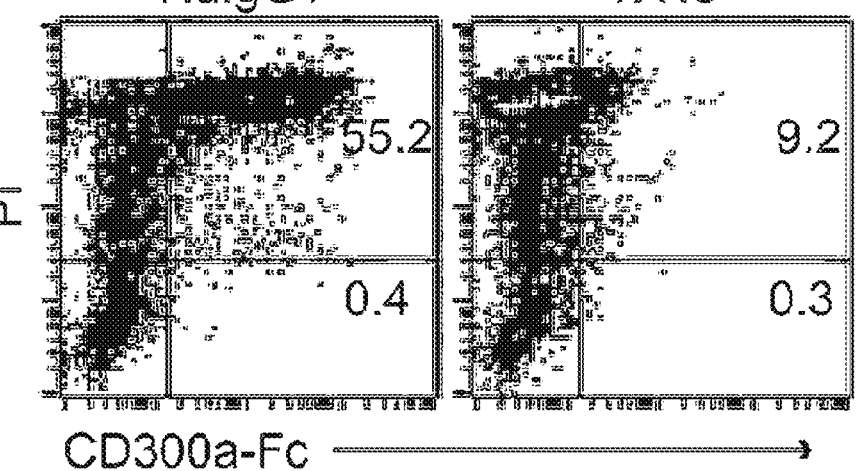

[Fig. 2F]
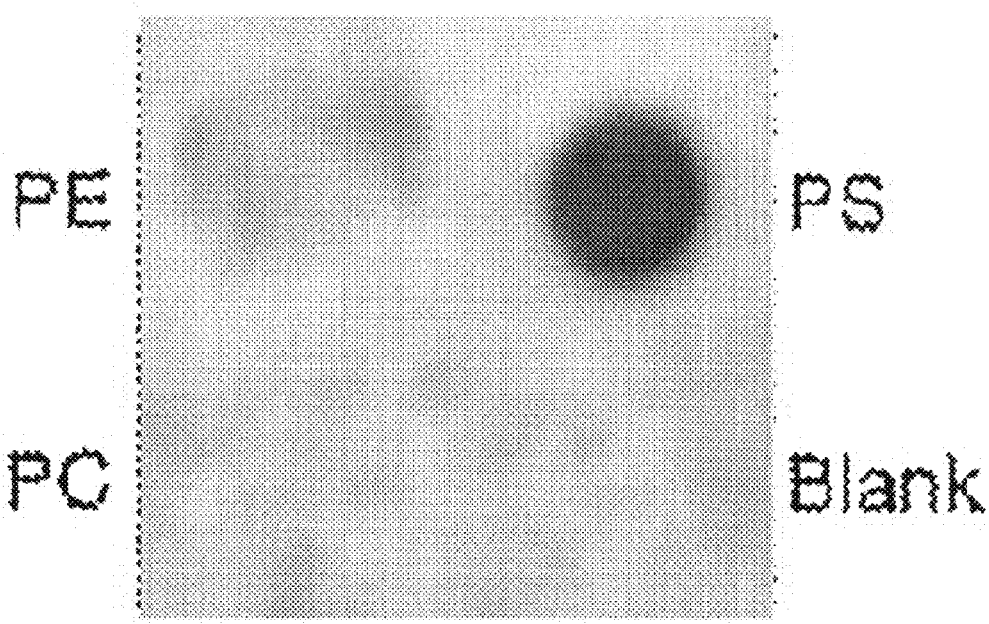
[Fig. 3A]
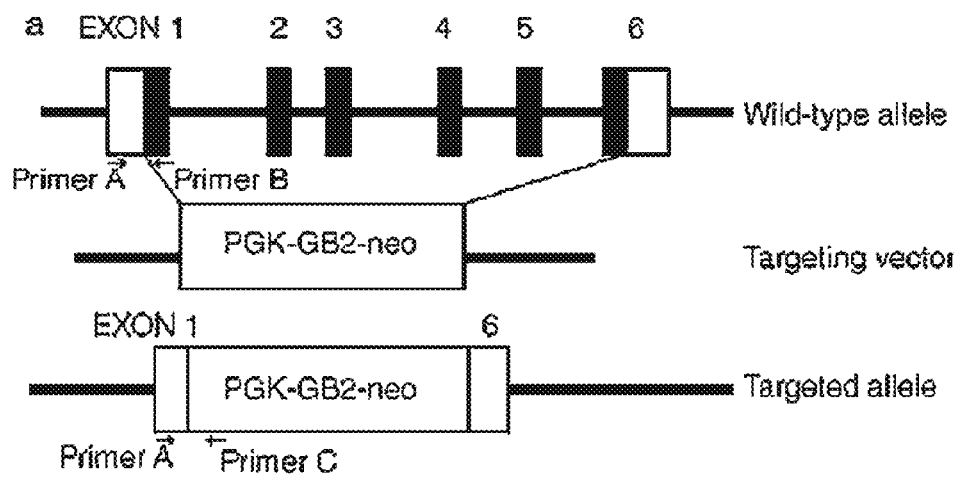

[Fig. 3B]
b
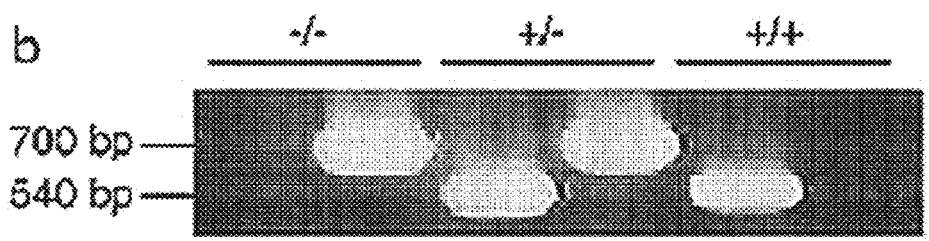
[Fig. 3C]
c
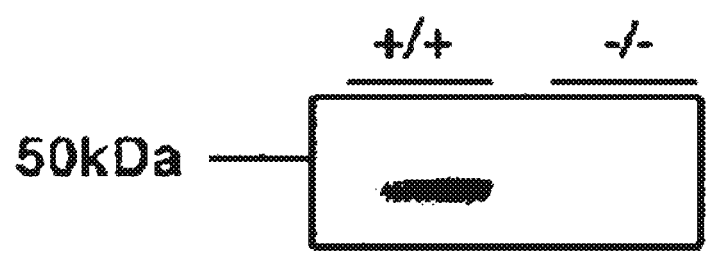
IB: Antibody to CD300a

[Fig. 3D]
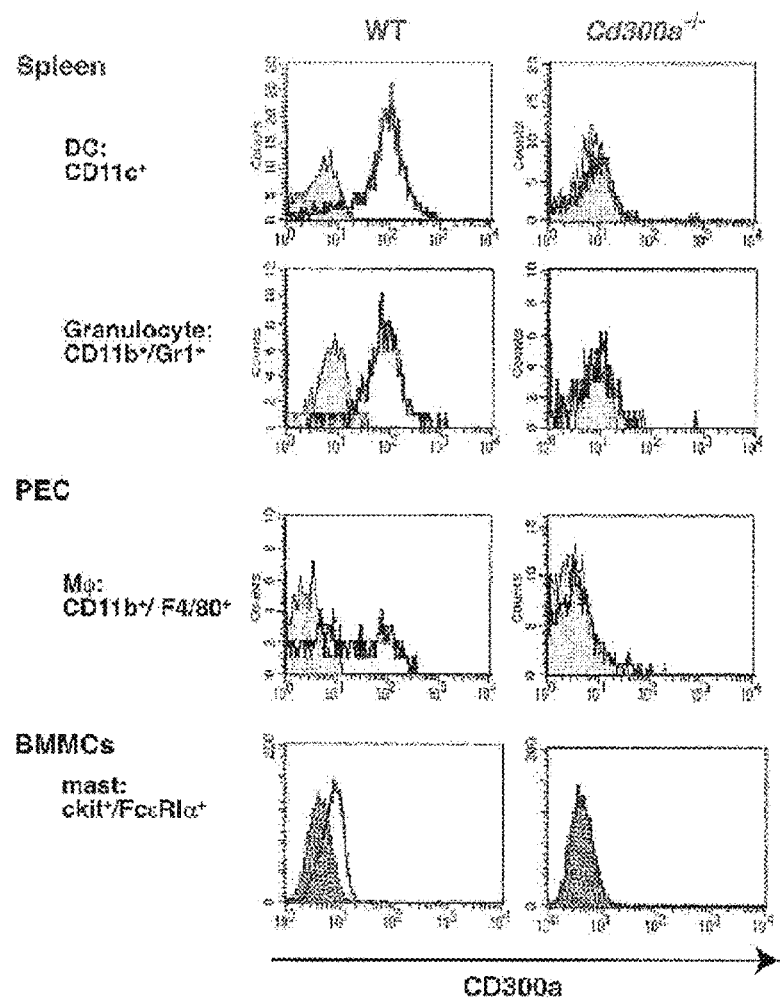
[Fig. 4A]
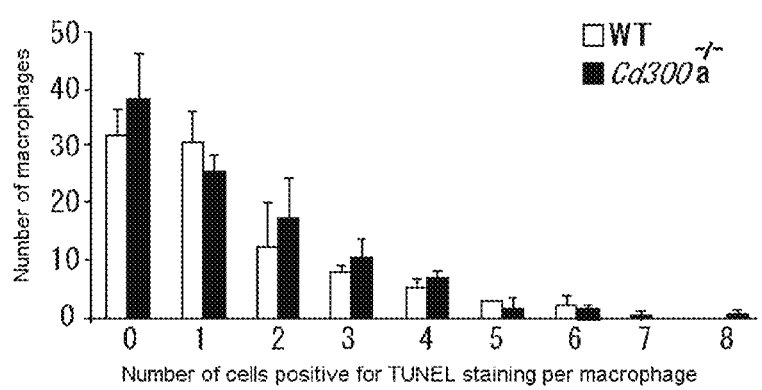

[Fig. 4B]
b
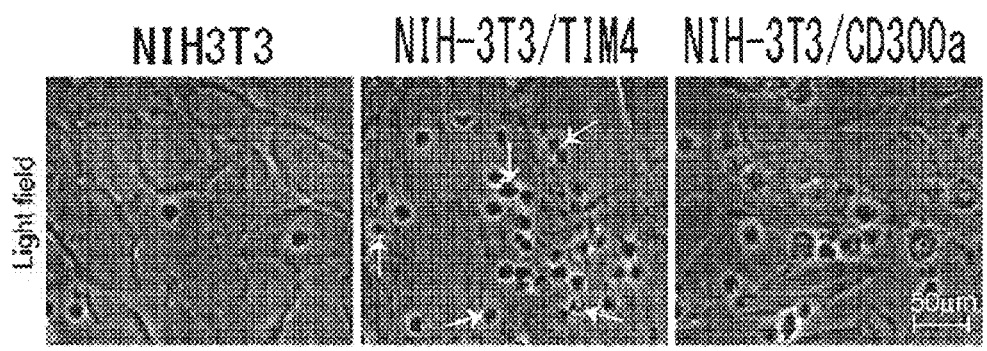
[Fig. 4C]
c
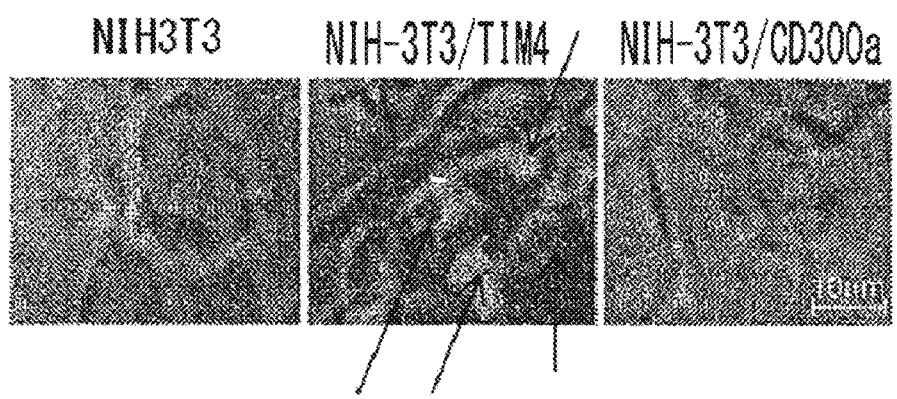

[Fig. 4D]
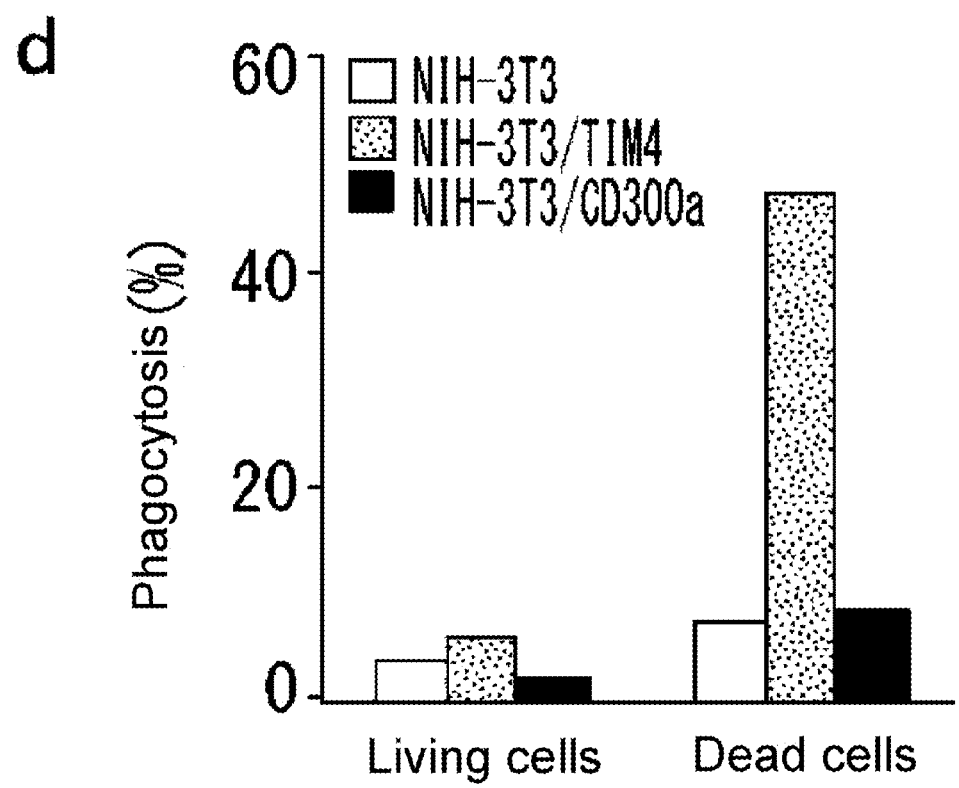

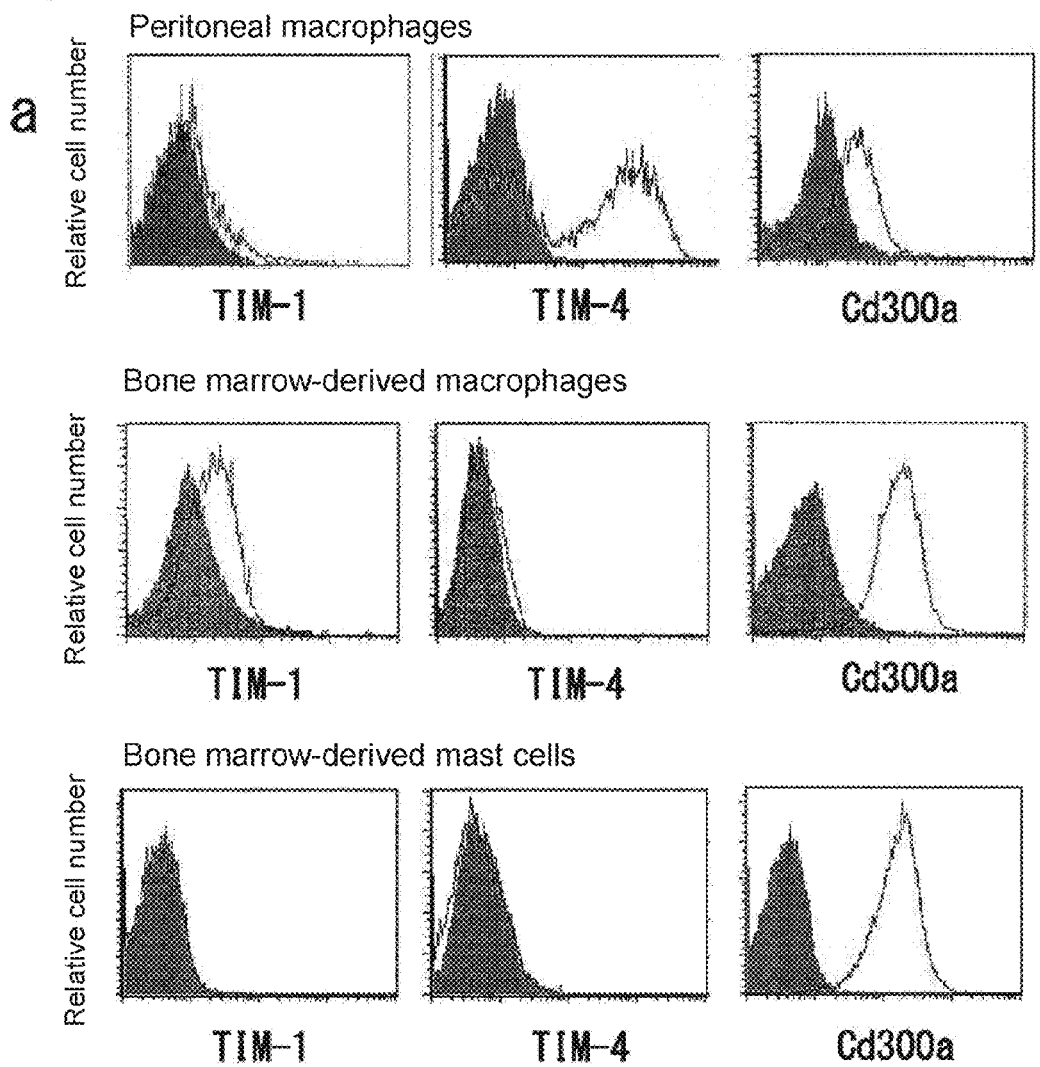
[Fig. 5A]

[Fig. 5B]
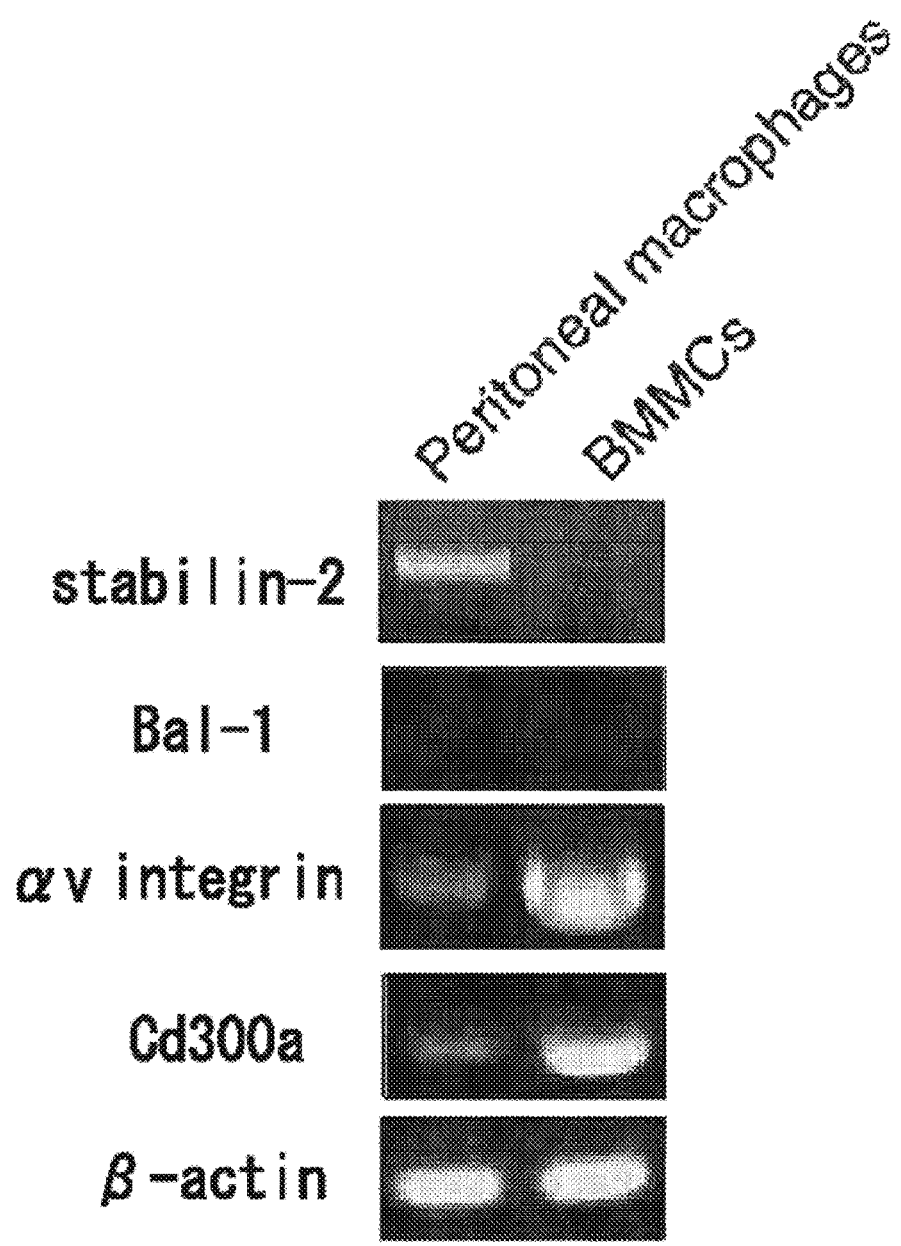

[Fig. 6A]
a
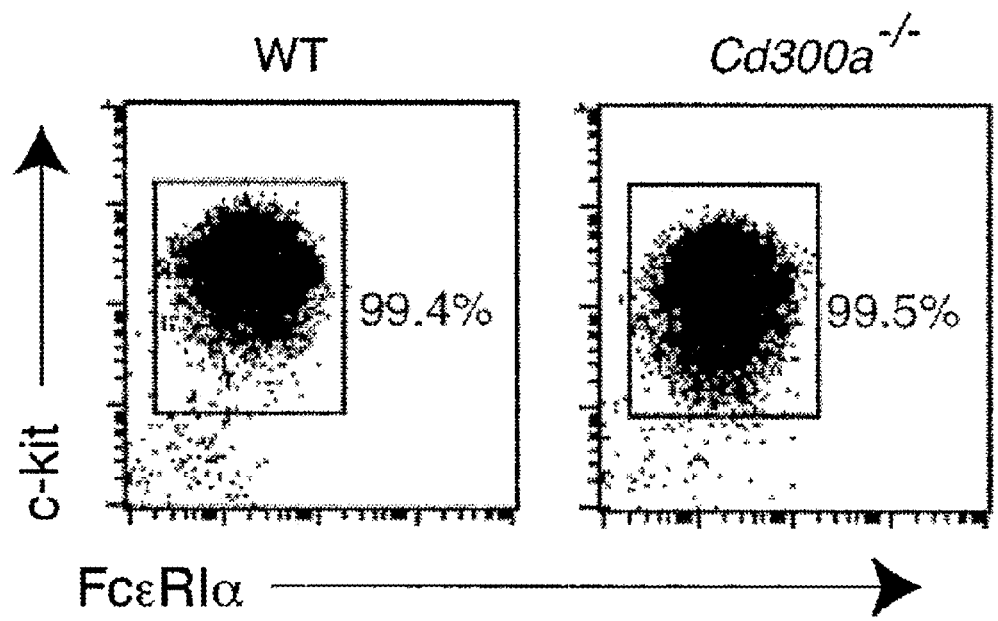
[Fig. 6B]
b
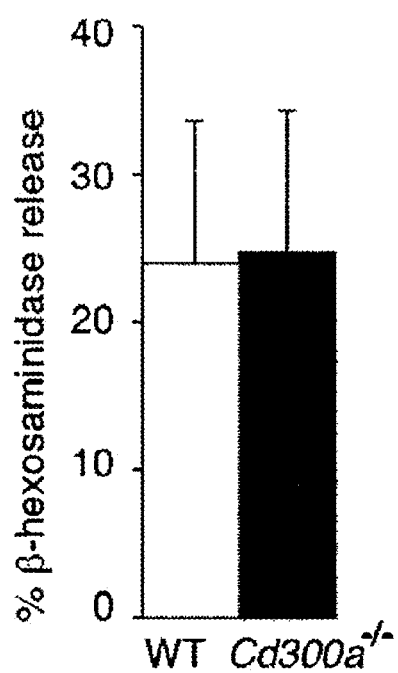

[Fig. 7A]
a
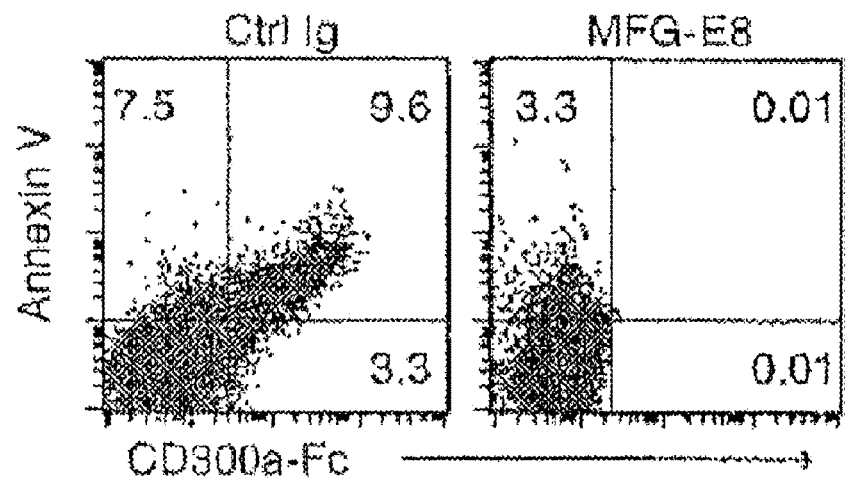
[Fig. 7B]
b
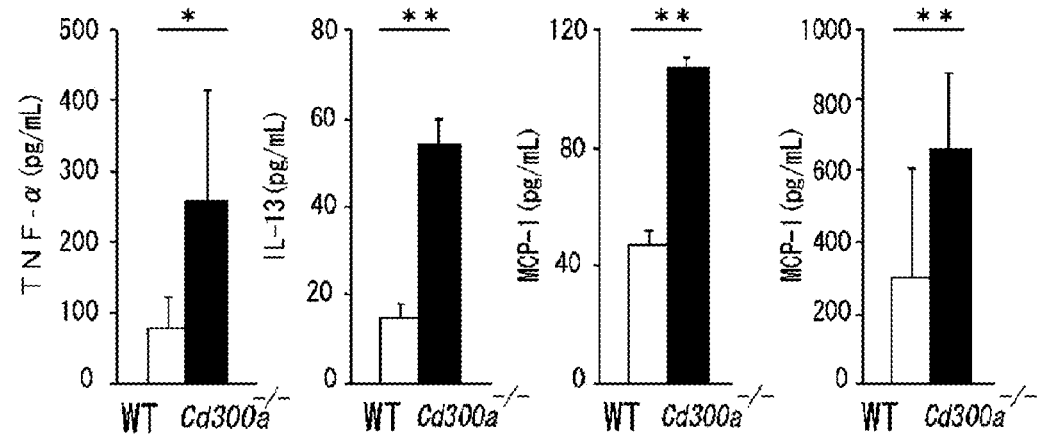

[Fig. 7C]
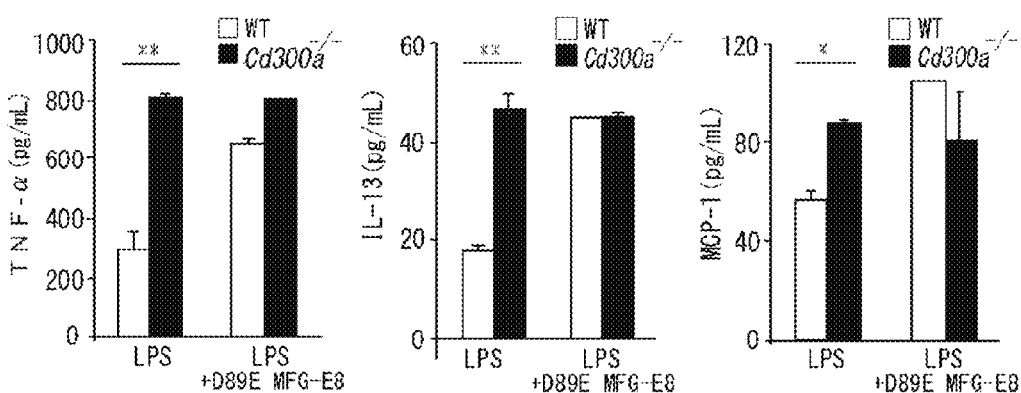
[Fig. 7D]
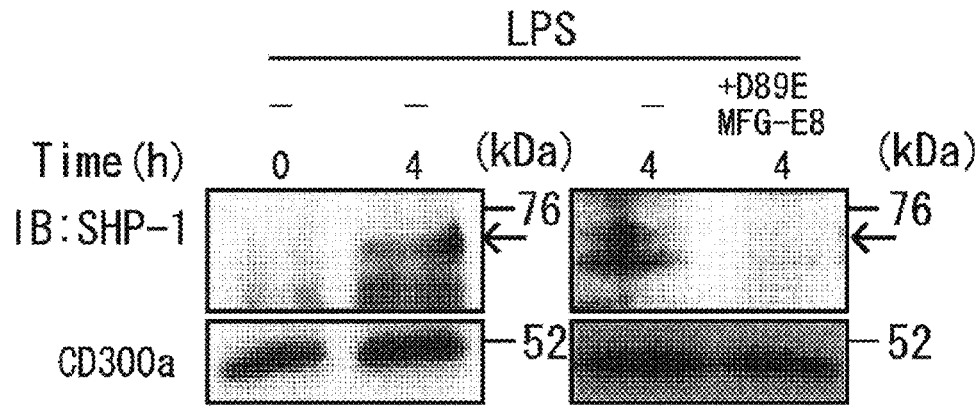
[Fig. 7E]

[Fig. 7F]
f
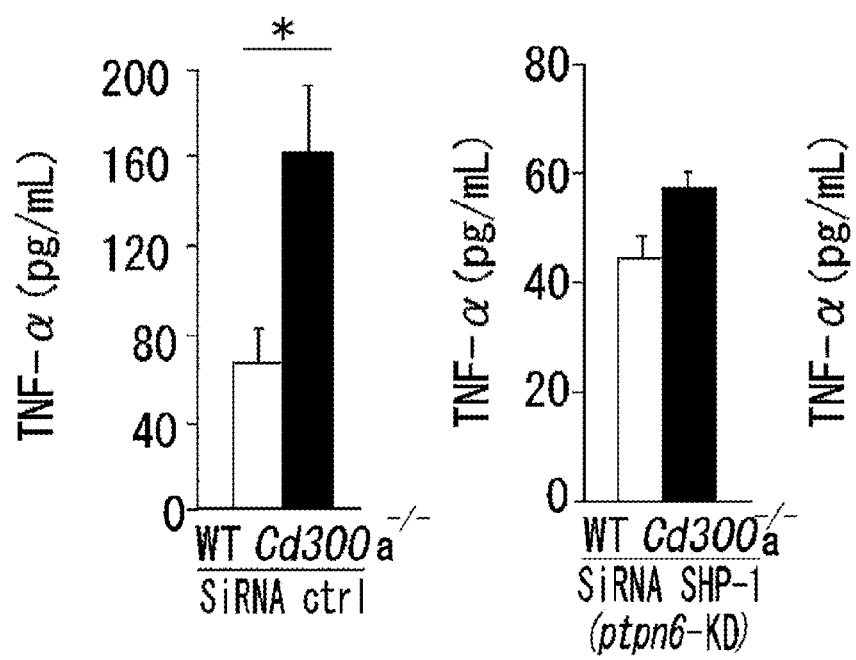

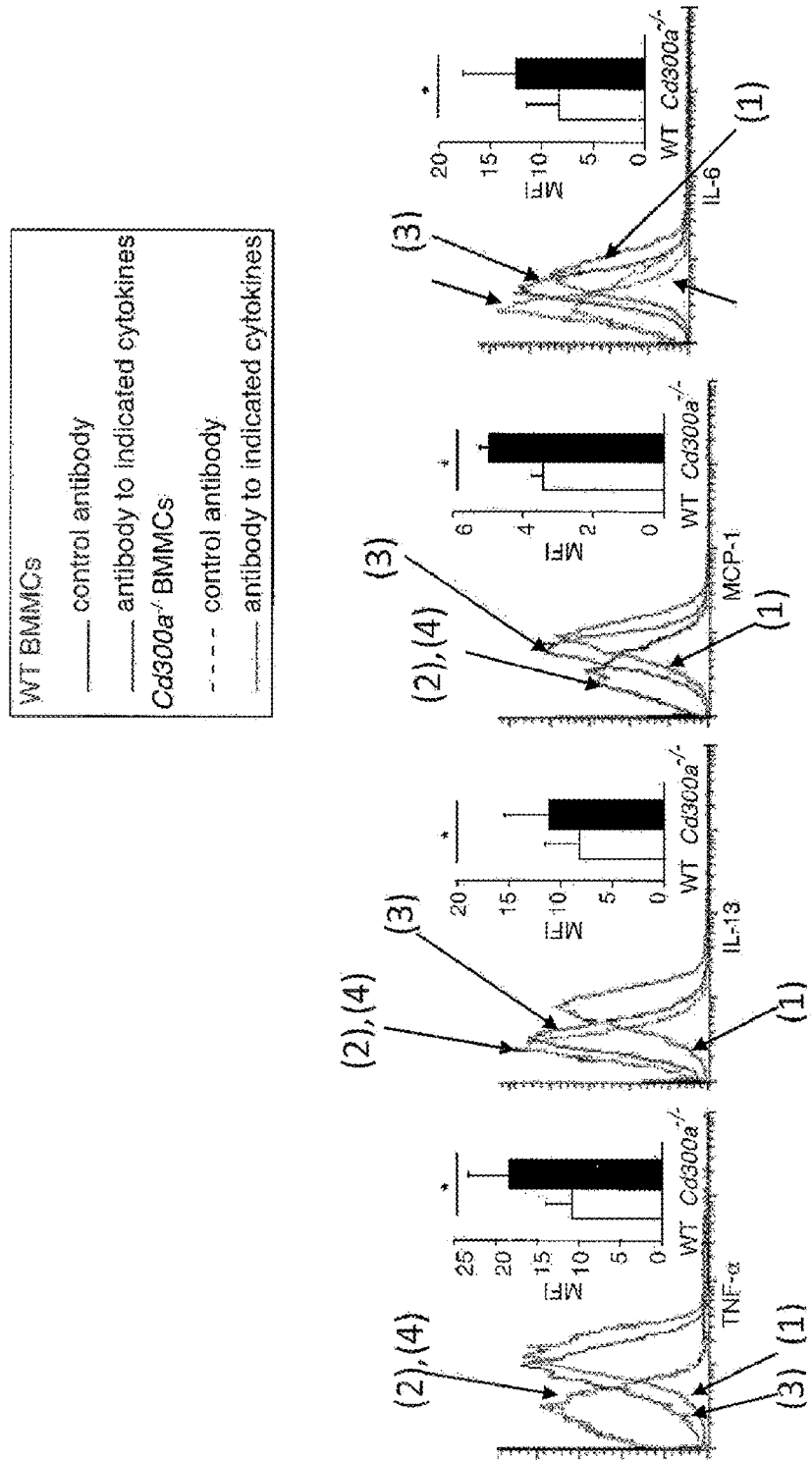
[Fig. 8]

[Fig. 9A]
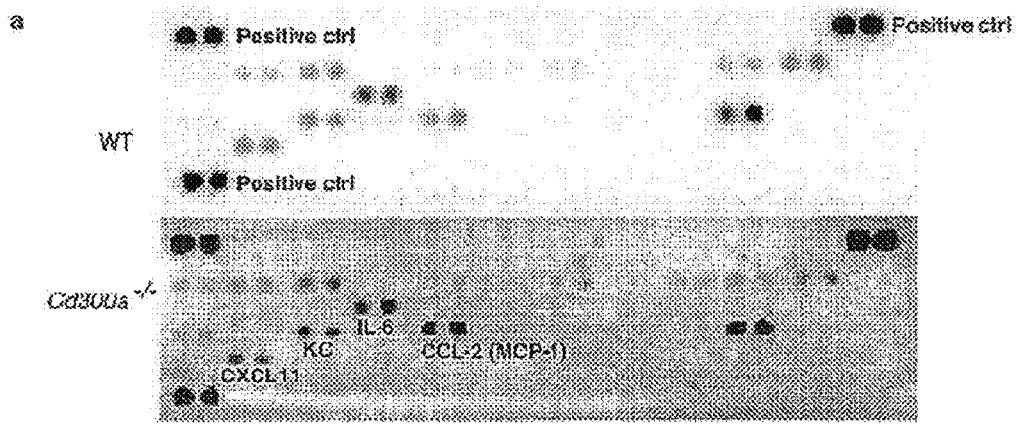
[Fig. 9B]
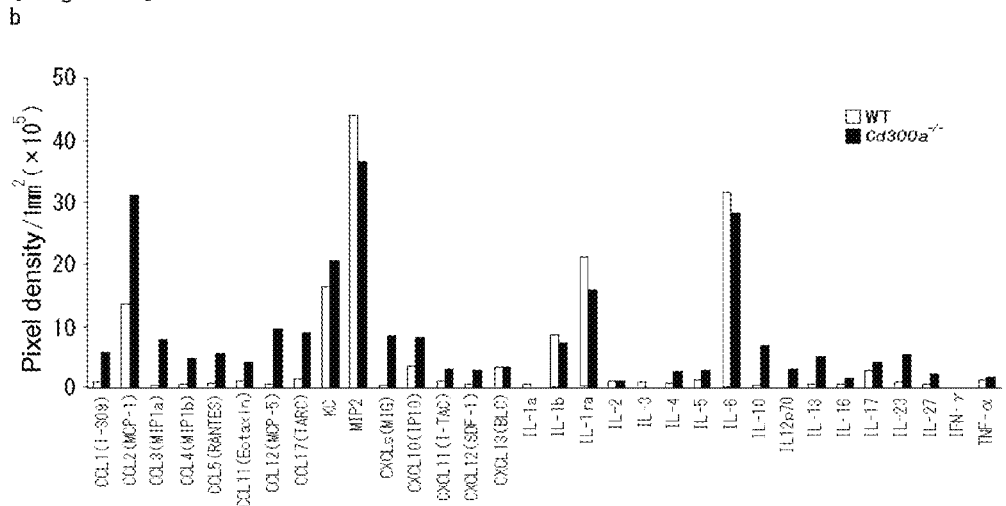

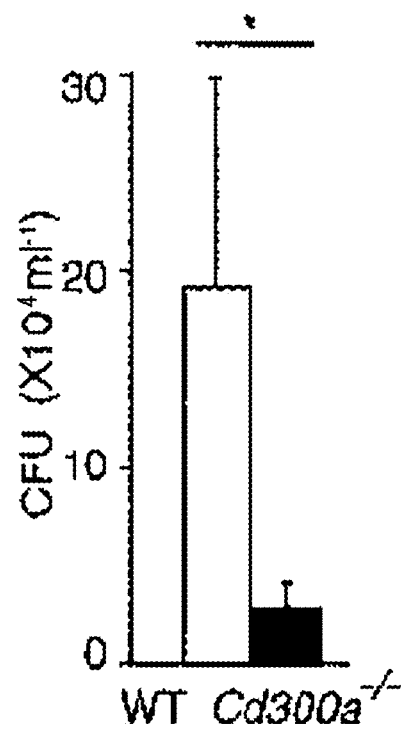
[Fig. 10A]

[Fig. 10B]
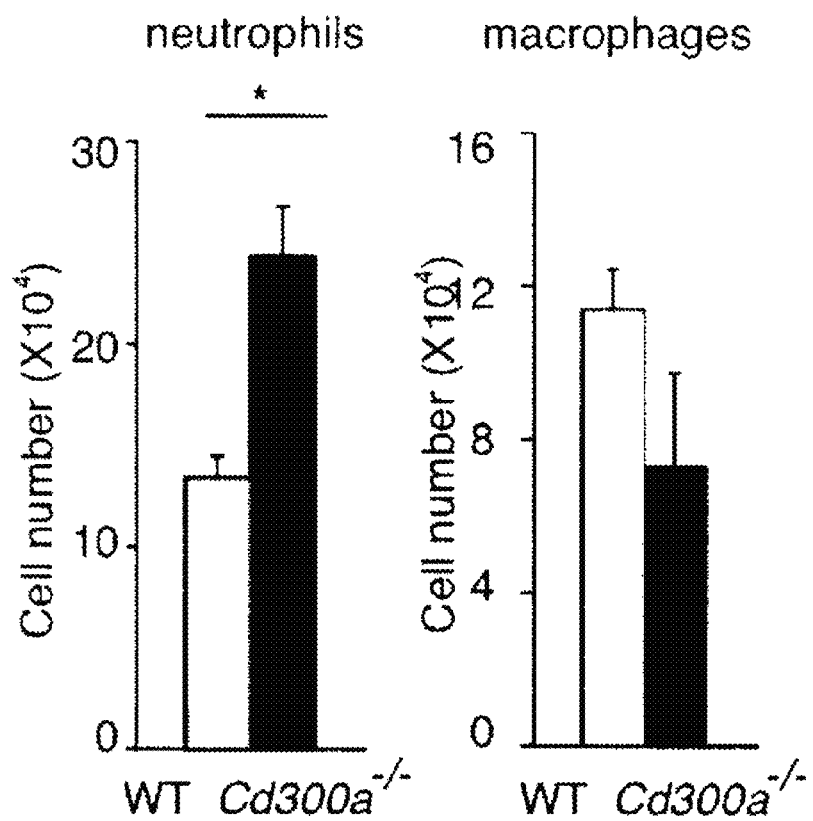

[Fig. 11]
(A)          (B)
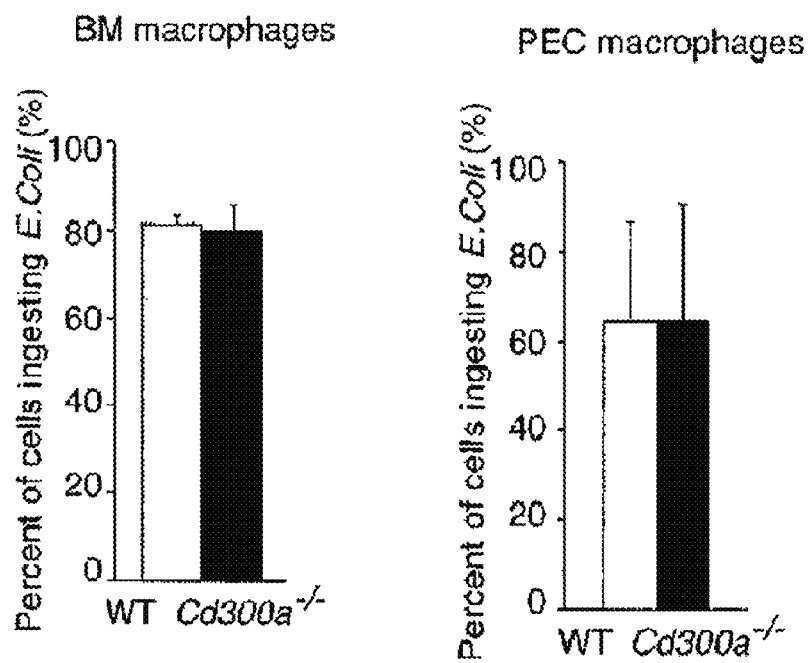
[Fig. 12A]
a
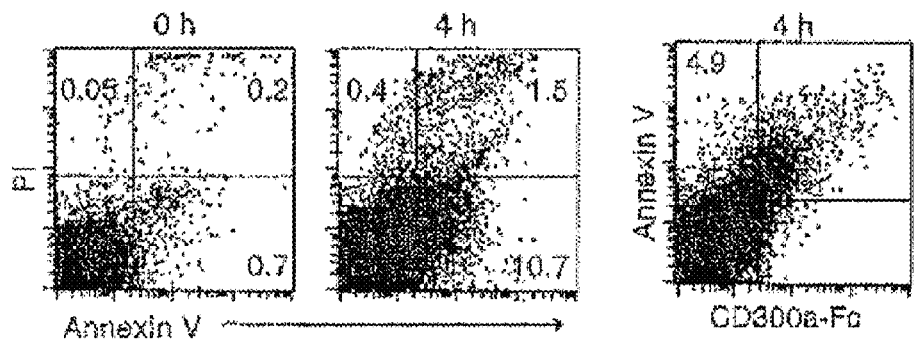

[Fig. 12B]
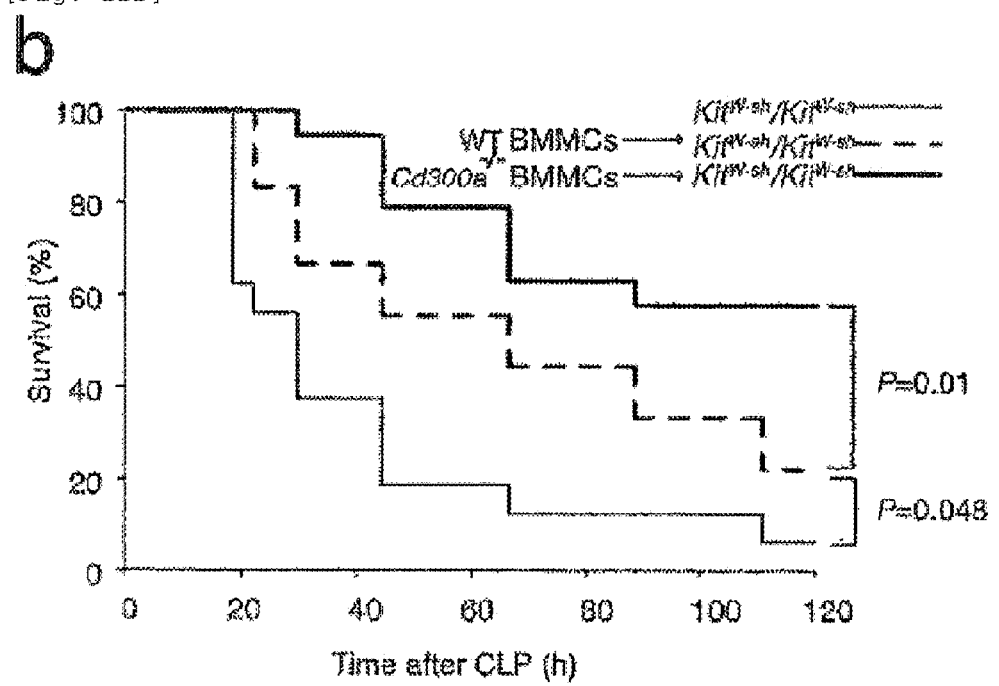

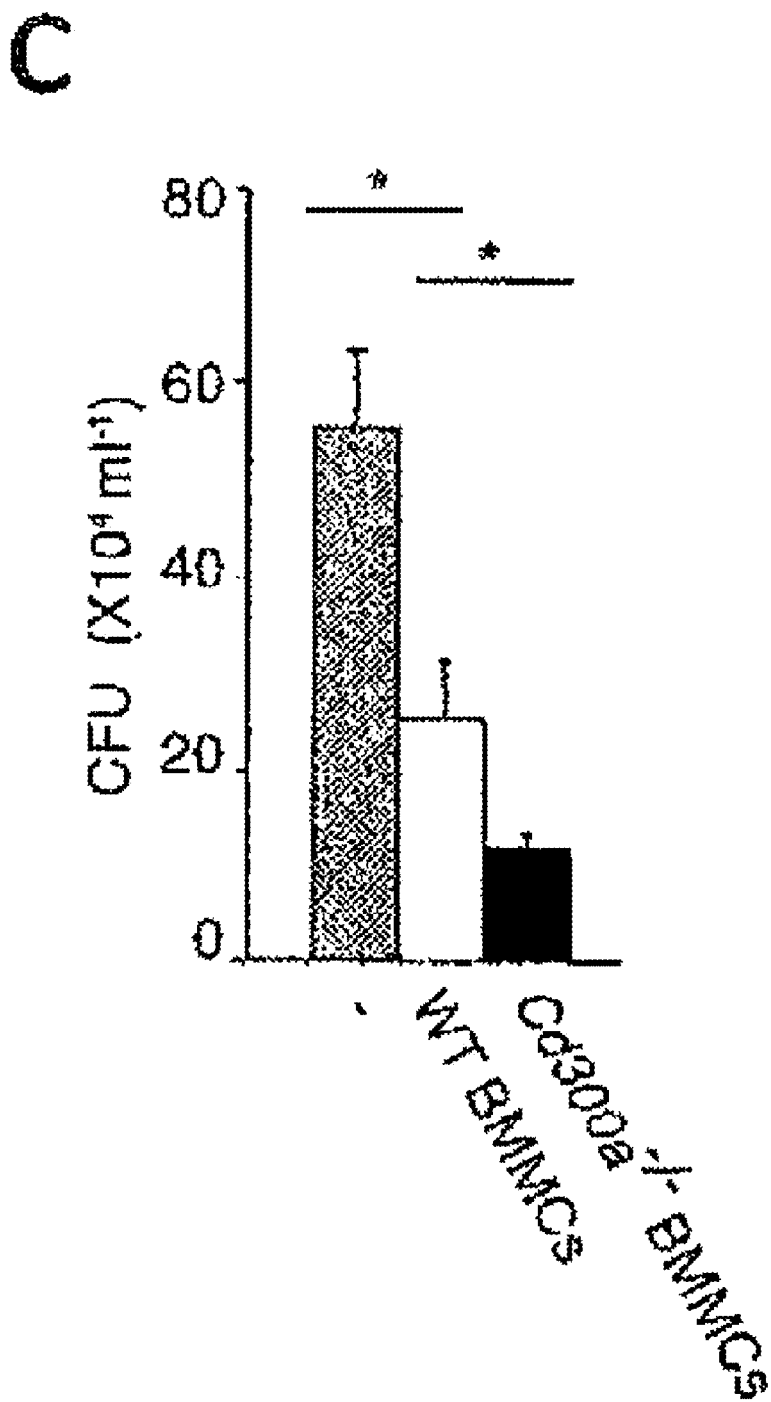
[Fig. 12C]

[Fig. 12D]
d
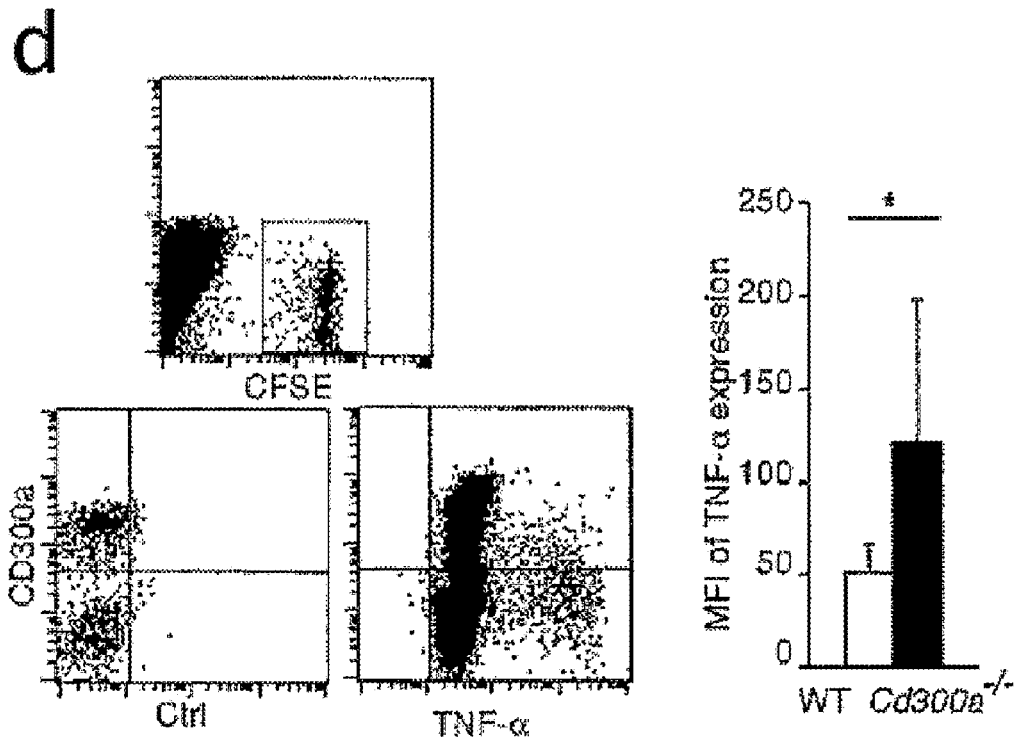
[Fig. 12E]
e
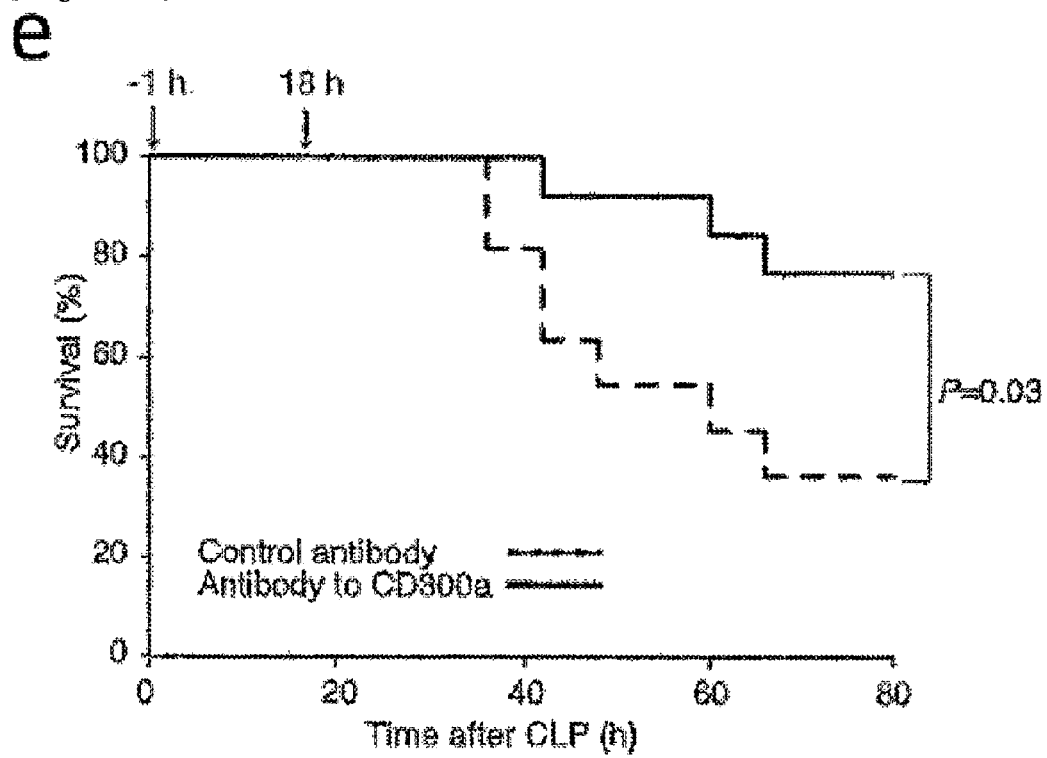

[Fig. 12F]
f
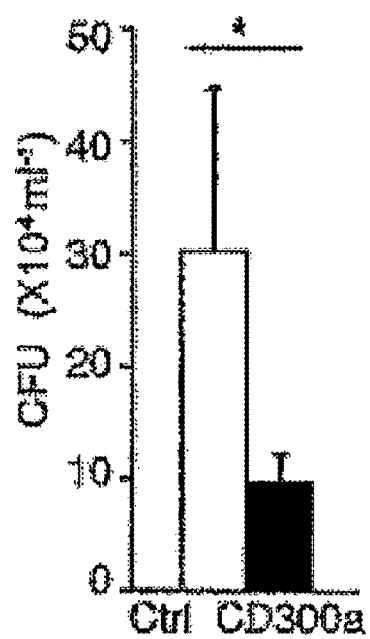
[Fig. 12G]
g
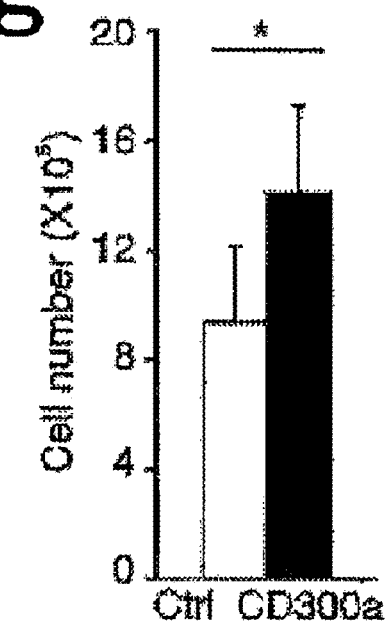

[Fig. 13A]
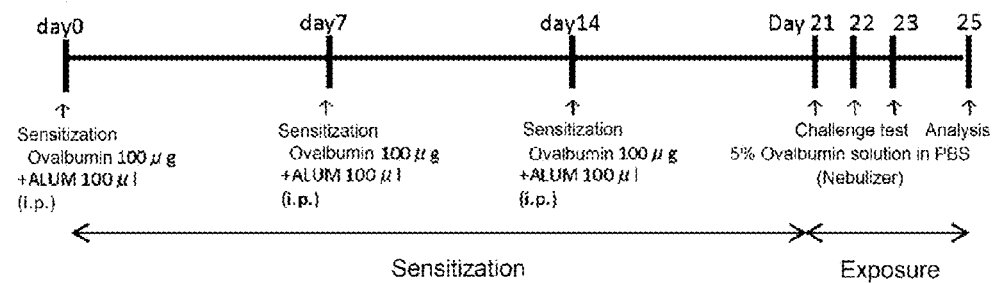
[Fig. 13B]
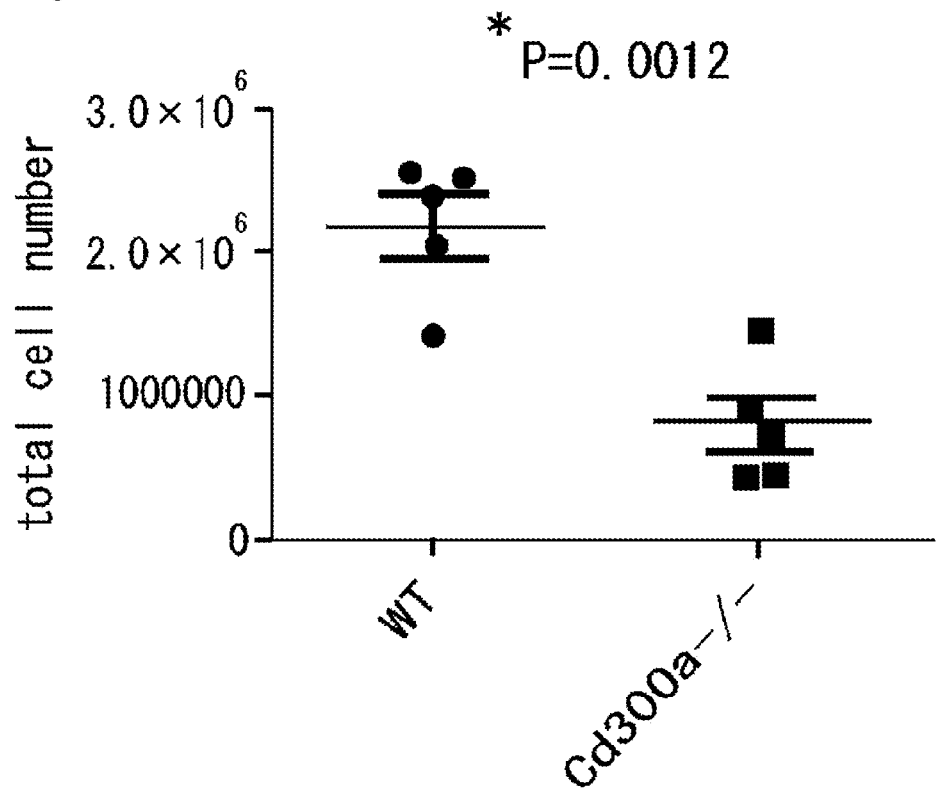

[Fig. 13C]
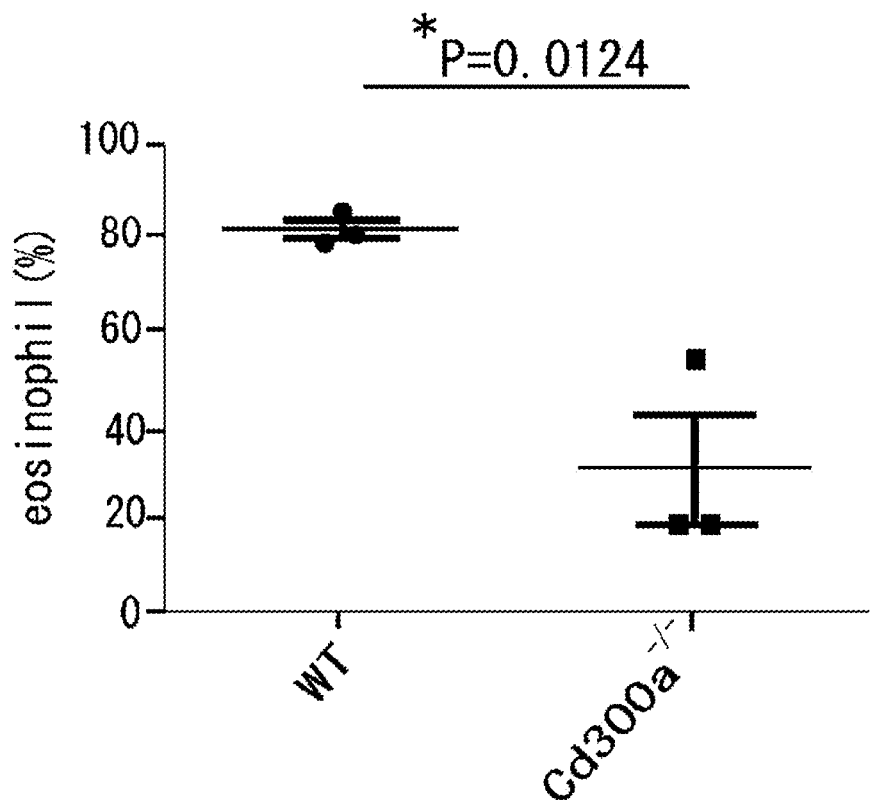
[Fig. 14]
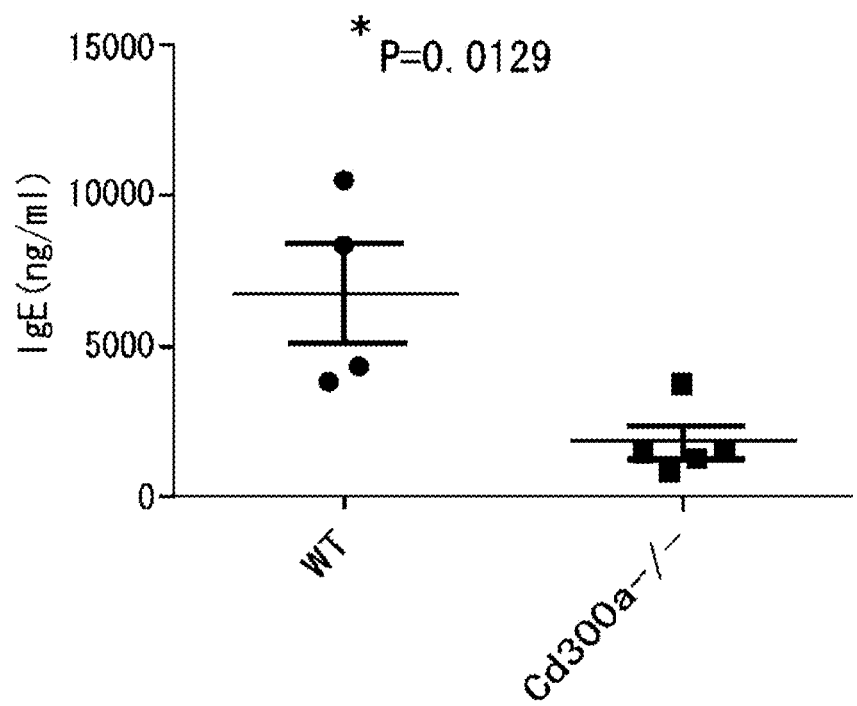

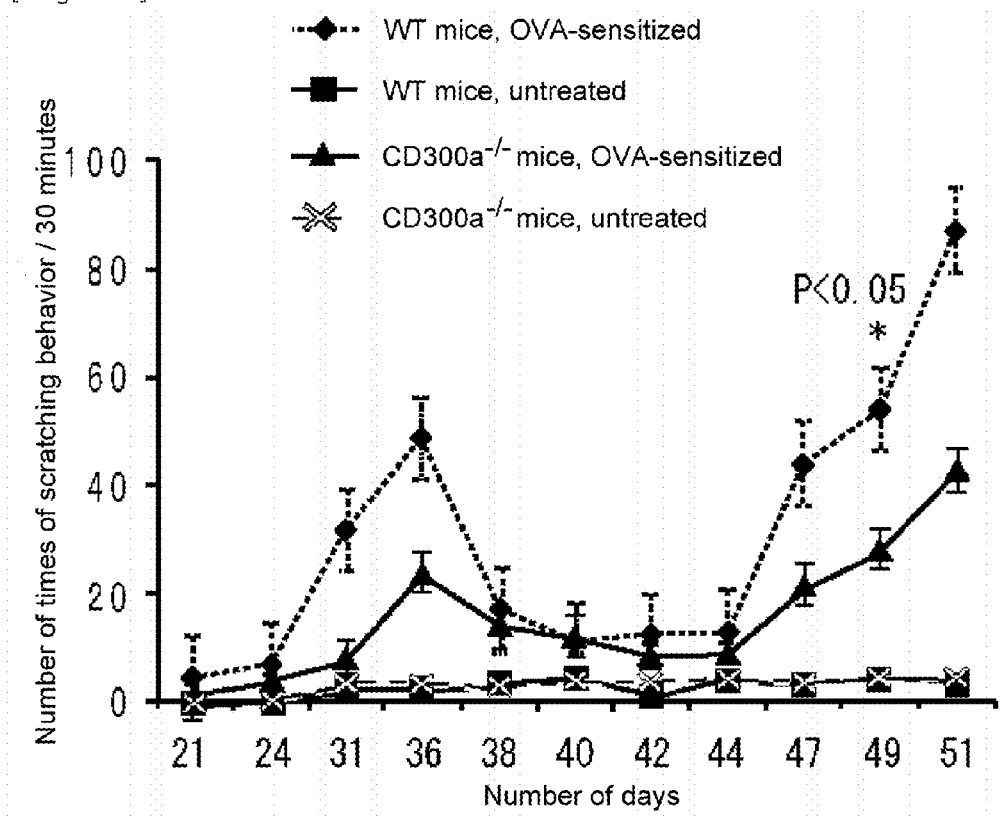

[Fig. 16]
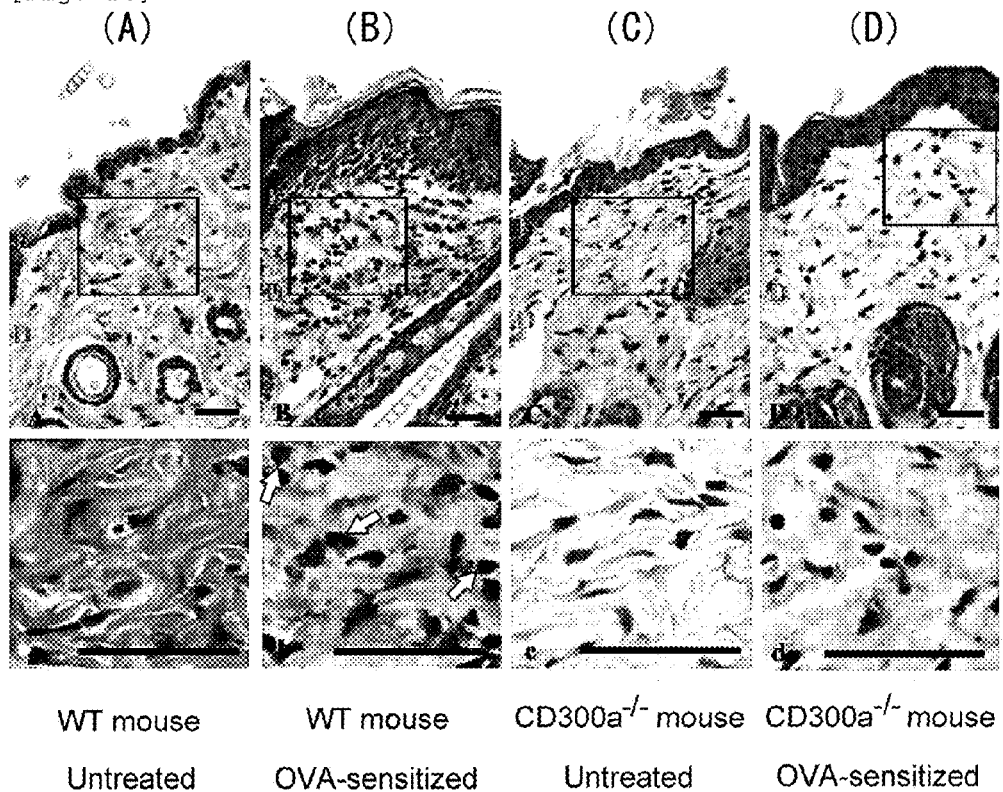
(A) WT mouse Untreated  (B) WT mouse OVA-sensitized  (C) CD300a$^{-/-}$ mouse Untreated  (D) CD300a$^{-/-}$ mouse OVA-sensitized
[Fig. 17]
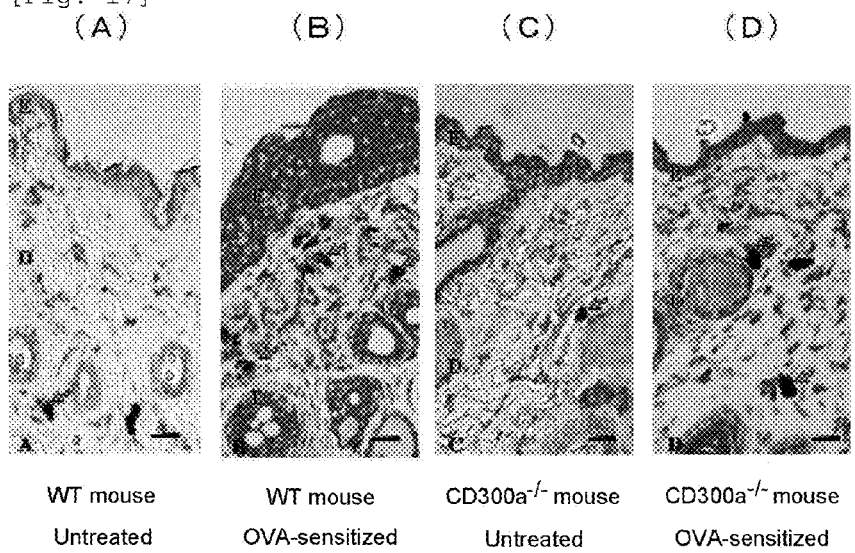
(A) WT mouse Untreated  (B) WT mouse OVA-sensitized  (C) CD300a$^{-/-}$ mouse Untreated  (D) CD300a$^{-/-}$ mouse OVA-sensitized

[Fig. 18A]
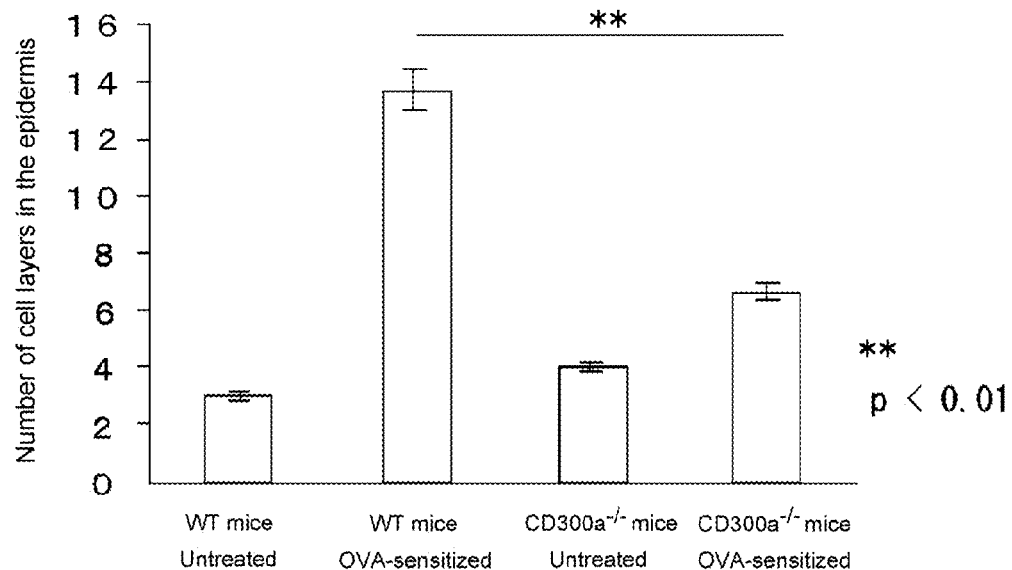
[Fig. 18B]
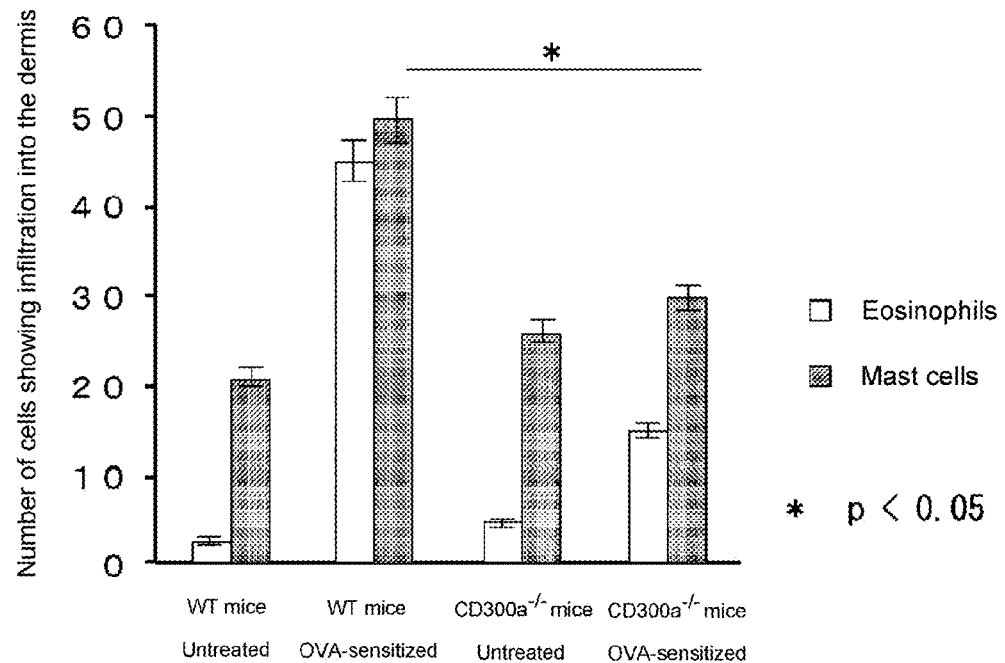

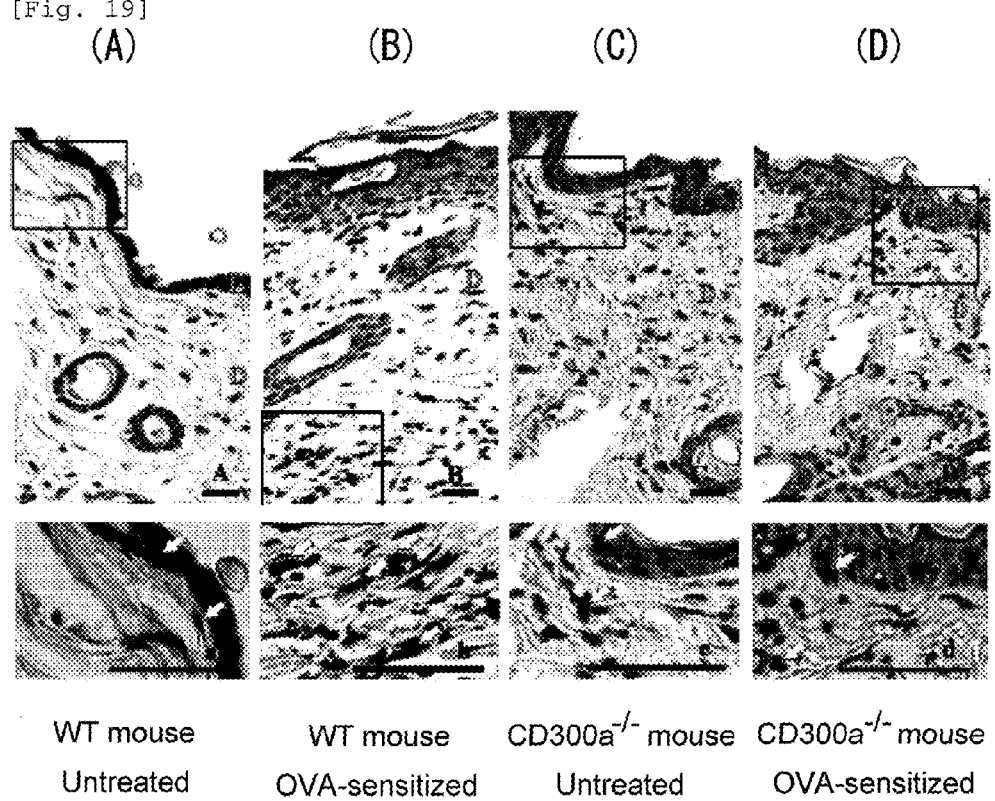

[Fig. 20]
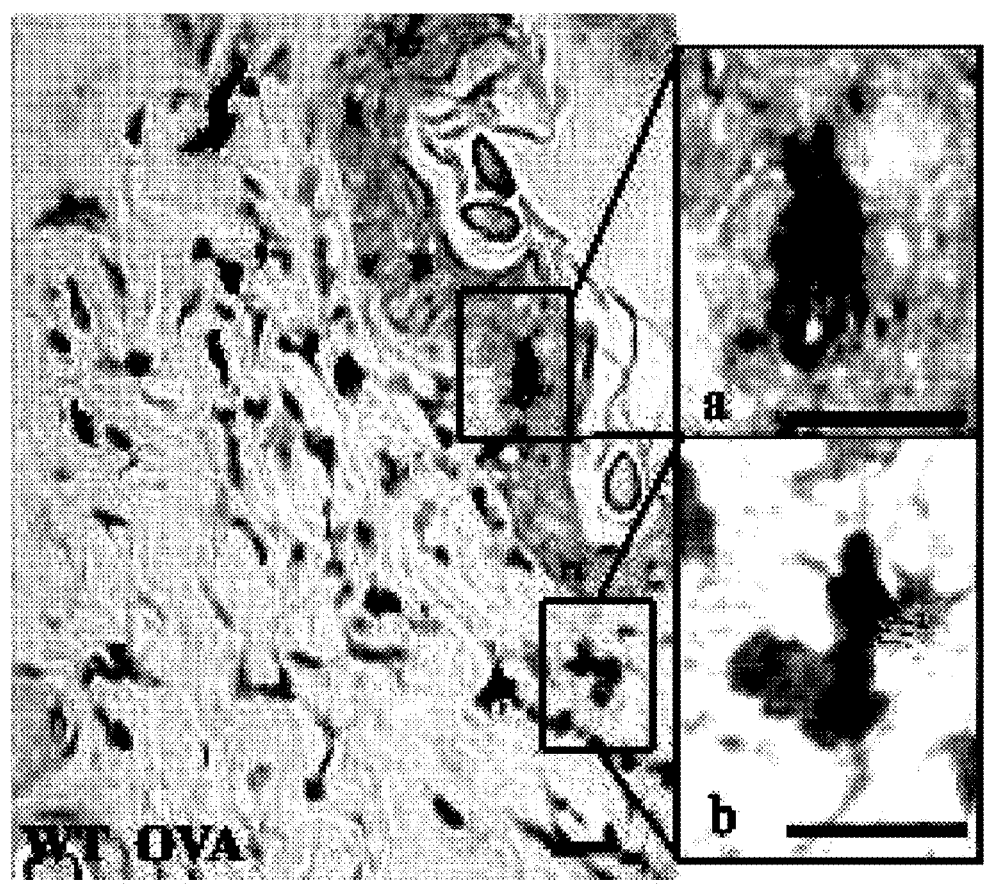

[Fig. 21]
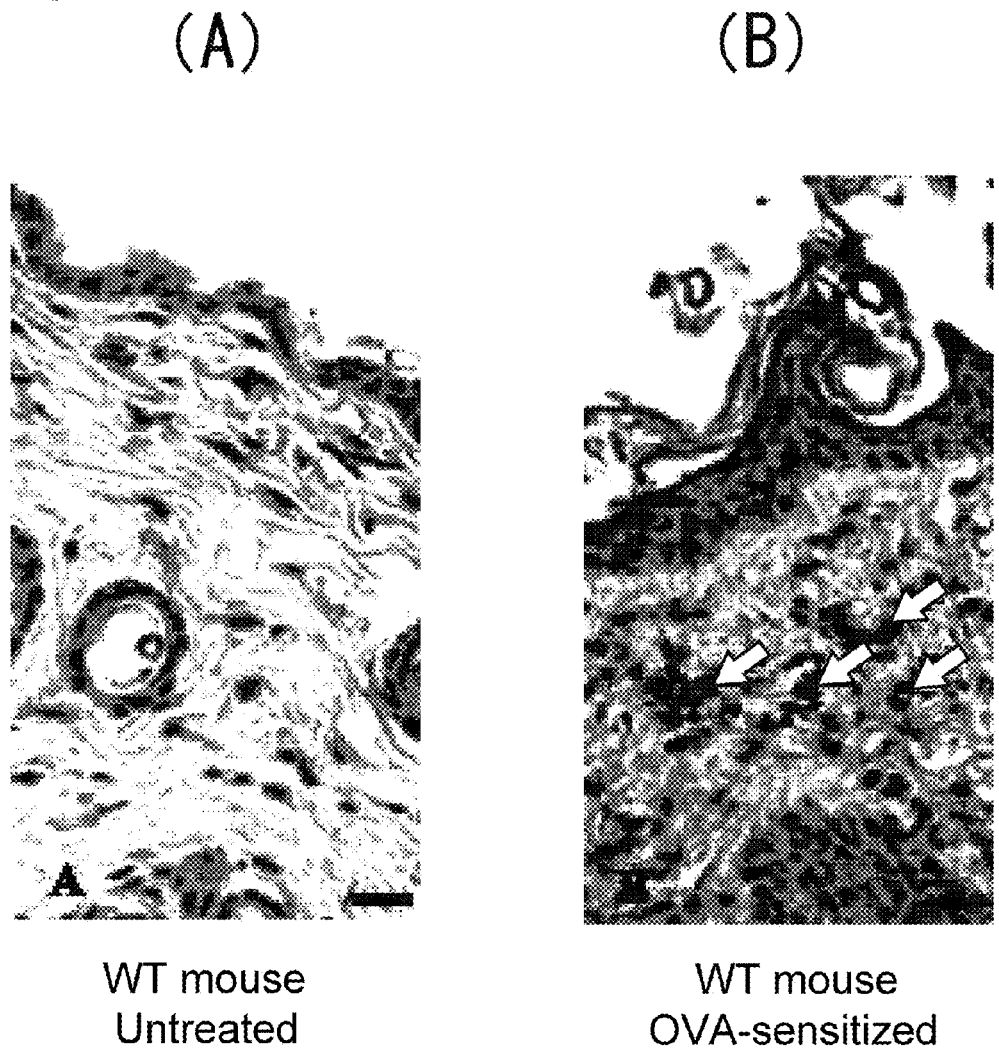
(A) WT mouse Untreated
(B) WT mouse OVA-sensitized
[Fig. 22]
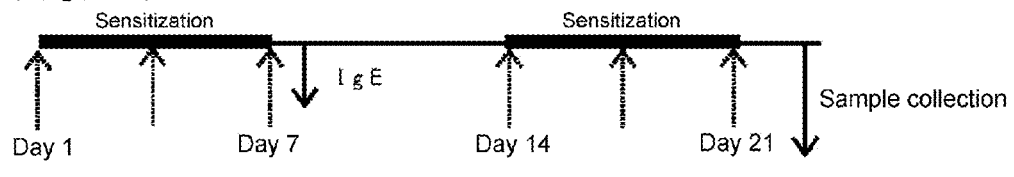
↑ = IV injection of TX-41 or TX74

[Fig. 23]
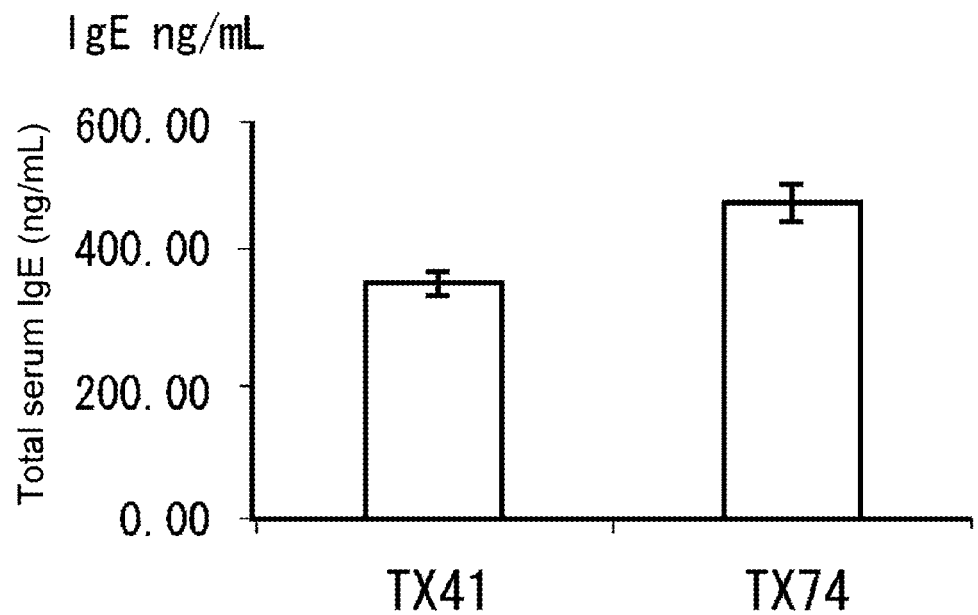
[Fig. 24]
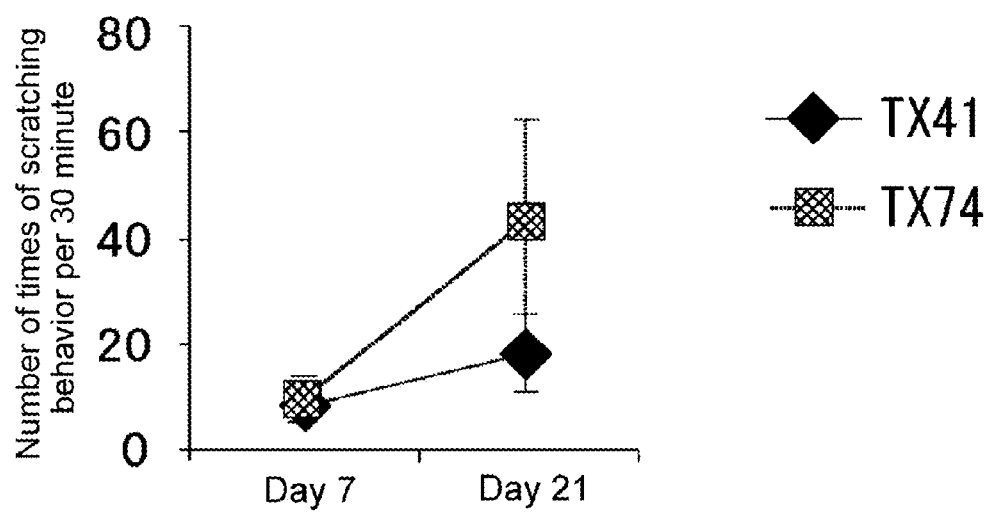

[Fig. 25]
(A)    (B) 
TX41          TX74

[Fig. 26]
(A) 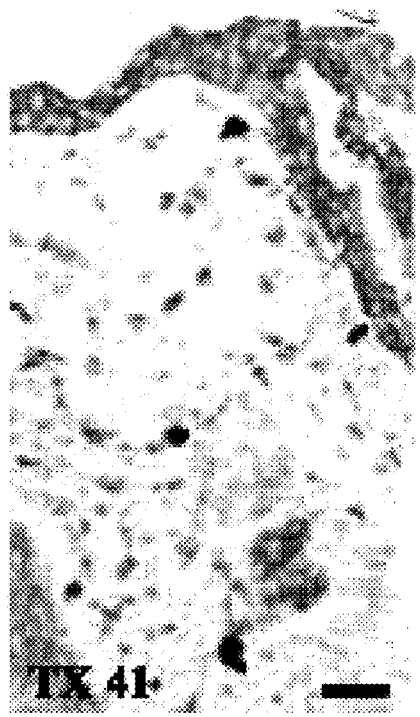 (B) 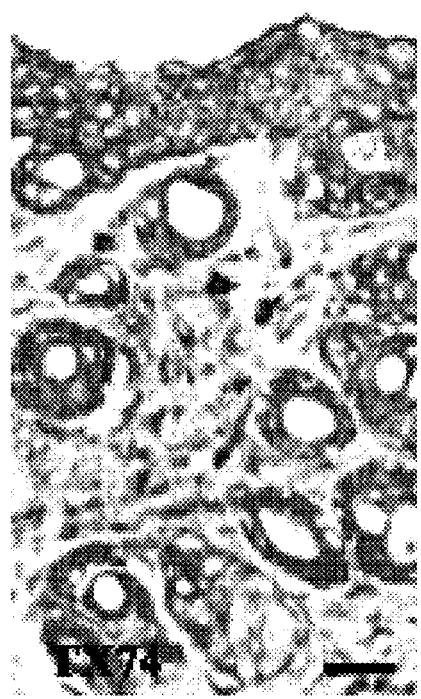
TX41　　　　　　TX74

[Fig. 27]

```
                    1                                              50
TX41 (H chain)      IEVKLVESGPGILQ-P---SQTLSLTCTFSG---FSLSTYGMGVGWIRQ-PS
(SEQ ID NO: 1)      *** * **   *    *    * **   *  **   *   *  * **   * *
TX49 (H chain)      IEVQLQQSGAE-LVKPGASVKLS---CKASGYTFT-S-YWMQ---WVKQRP-
(SEQ ID NO: 3)
                    51                                             100
TX41 (H chain)      GKGLEWLANIWWDD-DKY---YNPSLKNR---LTISKDTSNN-----QAFLKI
                    * ****    *  *  *  *  * * **    *   **   ***       * *
TX49 (H chain)      GQGLEWIGEI---DPSDSYTNYNQKFKGKATLTV---DTSSSTTYMQ---LSS 101                                            150
TX41 (H chain)      -TNVDTADTATYYCARPTTE-GD---YW-----GQGVMVTVSSAETTAPSV
                     * *   *****    *  **     * *  ******  ** ***
TX49 (H chain)      LTSEDSAV----YYCARWGMAYGTSSYWYFDVWGTGTTVTVSSAKTTPPSV 151
TX41 (H chain)      YPLAPGI
                    ******                    71 identical bases
TX49 (H chain)      YPLAPGI
```

```
                    1                                              50
TX41 (L chain)      DFLAFLHHLTGSCA-QFVLTQPNSV-STNLGSTVKLSCKR-STGNIGSNY
(SEQ ID NO: 2)      *             * *   **  *   *   ** * *   * ***
TX49 (L chain)      D------------CDIQM---TQTTSSLSASLGDRVTISC-RASQD-I-SNY
(SEQ ID NO: 4)
                    51                                             100
TX41 (L chain)      VNWYQQHE---GRSPTTM---IYRDDKRPD-GVPDRFSGSIDRSSN--SALLT
                    *****   *    *   **   *   *** *****    * **
TX49 (L chain)      LNWYQQKPTDG----TVKLLIYYTS-RLHSGVPSRFSGSG--SGTDYS-L-T 101                                            150
TX41 (L chain)      INNV-QTEDEADYFCQSYSSGMYI----FGGGTKL-----------
                    * *  * ** * ****     *      *******
TX49 (L chain)      ISNLEQ-EDIATYFCQQ----GNTLPWTFGGGTKLEIKRADAAPTVSIFPP 151
TX41 (L chain)      ----N                     59 identical bases
                       *
TX49 (L chain)      SSEQNH
```

[Fig. 28]

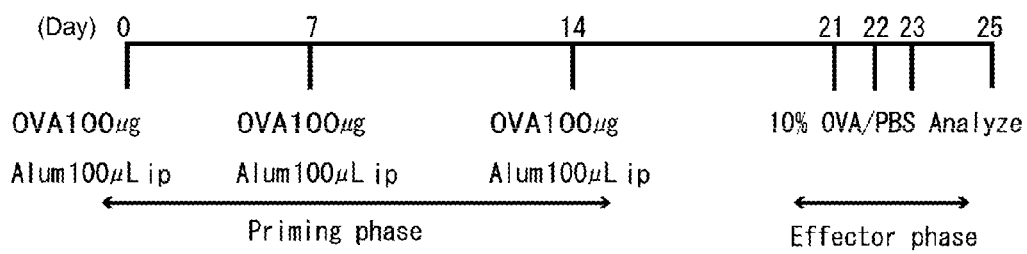

[Fig. 29]
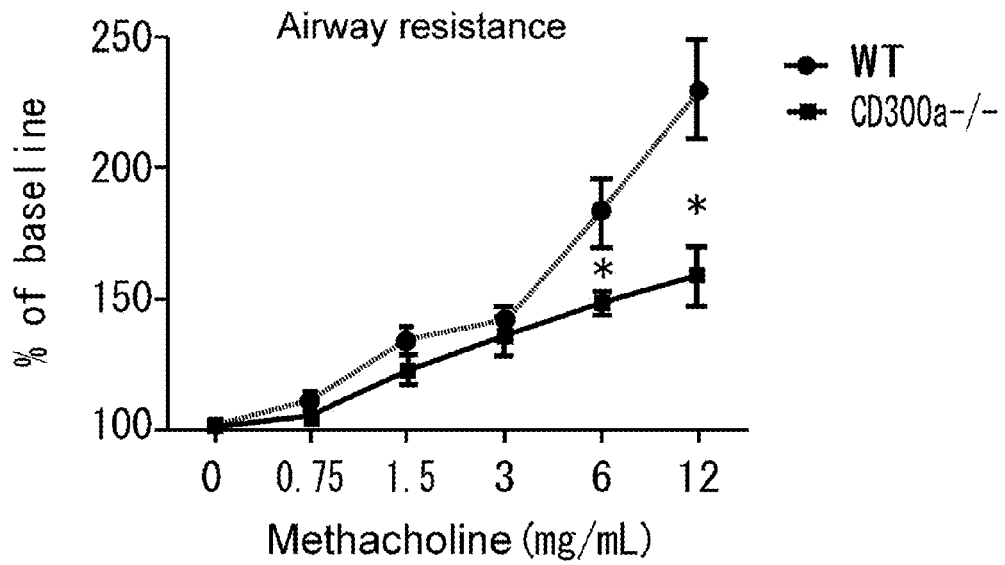
[Fig. 30]
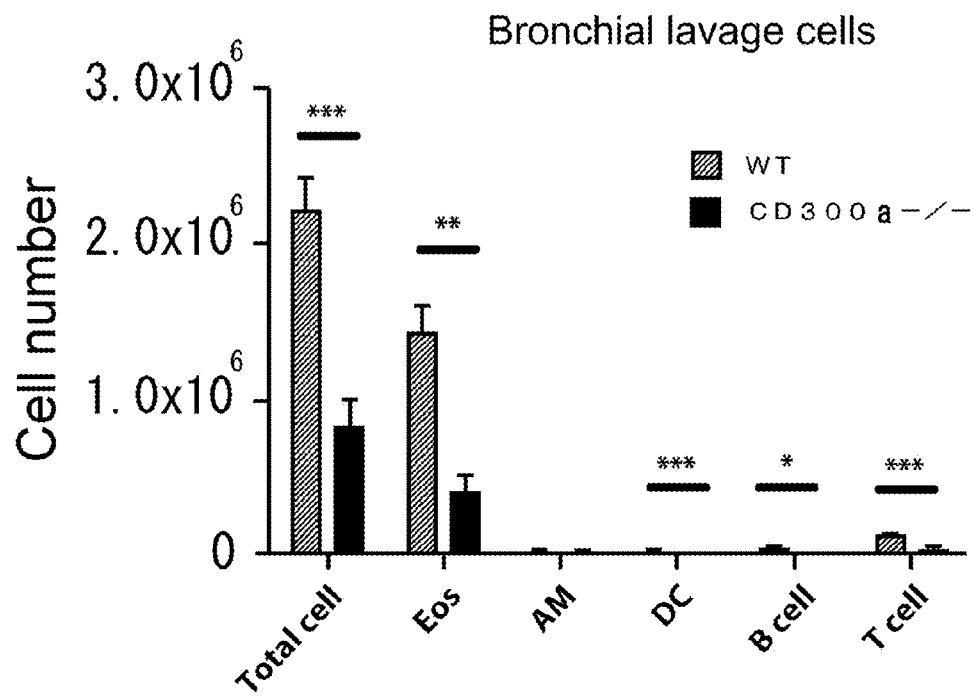

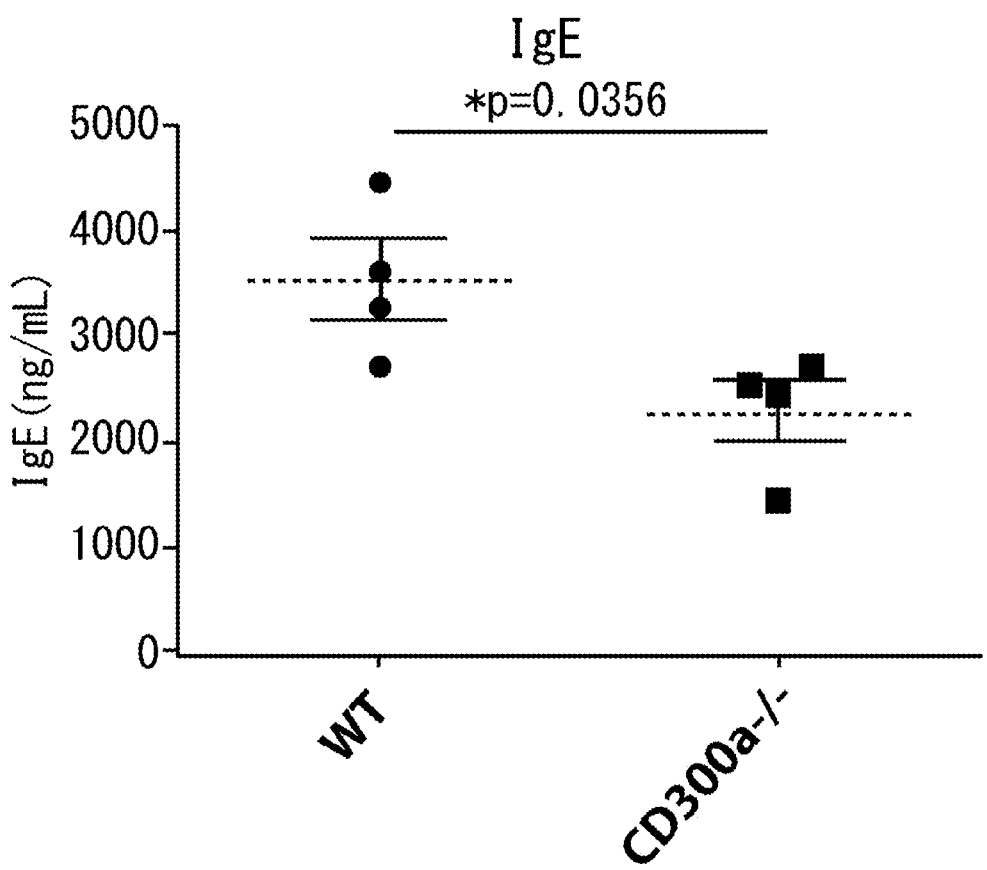
[Fig. 31]

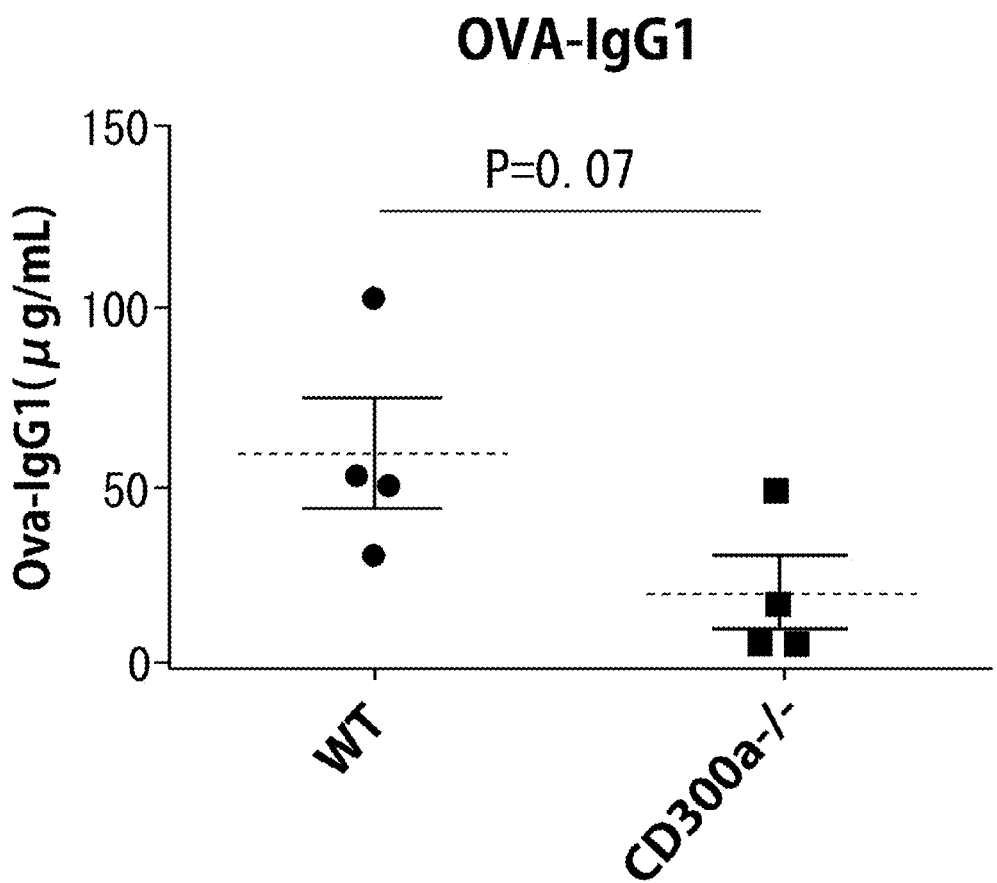
[Fig. 32]

[Fig. 33]
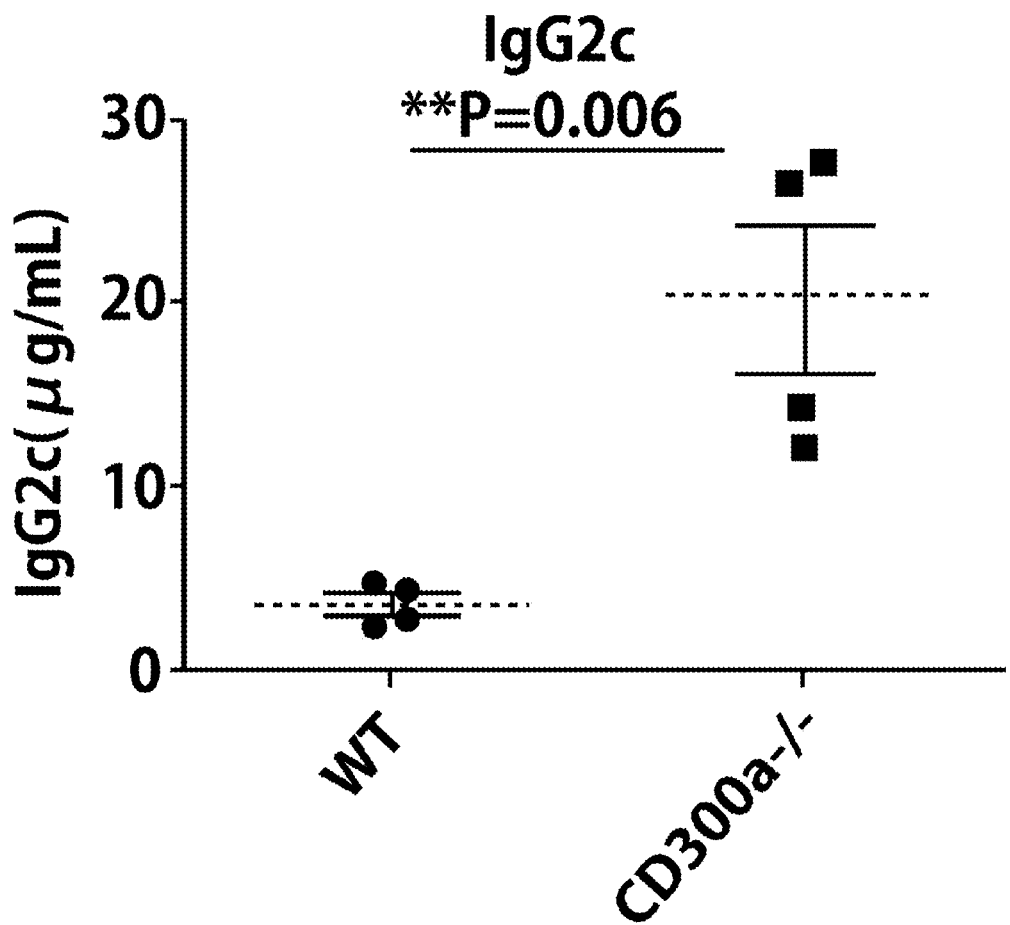

[Fig. 34]
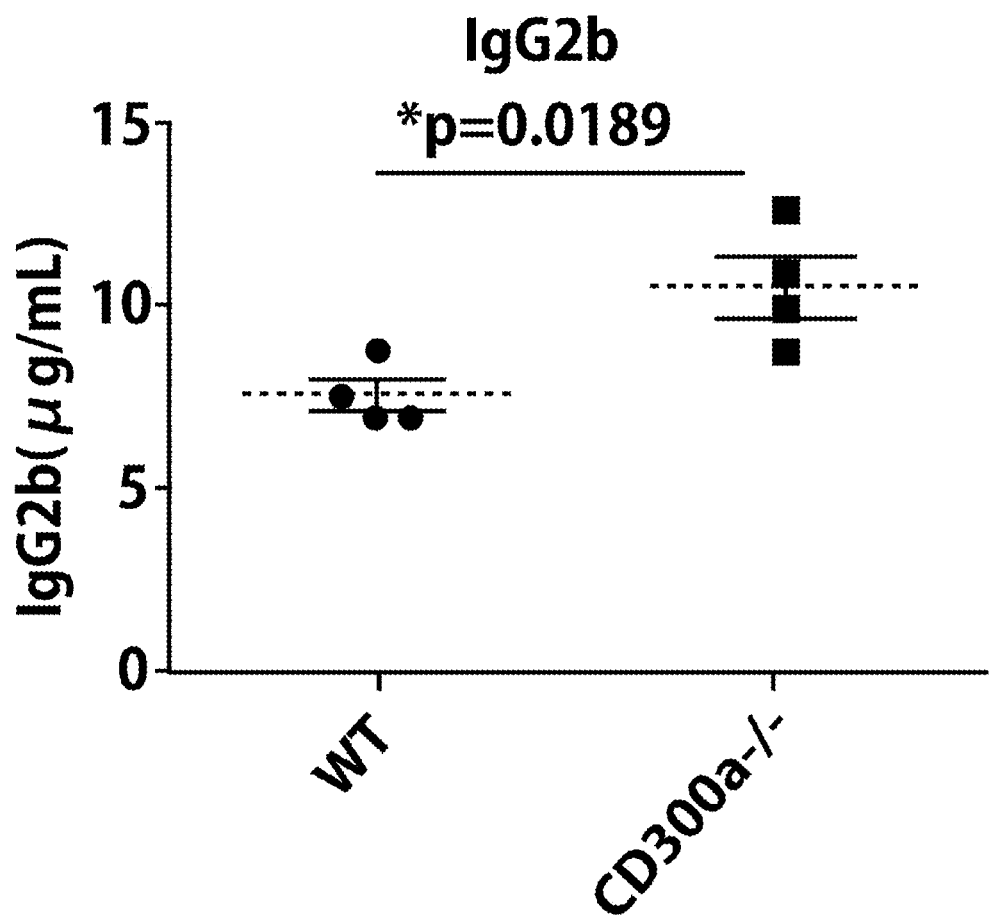

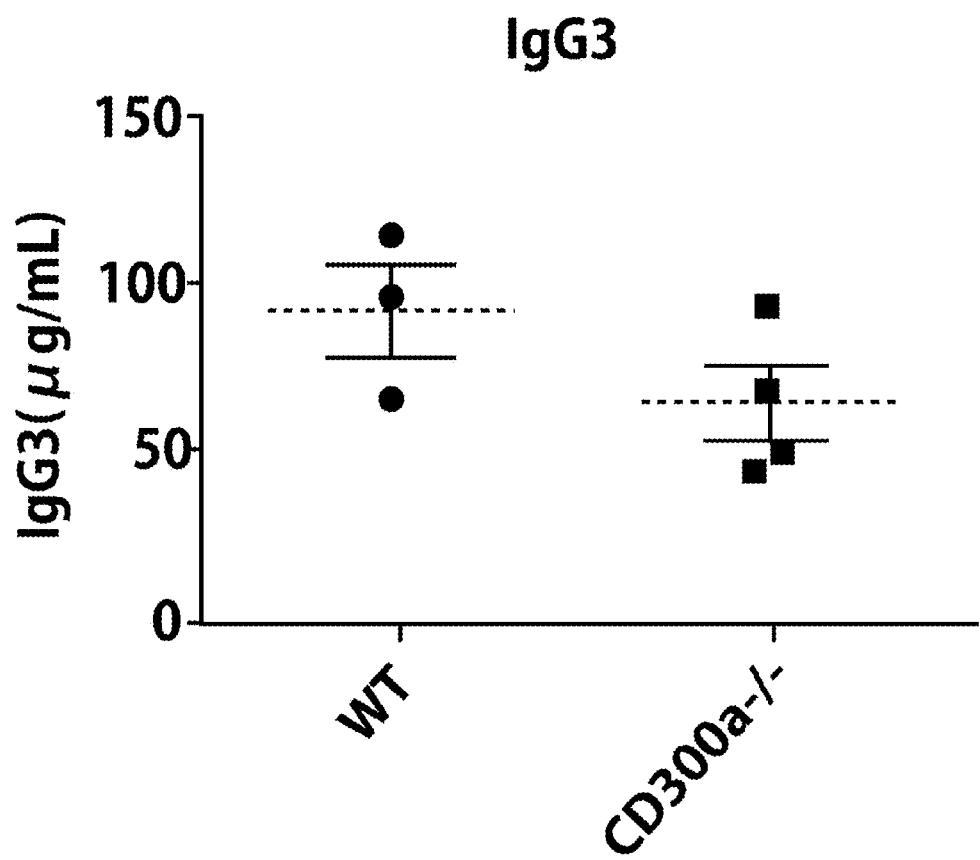

[Fig. 36]
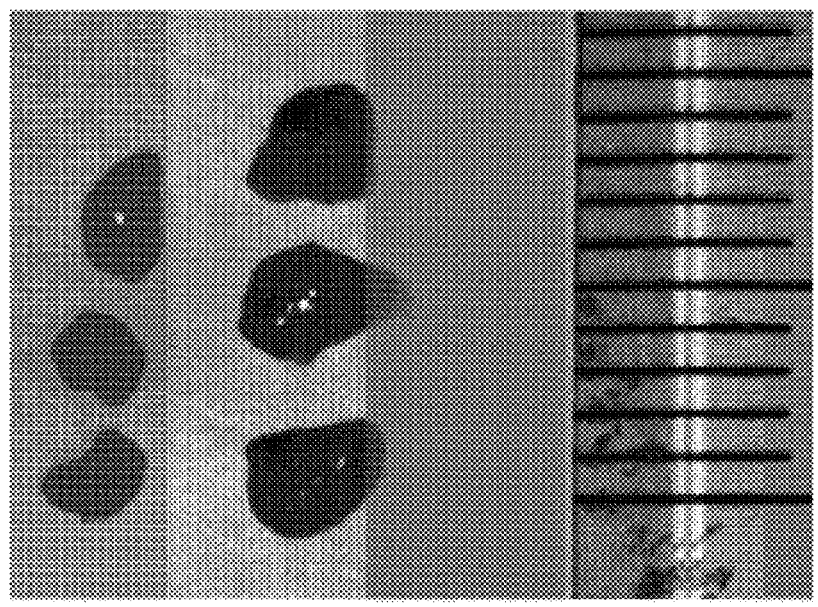

[Fig. 37]
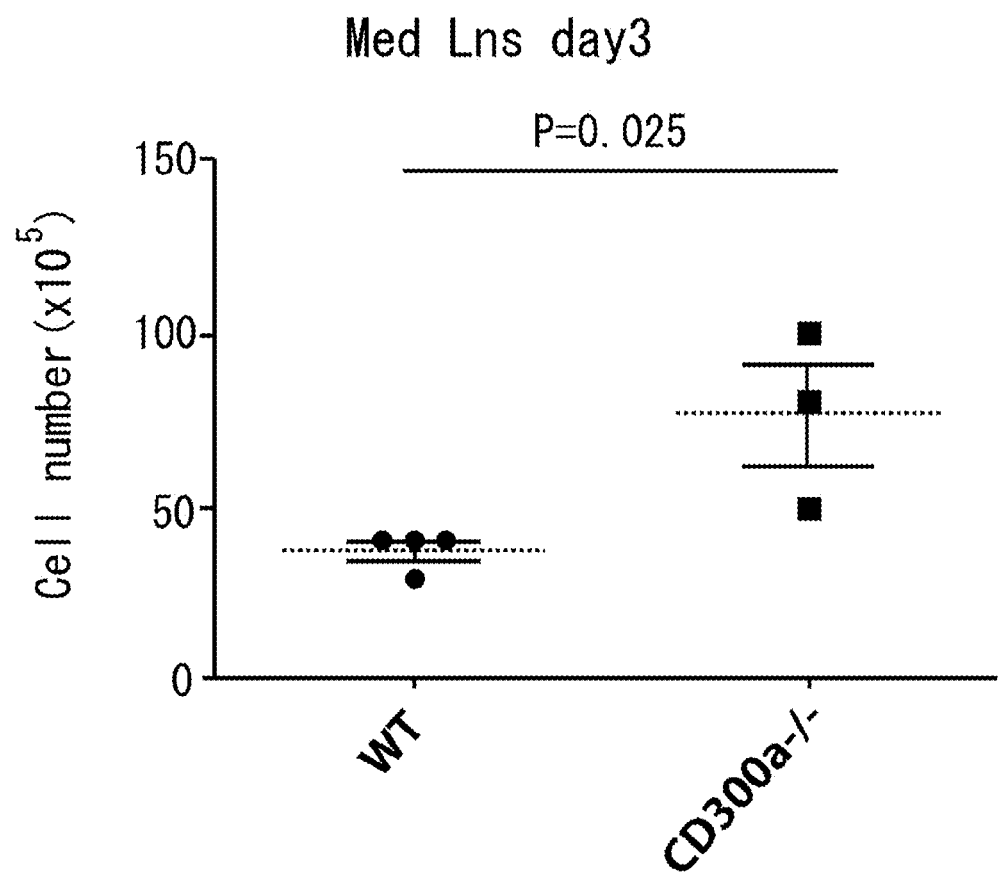

[Fig. 38]
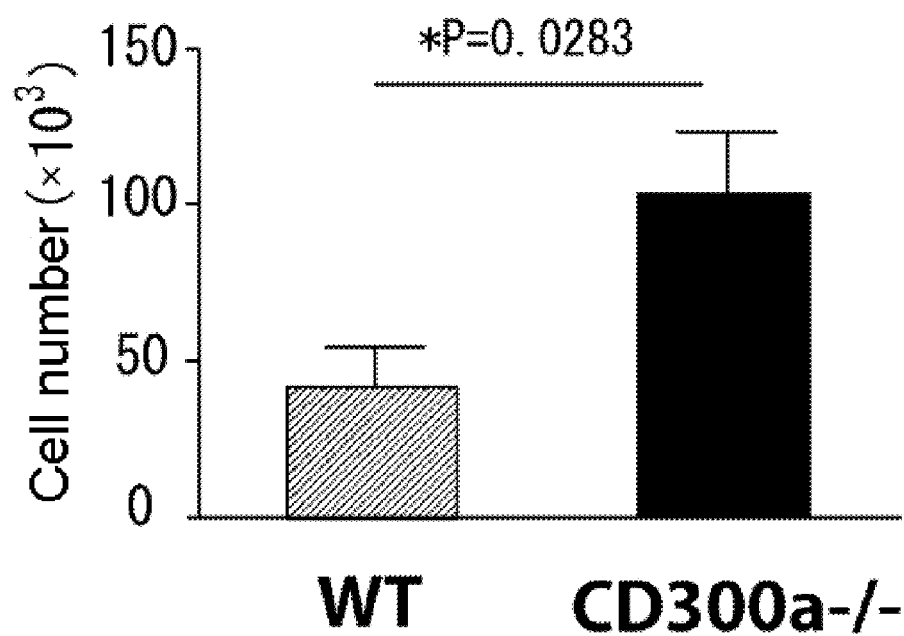

[Fig. 39]
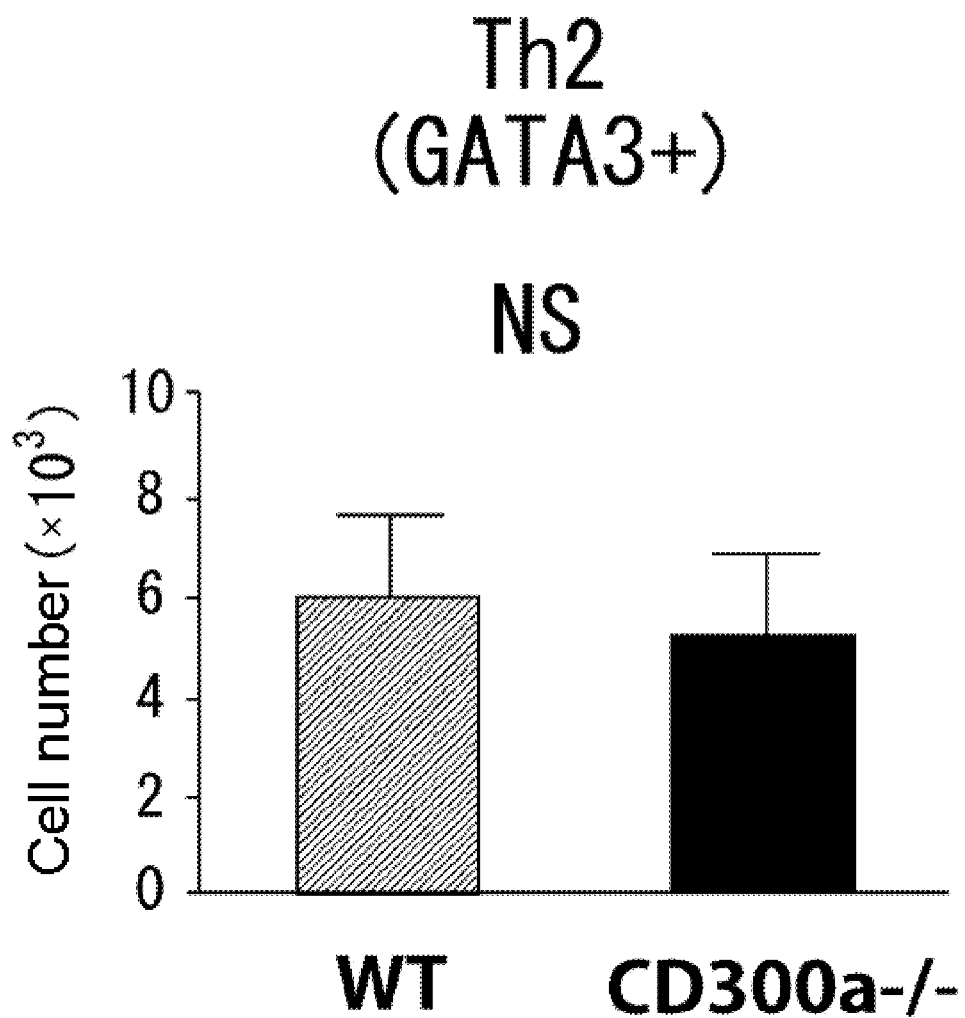

[Fig. 40]
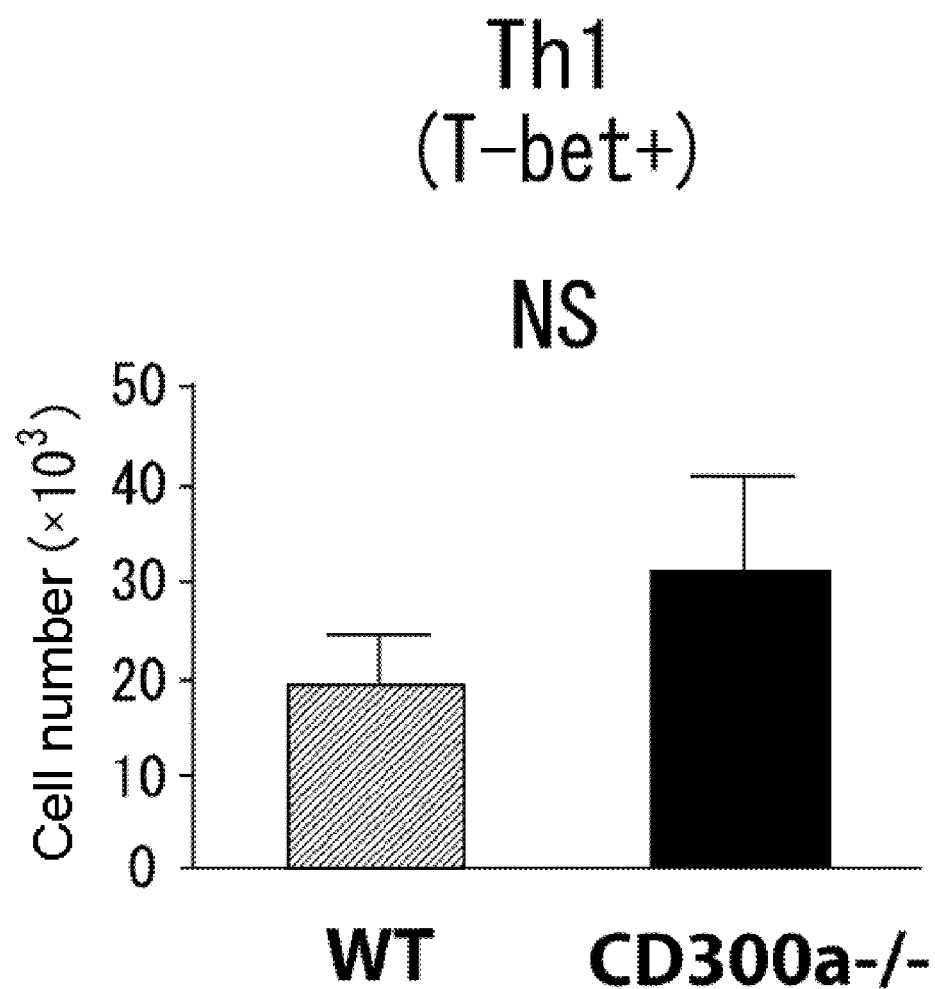

[Fig. 41]
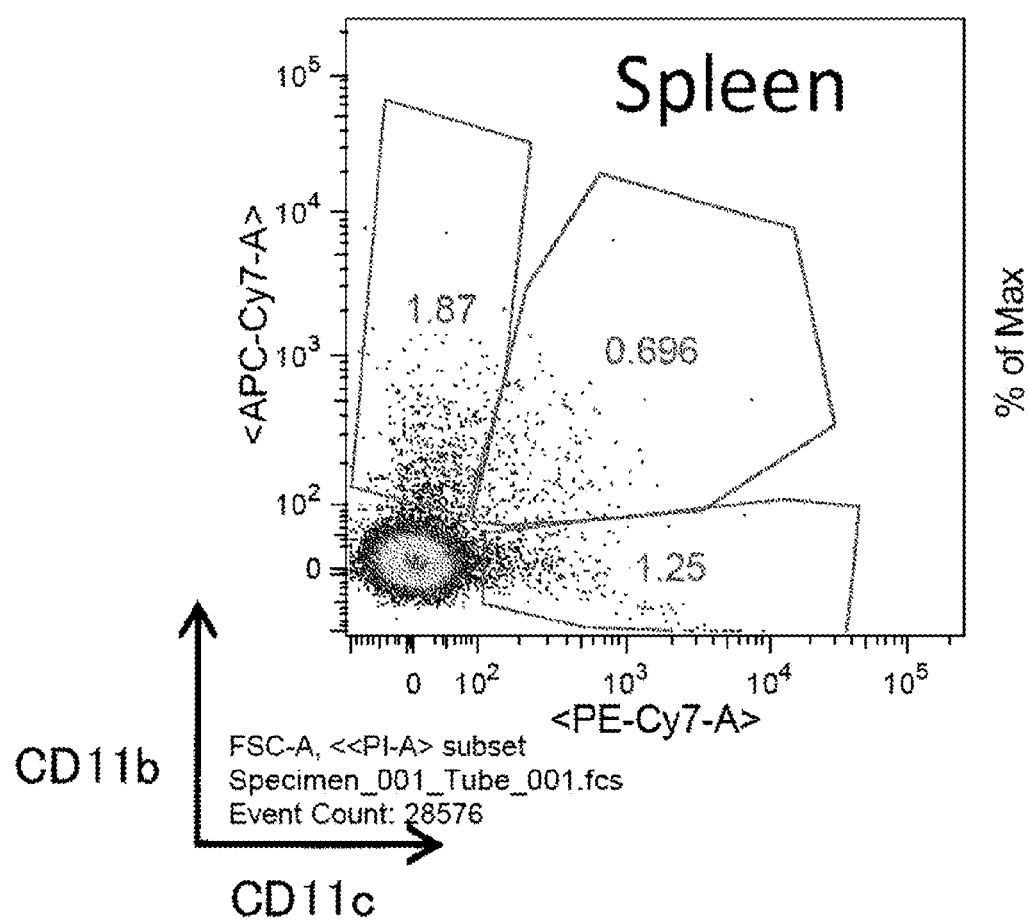

[Fig. 42]
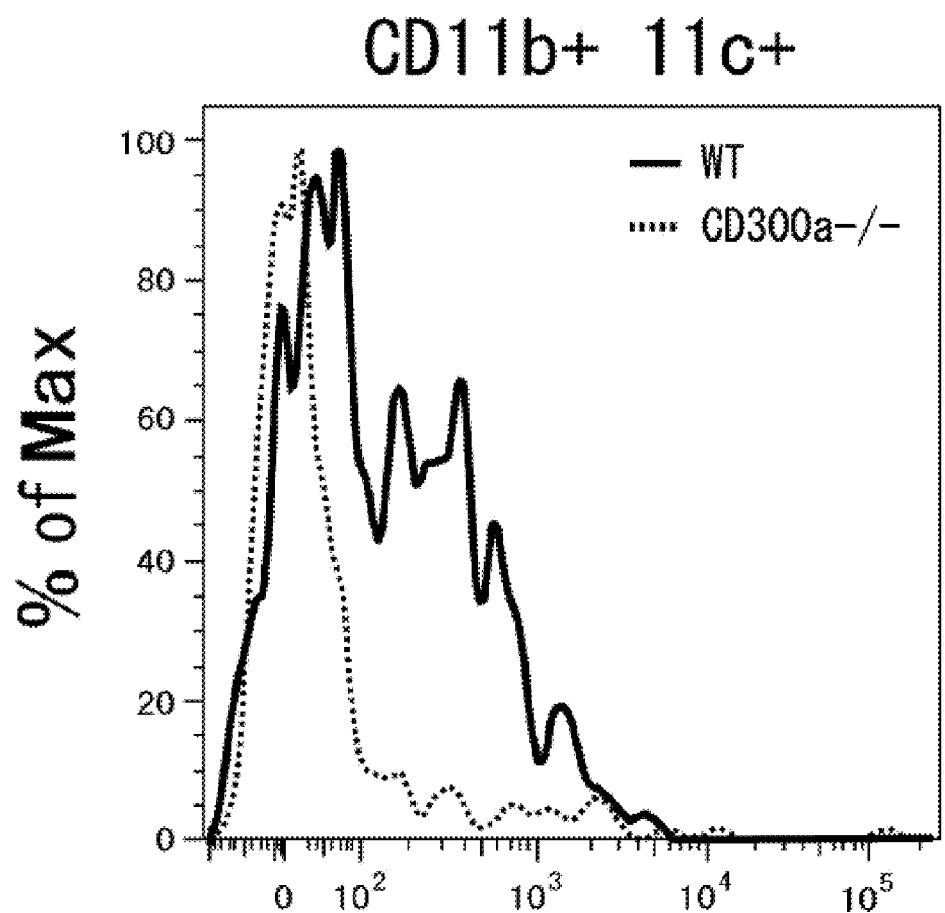

[Fig. 43]
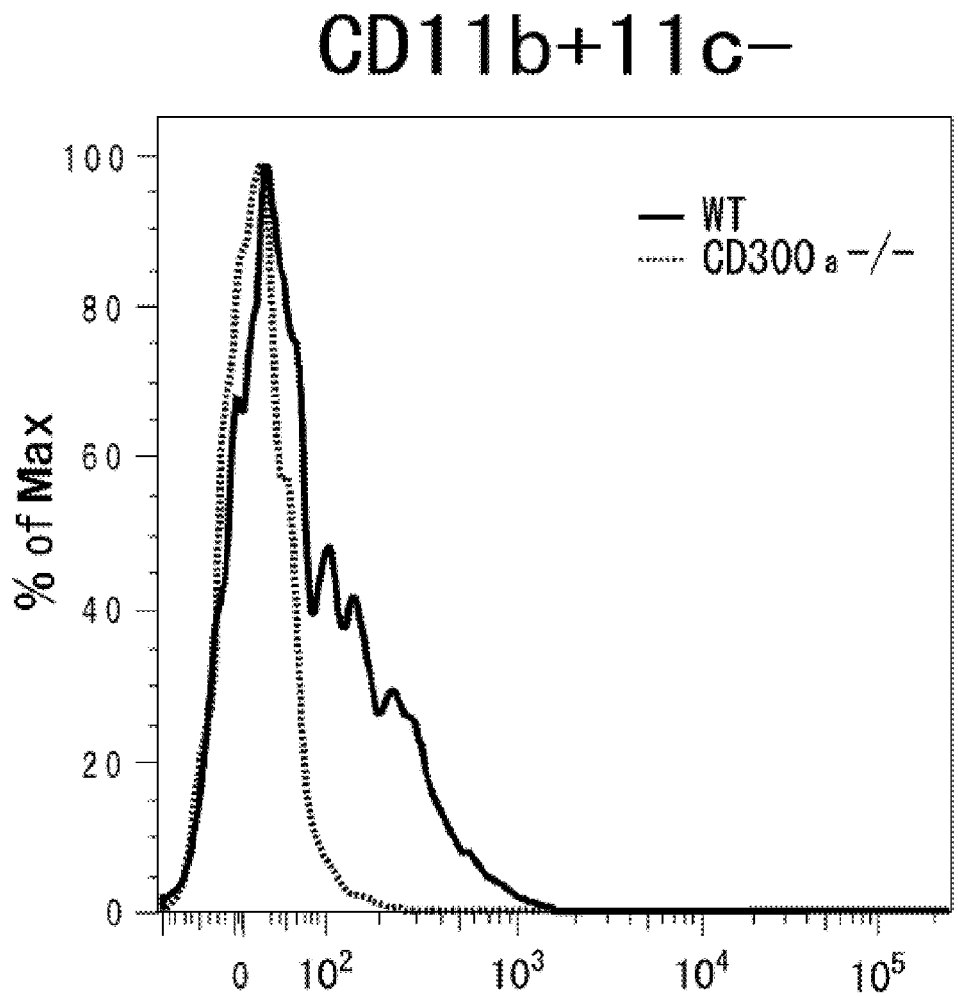

[Fig. 44]
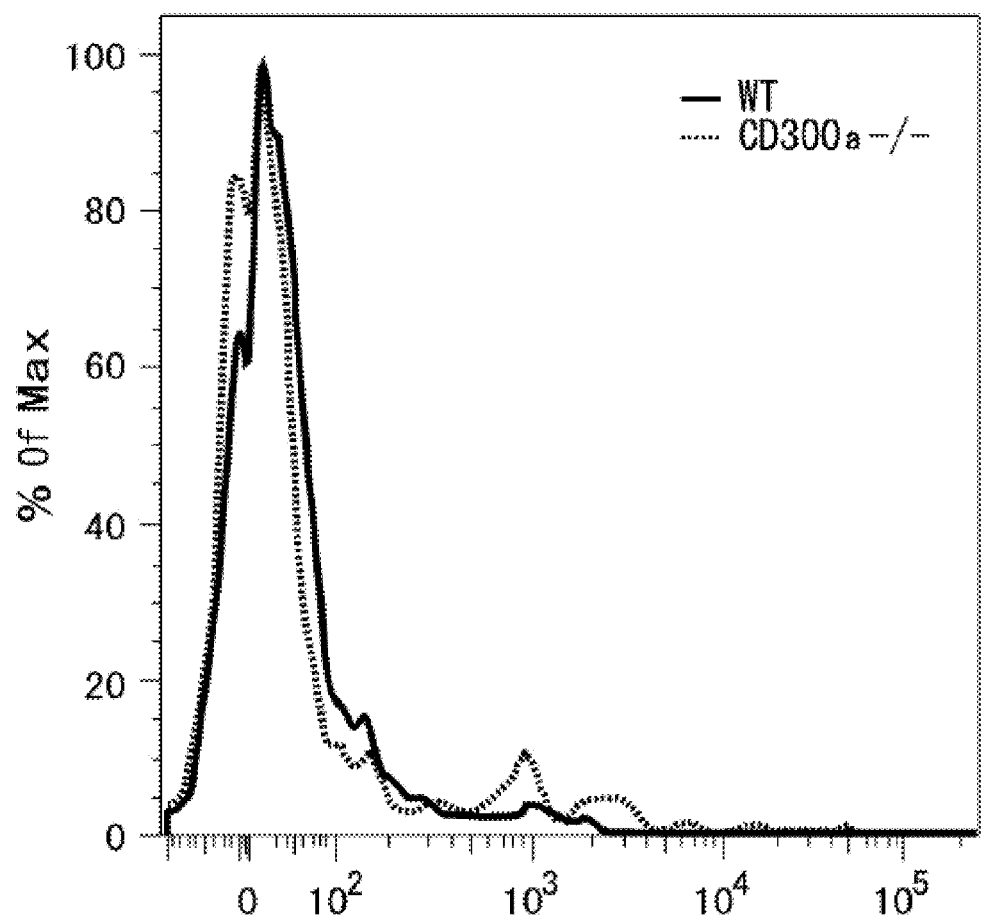

[Fig. 45]
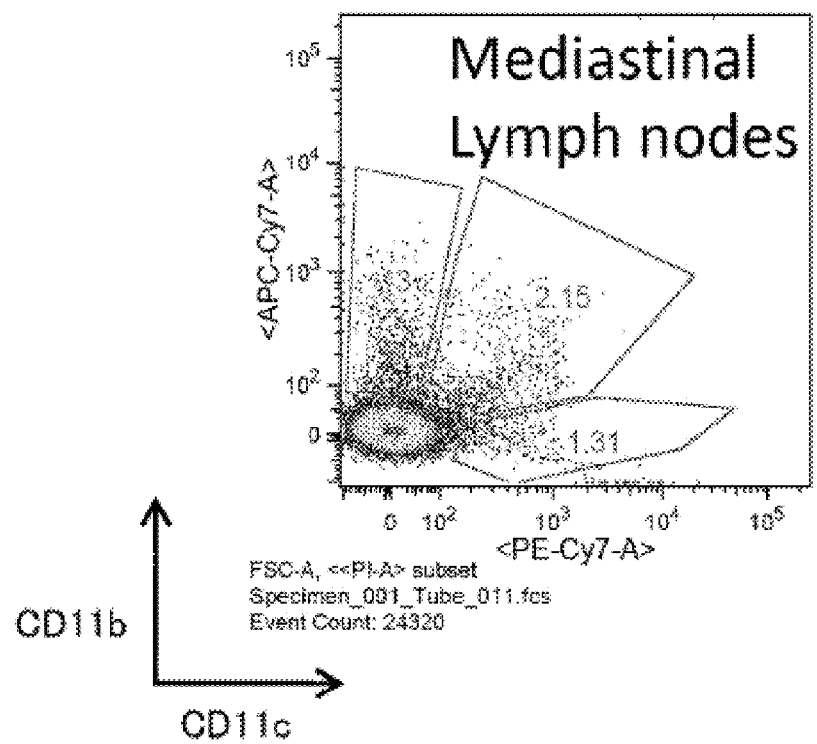

[Fig. 46]
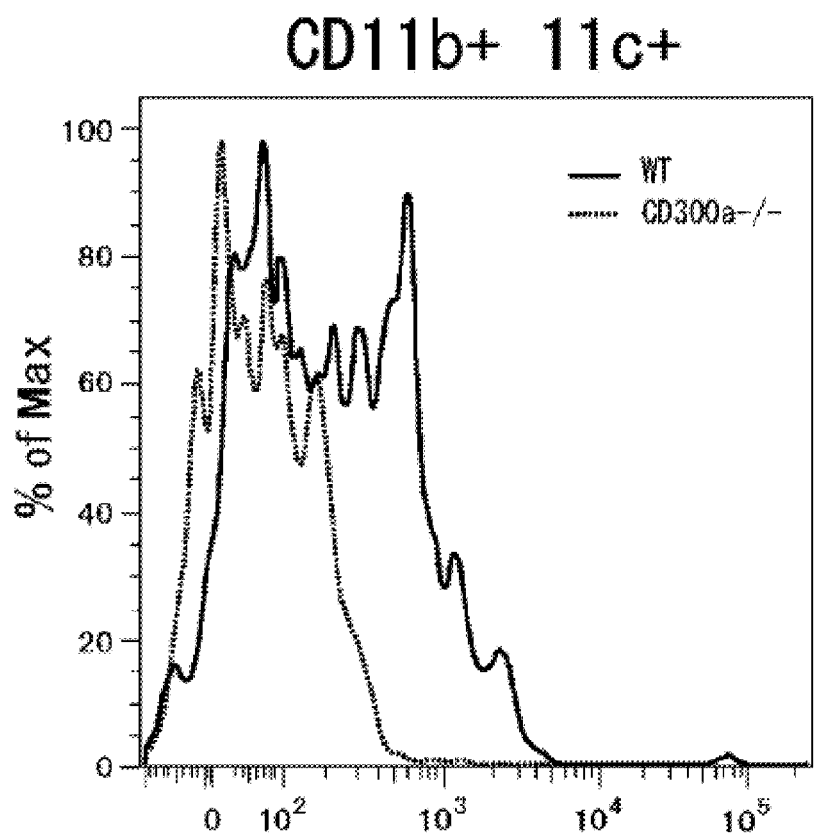

[Fig. 47]
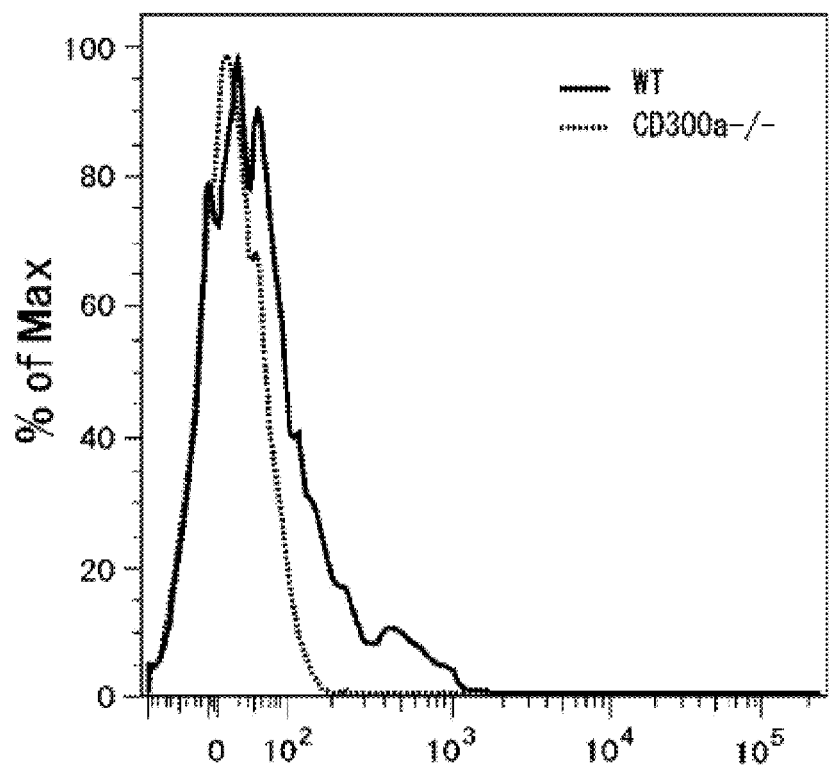

[Fig. 48]
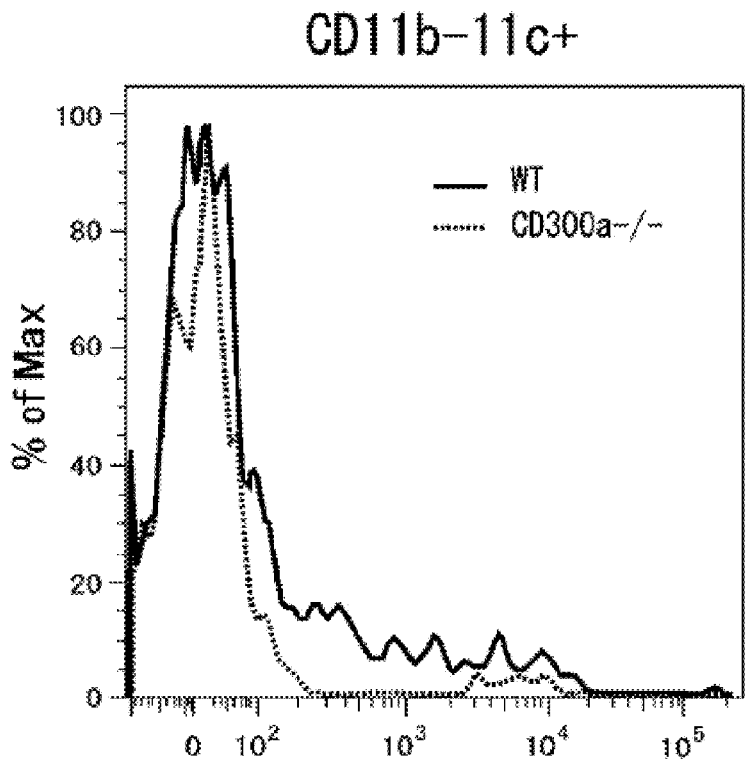
[Fig. 49]
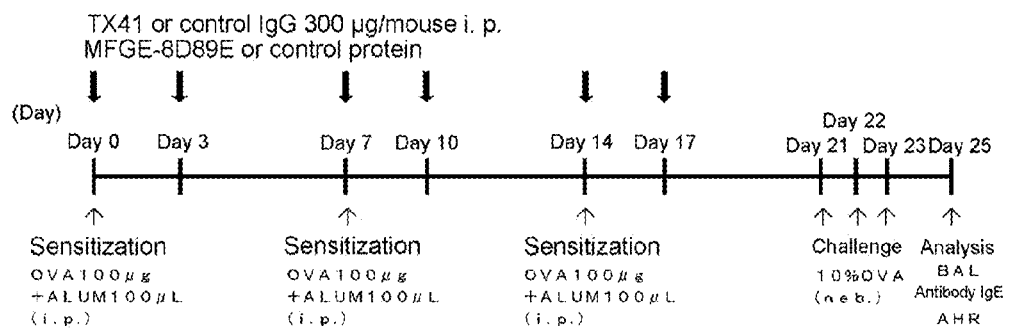

[Fig. 50]
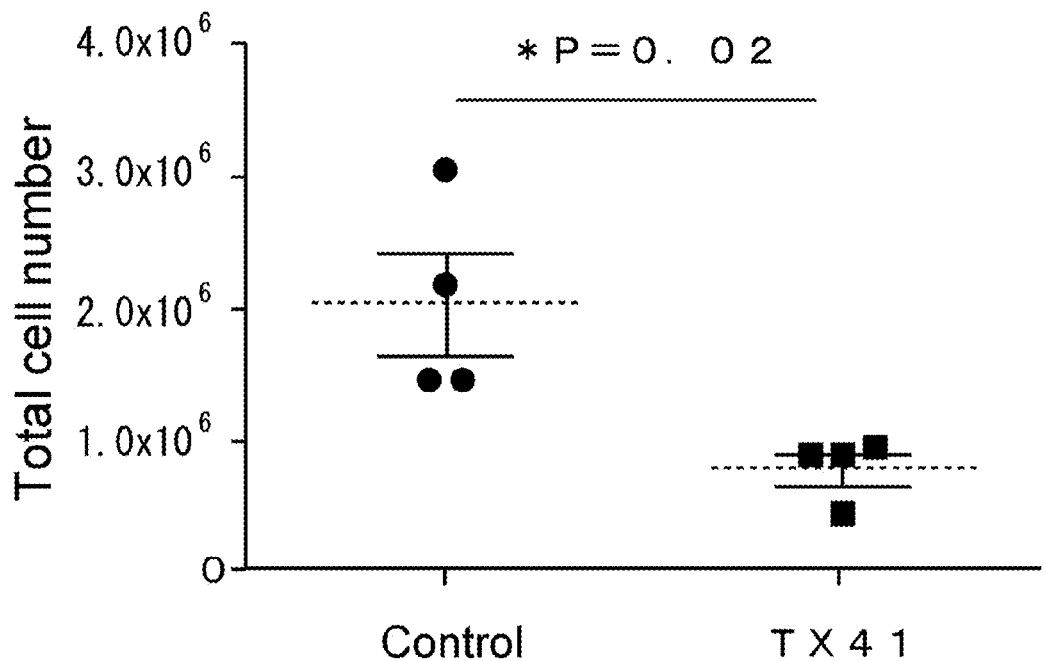
[Fig. 51]
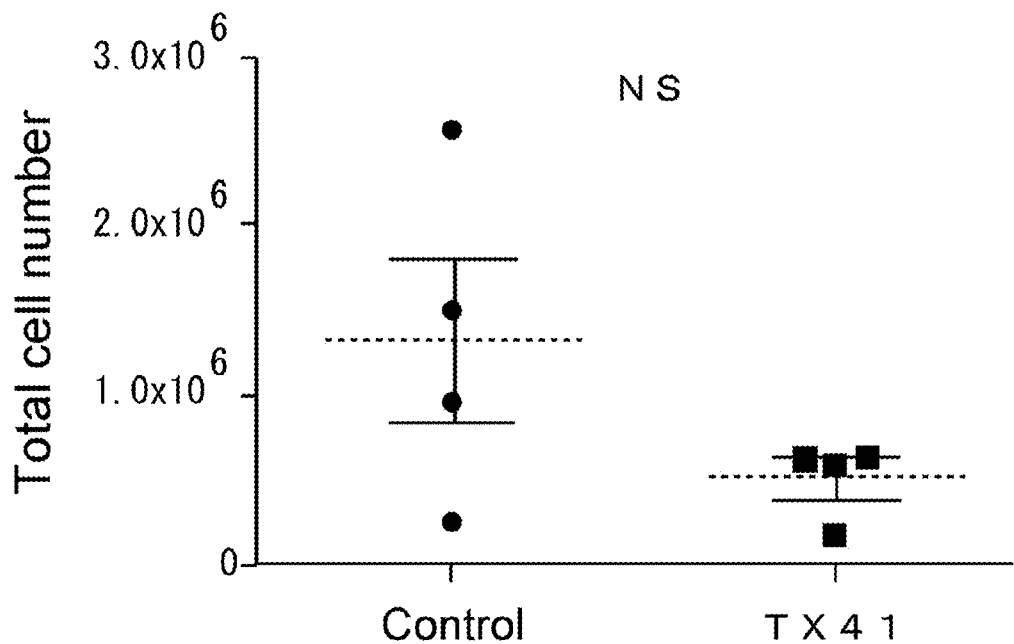

[Fig. 52]
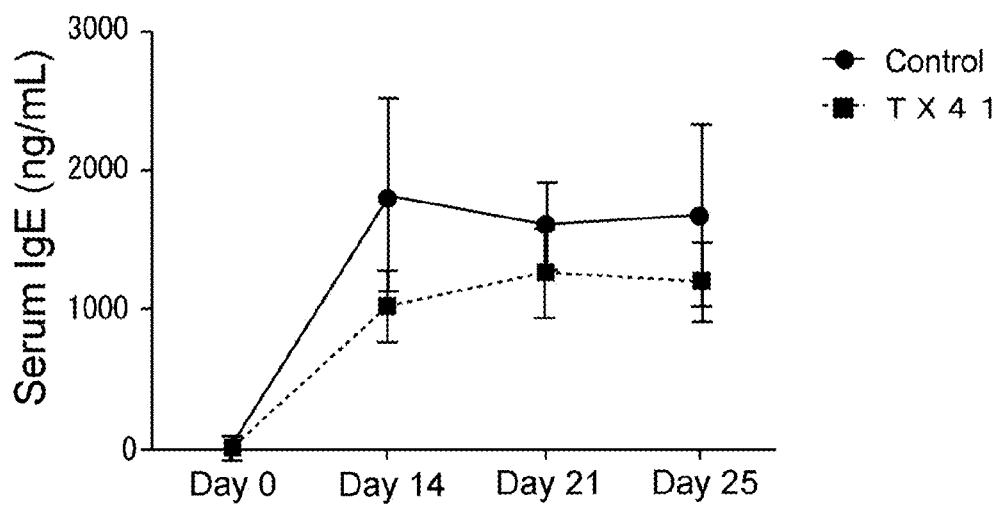
[Fig. 53]
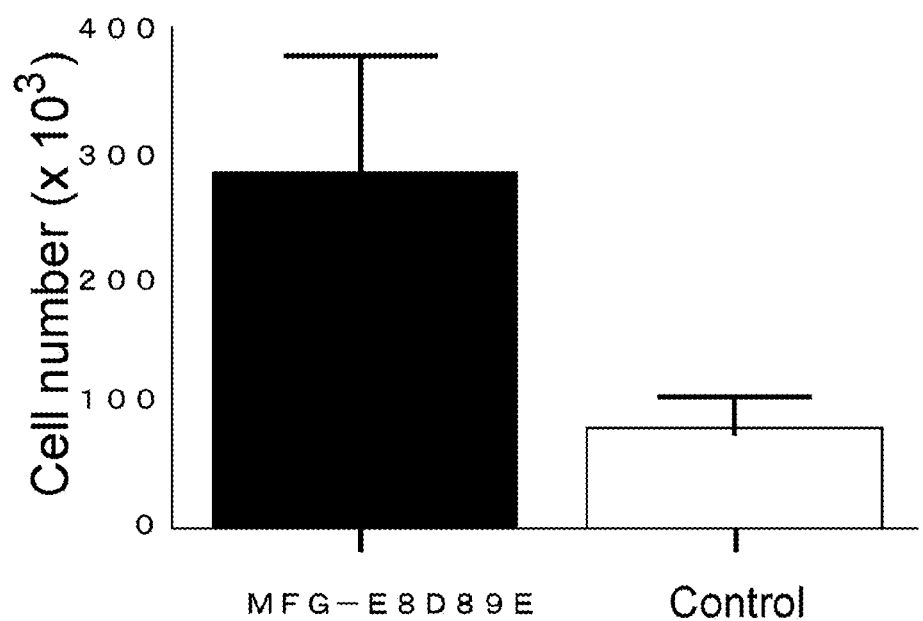

SEQUENCE LISTING

```
<160> NUMBER OF SEQ ID NOS: 4

<210> SEQ ID NO 1
<211> LENGTH: 133
<212> TYPE: PRT
<213> ORGANISM: Artificial Sequence
<220> FEATURE:
<223> OTHER INFORMATION: variable region of TX41 Heavychain

<400> SEQUENCE: 1

Ile Glu Val Lys Leu Val Glu Ser Gly Pro Gly Ile Leu Gln Pro Ser
1               5                   10                  15

Gln Thr Leu Ser Leu Thr Cys Thr Phe Ser Gly Phe Ser Leu Ser Thr
            20                  25                  30

Tyr Gly Met Gly Val Gly Trp Ile Arg Gln Pro Ser Gly Lys Gly Leu
        35                  40                  45

Glu Trp Leu Ala Asn Ile Trp Trp Asp Asp Lys Tyr Tyr Asn Pro
    50                  55                  60

Ser Leu Lys Asn Arg Leu Thr Ile Ser Lys Asp Thr Ser Asn Asn Gln
65                  70                  75                  80

Ala Phe Leu Lys Ile Thr Asn Val Asp Thr Ala Asp Thr Ala Thr Tyr
                85                  90                  95

Tyr Cys Ala Arg Pro Thr Thr Glu Gly Asp Tyr Trp Gly Gln Gly Val
            100                 105                 110
```

```
Met Val Thr Val Ser Ser Ala Glu Thr Thr Ala Pro Ser Val Tyr Pro
        115                 120                 125

Leu Ala Pro Gly Ile
    130

<210> SEQ ID NO 2
<211> LENGTH: 122
<212> TYPE: PRT
<213> ORGANISM: Artificial Sequence
<220> FEATURE:
<223> OTHER INFORMATION: variable region of TX41 LightChain

<400> SEQUENCE: 2

Asp Phe Leu Ala Phe Leu His His Leu Thr Gly Ser Cys Ala Gln Phe
1               5                   10                  15

Val Leu Thr Gln Pro Asn Ser Val Ser Thr Asn Leu Gly Ser Thr Val
            20                  25                  30

Lys Leu Ser Cys Lys Arg Ser Thr Gly Asn Ile Gly Ser Asn Tyr Val
        35                  40                  45

Asn Trp Tyr Gln Gln His Glu Gly Arg Ser Pro Thr Thr Met Ile Tyr
    50                  55                  60

Arg Asp Asp Lys Arg Pro Asp Gly Val Pro Asp Arg Phe Ser Gly Ser
65                  70                  75                  80

Ile Asp Arg Ser Ser Asn Ser Ala Leu Leu Thr Ile Asn Asn Val Gln
                85                  90                  95

Thr Glu Asp Glu Ala Asp Tyr Phe Cys Gln Ser Tyr Ser Ser Gly Met
            100                 105                 110

Tyr Ile Phe Gly Gly Gly Thr Lys Leu Asn
        115                 120

<210> SEQ ID NO 3
<211> LENGTH: 141
<212> TYPE: PRT
<213> ORGANISM: Artificial Sequence
<220> FEATURE:
<223> OTHER INFORMATION: variable region of TX49 Heavychain

<400> SEQUENCE: 3

Val Ile Glu Val Gln Leu Gln Gln Ser Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser Tyr Trp Met Gln Trp Val Lys Gln Arg Pro Gly Gln Gly Leu Glu
        35                  40                  45

Trp Ile Gly Glu Ile Asp Pro Ser Asp Ser Tyr Thr Asn Tyr Asn Gln
    50                  55                  60

Lys Phe Lys Gly Lys Ala Thr Leu Thr Val Asp Thr Ser Ser Ser Thr
65                  70                  75                  80

Thr Tyr Met Gln Leu Ser Ser Leu Thr Ser Glu Asp Ser Ala Val Tyr
                85                  90                  95

Tyr Cys Ala Arg Trp Gly Met Ala Tyr Gly Thr Ser Ser Tyr Trp Tyr
            100                 105                 110

Phe Asp Val Trp Gly Thr Gly Thr Val Thr Val Ser Ser Ala Lys
        115                 120                 125

Thr Thr Pro Pro Ser Val Tyr Pro Leu Ala Pro Gly Ile
    130                 135                 140

<210> SEQ ID NO 4
```

```
<211> LENGTH: 128
<212> TYPE: PRT
<213> ORGANISM: Artificial Sequence
<220> FEATURE:
<223> OTHER INFORMATION: variable region of TX49 Lightchain

<400> SEQUENCE: 4

Asp Cys Asp Ile Gln Met Thr Gln Thr Thr Ser Ser Leu Ser Ala Ser
1               5                   10                  15

Leu Gly Asp Arg Val Thr Ile Ser Cys Arg Ala Ser Gln Asp Ile Ser
            20                  25                  30

Asn Tyr Leu Asn Trp Tyr Gln Gln Lys Pro Asp Gly Thr Val Lys Leu
        35                  40                  45

Leu Ile Tyr Tyr Thr Ser Arg Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Pro Trp Thr Phe Gly Gly Gly Thr Lys Leu Glu Ile Lys Arg Ala Asp
            100                 105                 110

Ala Ala Pro Thr Val Ser Ile Phe Pro Pro Ser Ser Glu Gln Asn His
        115                 120                 125
```

MEDICAMENT COMPRISING ACTIVITY MODULATOR FOR CD300A-EXPRESSING CELL ASSOCIATED WITH ALLERGIC DISEASE, CD300A GENE-DEFICIENT MOUSE, AND USE OF ACTIVITY MODULATOR FOR CD300A-EXPRESSING CELL

TECHNICAL FIELD

The present invention relates to a medicament containing an activity modulator for a CD300a-expressing cell, which is associated with allergic diseases, and use of a CD300a gene-deficient mouse and the activity modulator for a CD300a-expressing cell.

BACKGROUND ART

Invasion of a pathogen (bacterium, virus, parasite or the like) into a host (human body or animal body) or generation of an endogenous inflammatory substance causes inflammatory reactions in which, for example, temporary contraction of arteriolae occurs at the site of invasion of the pathogen or the site of generation of the inflammatory substance, and expansion and hyperemia then occur, leading to local slowness of blood flow at the site of invasion of the pathogen or the site of generation of the inflammatory substance.

This causes adhesion of leukocytes to the vascular wall, and chemical mediators released from various immunocytes then act on the leukocytes to cause them to pass through the vascular wall by amoeboid movement and to allow their migration. Known examples of the chemical mediators include histamine, serotonin and lymphokines. Mast cells, which produce and release histamine and serotonin, are a type of lymphocytes that play a central role in the inflammatory reaction. Similarly to mast cells, macrophages also produce and release chemical mediators such as TNF.

The leukocytes whose migration was induced by the inflammatory reaction are attracted by the pathogen or the like, and this causes elimination (clearance) of the pathogen from the body by humoral immunity accompanied by antigen-antibody reaction and by cell-mediated immunity in which cytotoxic T cells and the like are involved, resulting in prevention of the spread of infection. Thus, the inflammatory reaction, and immune reactions that occur based on the inflammatory reaction, are extremely important for maintaining homeostasis of a living body.

On the other hand, the inflammatory reaction causes not only the biological defense described above, but also adverse signs/symptoms such as flare, fever, swelling, pain and dysfunction. Specific examples of such symptoms include allergic diseases, and various types of acute and chronic inflammations. Also in autoimmune diseases, in which the absence of immunological tolerance causes an autoimmune response, tissue injury occurs due to the inflammatory reaction.

That is, for prevention of a disease accompanied by the inflammatory reaction, it is important to kill the pathogen that causes the inflammatory reaction using antibiotics (antimicrobial agents), or to administer an agent that increases the immune function in the living body to eliminate the pathogen before an excessive inflammatory reaction occurs.

On the other hand, known examples of methods for amelioration or treatment of a disease accompanied by the inflammatory reaction include suppression of inflammation by administration of an agent (anti-inflammatory agent) that decreases excessively activated immune function by, for example, suppression of release of chemical mediators.

For example, Patent Document 1 discloses, as an immunostimulant, an activating agent for the function of dendritic cells, which are antigen-presenting cells responsible for activation of various immunocytes. More specifically, the agent comprises as an effective component(s) at least one branched chain amino acid selected from isoleucine, leucine and valine.

Patent Document 2 discloses, as an anti-inflammatory agent, an agent comprising the SPARC (Secreted protein which is acidic and rich in cystein) peptide and a pharmaceutical carrier.

It is known that a group of receptor molecules called MAIR (Myeloid Associated Ig like Receptors) are expressed on the cell membrane of myeloid (bone marrow) cells responsible for natural immunity (Non-patent Document 1). Among these, MAIR-I, which is also known as CD300a (also referred to as "LMIR1" or "CLM-8"), is expressed in macrophages, mast cells, granulocytes (neutrophils) and dendritic cells, and known to be an inhibitory receptor that associates with phosphatase via the ITIM (Immunoreceptor tyrosine-based inhibitory motif) sequence in the intracellular domain to transmit an inhibitory signal (Non-patent Document 2). However, the ligand for this receptor is unknown, and the receptor has been the so-called orphan receptor.

Atopic dermatitis is caused by entrance of an allergic substance (antigen) into the body followed by production of periostin due to stimulation by substances (interleukins 4 and 13) secreted from activated immunocytes, and then binding of the periostin to another protein "integrin" on the surface of keratinocytes in the skin, to cause inflammation.

The binding of periostin to integrin causes production of other inflammation-inducing substances, and the symptoms continue even in the absence of the antigen, resulting in chronicity. It has been shown, by an experiment using mice, that inhibition of binding of periostin to integrin using an inhibitor prevents occurrence of atopic dermatitis (Non-patent Document 3).

Although the major cause of atopic dermatitis has become evident, further elucidation of the pathology of atopic dermatitis, analysis of association of atopic dermatitis with other inflammatory diseases, and medicaments for atopic dermatitis that can be used in combination with the above inhibitor, are demanded.

Bronchial asthma is a respiratory disease in which bronchial inflammation triggered by an allergic reaction or infection with a bacterium or virus becomes chronic to thereby cause increased airway hyperresponsiveness and reversible airway narrowing, leading to symptoms such as attacks of wheezing, and cough. Further, bronchial asthma is said to be caused by the combination of airway hyperresponsiveness, allergic diathesis and environment. Recurrent symptoms such as wheezing, apnea, chest tightness and cough occur especially at night or in the early morning.

A number of cells and cellular components, especially mast cells, eosinophils, T-lymphocytes, macrophages, neutrophils and epithelial cells play roles in inflammation of the airway. Inflammation is associated with plasma exudation, edema, smooth muscle enlargement, mucus plugging, and epithelial changes. Further, inflammation causes associated increases in bronchial hyperresponsiveness to various stimuli.

Inflammation of the airway induces atrophy of airway smooth muscle, microvascular rupture and bronchial hyperresponsiveness. As the responsiveness of the airway increases, the symptoms become more severe and continuous, and daily variation of the pulmonary function increases. The mechanism of involvement of airway inflammation in the bronchial responsiveness is unknown, and tools useful for elucidation of the pathology of asthma, and medicaments and the like have been demanded.

PRIOR ART DOCUMENTS

Patent Documents

[Patent Document 1] JP 2007-297379 A
[Patent Document 2] JP 2011-516609 A

Non-Patent Documents

[Non-patent Document 1] Yotsumoto et al., J Exp Med 198 (2), 223-233, 2003
[Non-patent Document 2] Okoshi Y et al., Int Immunol., 17, 65-72, 2005.
[Non-patent Document 3] Miho Masuoka et. al., J Clin Invest. 2012; doi:10.1172/JCI58978

SUMMARY OF THE INVENTION

Problems to be Solved by the Invention

An object of the present invention is to provide a medicament for allergic diseases, and a tool and the like useful for pathology analysis of allergic diseases.

Means for Solving the Problems

In order to elucidate the ligand of CD300a and the function of CD300a, the present inventors intensively studied to discover the following.
(i) The ligand of CD300a is phosphatidyl serine (PS).
(ii) Binding of PS to CD300a on mast cells and the like promotes inhibitory signal transduction via CD300a, and activation of the mast cells and the like are also suppressed thereby.
(iii) Inhibition of binding of CD300a on mast cells and the like to PS by coexistence of a phosphatidyl serine-binding substance or CD300a-binding substance suppresses inhibitory signal transduction of CD300a, and the active state of mast cells and the like is maintained.
(iv) Through the suppression or maintenance of the active state, allergic diseases and the like can be treated.
(v) CD300a gene-deficient mice can be a tool for performing pathology analysis of allergic diseases, and screening of effective components of medicaments.

The present invention was attained based on these discoveries, and provides, for example, the inventions described in [1] to [9] below.

[1] A medicament for treatment or prophylaxis of an allergic disease, the medicament comprising as an effective component an activity modulator for suppressing inhibitory signal transduction of a CD300a-expressing myeloid cell, the activity modulator comprising a substance that inhibits binding of CD300a to phosphatidyl serine.

[2] The medicament according to [1], wherein the substance that inhibits binding of CD300a to phosphatidyl serine is a phosphatidyl serine-binding substance.

[3] The medicament according to [2], wherein the phosphatidyl serine-binding substance is at least one selected from the group consisting of MFG-E8, MFG-E8 mutants (D89E MFG-E8), T cell immunoglobulin, soluble TIM-1, soluble TIM-4, soluble stabilin, and soluble integrin $\alpha v\beta 3$.

[4] The medicament according to [1], wherein the substance that inhibits binding of CD300a to phosphatidyl serine is a CD300a-binding substance.

[5] The medicament according to [4], wherein the CD300a-binding substance is an anti-human CD300a antibody comprising: an H-chain variable region having the amino acid sequence of SEQ ID NO:3 or an amino acid sequence that is the same as the amino acid sequence except that 1, 2, 3, 4, or 5 amino acid(s) is/are substituted, added, inserted and/or deleted; and an L-chain variable region having the amino acid sequence of SEQ ID NO:4 or an amino acid sequence that is the same as the amino acid sequence except that 1, 2, 3, 4, or 5 amino acid(s) is/are substituted, added, inserted and/or deleted.

[6] The medicament according to [4], wherein the CD300a-binding substance is an anti-mouse CD300a antibody comprising: an H-chain variable region having the amino acid sequence of SEQ ID NO:1 or an amino acid sequence that is the same as the amino acid sequence except that 1, 2, 3, 4, or 5 amino acid(s) is/are substituted, added, inserted and/or deleted; and an L-chain variable region having the amino acid sequence of SEQ ID NO:2 or an amino acid sequence that is the same as the amino acid sequence except that 1, 2, 3, 4, or 5 amino acid(s) is/are substituted, added, inserted and/or deleted.

[7] The medicament according to any one of [1] to [6], wherein the allergic disease is atopic dermatitis or asthma.

[8] Use of a CD300a gene-deficient mouse for carrying out pathology analysis of an allergic disease, or for screening of a possible candidate substance for an effective component of a therapeutic agent or prophylactic agent for the disease, wherein the CD300a gene-deficient mouse is used as a model mouse in which the allergic disease is hardly induced after administration of a substance that induces the allergic disease.

[9] Use of an activity modulator for promoting inhibitory signal transduction of a CD300a-expressing myeloid cell, the activity modulator comprising a substance that promotes binding of CD300a to phosphatidyl serine, as a comparative analysis tool for carrying out pathology analysis of an allergic disease, or for screening of a possible candidate substance for an effective component of a therapeutic agent or prophylactic agent for the disease.

As other aspects of the inventions described above, the following inventions are provided.

Another aspect of the invention of [1] provides a method for treatment or prophylaxis of an allergic disease, which method comprises inhibiting binding of CD300a to phosphatidyl serine to thereby suppress inhibitory signal transduction of a CD300a-expressing myeloid cell. This method is applicable either in vivo or ex vivo/in vitro, and, in cases of in vivo application, the species of organism may be either human or non-human (e.g., a mammal such as mouse).

Still another aspect of the invention of [1] provides use of an activity modulator that inhibits binding of CD300a to phosphatidyl serine to thereby suppress inhibitory signal transduction of a CD300a-expressing myeloid cell, in production of a medicament for treatment or prophylaxis of an allergic disease.

Effect of the Invention

The present invention enables production of a medicament for treatment or prophylaxis of an allergic disease, which medicament comprises as an effective component an activity modulator for inhibiting inhibitory signal transduction of a CD300a-expressing cell. The present invention also enables use of a CD300a gene-deficient mouse or the like as a model mouse or the like useful for pathology analysis, treatment, or the like of an allergic disease.

BRIEF DESCRIPTION OF THE DRAWINGS

FIG. 1 shows the results of flow cytometry analysis obtained in Reference Example 1A.

FIG. 2A shows the results of flow cytometry analysis obtained in Reference Example 1B.

FIG. 2B shows the results of flow cytometry analysis obtained in Reference Example 1B.

FIG. 2C shows the results of flow cytometry analysis obtained in Reference Example 1C.

FIG. 2D shows the results of flow cytometry analysis obtained in Reference Example 1D.

FIG. 2E shows the results of flow cytometry analysis obtained in Reference Example 1D.

FIG. 2F shows the results of immunoblotting analysis obtained in Reference Example 1E.

FIG. 3A is a schematic diagram for illustrating the structure of the CD300a gene in the wild-type allele, the targeting vector used for preparing a CD300a gene-deficient mouse, and the targeted allele.

FIG. 3B is a photograph taken after electrophoresis of PCR products from the wild-type allele and the mutant allele.

FIG. 3C shows the results of Western blotting using a wild-type mouse and a CD300a-deficient mouse.

FIG. 3D shows the results of flow cytometry analysis of a WT mouse and a CD300a gene-deficient mouse.

FIG. 4A shows the results of flow cytometry analysis obtained in Reference Example 2A.

FIG. 4B shows the results of analysis under a light microscope obtained in Reference Example 2C.

FIG. 4C shows the results of laser scanning confocal microscopy obtained in Reference Example 2C.

FIG. 4D shows the results obtained in Reference Example 2C illustrating the ratio of the number of cells of NIH3T3 or each transfectant showing incorporation of a thymocyte in the cytoplasm.

FIG. 5A shows the results of flow cytometry analysis obtained in Reference Example 2B.

FIG. 5B shows the results of RT-PCR analysis obtained in Reference Example 2B.

FIG. 6A shows the results of flow cytometry analysis obtained in Reference Example 3A.

FIG. 6B shows the results of analysis by the β-hexaminidase assay obtained in Reference Example 3A.

FIG. 7A shows the results of flow cytometry analysis obtained in Reference Example 3B.

FIG. 7B shows the results obtained in Reference Example 3C on the rates of increase in the amounts of various cytokines and chemokines released.

FIG. 7C shows a diagram showing the results obtained in Reference Example 3E on the rates of increase in the amounts of various cytokines and chemokines released.

FIG. 7D shows the results of immunoblotting analysis obtained in Reference Example 3F.

FIG. 7E shows a diagram showing the results of immunoblotting analysis obtained in Reference Example 3G.

FIG. 7F shows a diagram showing the rate of increase in TNF-α, obtained in Reference Example 3G.

FIG. 8 shows the results of flow cytometry analysis obtained in Reference Example 3D.

FIG. 9A shows the results of densitometric analysis obtained in Reference Example 4B.

FIG. 9B shows the results of densitometric analysis obtained in Reference Example 4B.

FIG. 10A shows a diagram showing the results of calculation of the CFU of aerobic bacteria, obtained in Reference Example 4C.

FIG. 10B shows a diagram showing the numbers of neutrophils and macrophages obtained in Reference Example 4C after induction of CD300a neutrophils.

FIG. 11 shows a diagram showing the ratio of the number of each type of macrophages that showed phagocytosis of E. coli, obtained in Reference Example 4C.

FIG. 12A shows a diagram showing the results of flow cytometry analysis obtained in Reference Example 4D.

FIG. 12B shows a diagram showing the rate of survival of each type of mice, obtained in Reference Example 4D.

FIG. 12C shows a diagram showing the bacterial clearance in the intestine in each type of mice in Reference Example 4D, in terms of the bacterial CFU.

FIG. 12D shows the results of flow cytometry analysis obtained in Reference Example 4E.

FIG. 12E shows a diagram showing the rate of survival of each group of mice after administration of TX41 in Reference Example 4F.

FIG. 12F shows a diagram showing the clearance in the intestine after administration of TX41 in Reference Example 4G.

FIG. 12G shows a diagram showing the result of analysis of the change in the number of neutrophils after administration of TX41 in Reference Example 4G.

FIG. 13A shows a diagram illustrating the protocol for induction of asthma with chicken ovalbumin.

FIG. 13B shows the total cell number in the alveolar lavage fluid from each mouse on Day 25 after the beginning of the induction of asthma in Example 1A.

FIG. 13C shows the ratio of eosinophils in the alveolar lavage fluid from each mouse on Day 25 after the beginning of the induction of asthma in Example 1B.

FIG. 14 shows the serum IgE value in each mouse on Day 14 after the beginning of the induction of asthma in Example 1B.

FIG. 15 shows a diagram showing changes with time (daily changes) in the number of times of scratching behavior per 30 minutes in each type of OVA-sensitized mouse (Example 2A).

FIG. 16 shows sections of the skin of each mouse at the end of the 3rd week after sensitization with OVA (Example 2B).

FIG. 17 shows a diagram showing the result of toluidine blue staining of a skin sample from each mouse at the end of the 3rd week after sensitization with OVA (Example 2C).

FIG. 18A shows a graph showing the number of cell layers in the epidermis in each group of mice at the end of the 3rd week after sensitization with OVA (Example 2D).

FIG. 18B shows the numbers of eosinophils and mast cells that showed infiltration into the dermis in skin samples of each group of mice at the end of the 3rd week after sensitization with OVA (Example 2E).

FIG. 19 shows the result of Langerin immunostaining of a skin sample from each group of mice at the end of the 3rd week after sensitization with OVA (Example 2F).

FIG. 20 shows counterstaining of each sample in FIG. 19.

FIG. 21 shows a diagram showing a state where mast cells are interacting with Langerin-positive skin cells (Example 2H).

FIG. 22 is a diagram showing a schedule of the test for confirming the therapeutic effect of TX41.

FIG. 23 shows the total serum IgE level in WT mice after administration of TX74 or TX41, as measured by the ELISA method.

FIG. 24 shows a diagram showing the number of times of scratching behavior in WT mice after administration of TX74 or TX41.

FIG. 25 shows a diagram showing the result of H&E staining of a skin section of a WT mouse after administration of TX74 or TX41.

FIG. 26 shows a diagram showing a state in which a skin section of a WT mouse after administration of TX74 or TX41 was counterstained by toluidine blue staining.

FIG. 27 shows the results of homology analysis of the H-chain and L-chain between TX41 and TX49.

FIG. 28 is a diagram showing a protocol for induction of asthma with chicken ovalbumin, in CD300a gene-deficient mice and wild-type mice (Examples 2M and 2N).

FIG. 29 is a diagram showing the airway pressure in CD300a gene-deficient mice and wild-type mice after induction of asthma according to FIG. 28 (Example 2M).

FIG. 30 is a diagram showing the total number of cells and the number of eosinophils in the bronchial lavage fluid obtained from CD300a gene-deficient mice and wild-type mice after induction of asthma according to FIG. 28 (Example 2M).

FIG. 31 is a diagram showing comparison of the IgE level between CD300a gene-deficient mice and wild-type mice after induction of asthma according to FIG. 28.

FIG. 32 is a diagram showing comparison of the level of IgG1 specific to chicken ovalbumin between CD300a gene-deficient mice and wild-type mice after induction of asthma according to FIG. 28 (Example 2N).

FIG. 33 is a diagram showing comparison of the IgG2c level between CD300a gene-deficient mice and wild-type mice after induction of asthma according to FIG. 28 (Example 2N).

FIG. 34 is a diagram showing comparison of the IgG2b level between CD300a gene-deficient mice and wild-type mice after induction of asthma according to FIG. 28 (Example 2N).

FIG. 35 is a diagram showing comparison of the IgG3 level between CD300a gene-deficient mice and wild-type mice after induction of asthma according to FIG. 28 (Example 2N).

FIG. 36 is a photograph of mediastinal lymph nodes collected from CD300a gene-deficient mice and wild-type mice 3 days after induction of asthma according to FIG. 28 (Example 2O).

FIG. 37 is a diagram showing the results of investigation of the cell number in the mediastinal lymph nodes of the CD300a gene-deficient mice and wild-type mice in FIG. 36 (Example 2O).

FIG. 38 is a diagram showing the results of flow cytometry for investigation of the expression level of a transcription factor FOXP3 in regulatory T (Treg) cells in mediastinal lymph nodes collected from CD300a gene-deficient mice and wild-type mice 7 days after induction of asthma according to FIG. 28 (Example 2P).

FIG. 39 is a diagram showing the results of flow cytometry for investigation of the expression level of a transcription factor specific to T cells, GATA3, in mediastinal lymph nodes collected from CD300a gene-deficient mice and wild-type mice 7 days after induction of asthma according to FIG. 28 (Example 2P).

FIG. 40 is a diagram showing the results of flow cytometry for investigation of the expression level of a transcription factor associated with Th1 differentiation, T-bet, in mediastinal lymph nodes collected from CD300a gene-deficient mice and wild-type mice 7 days after induction of asthma according to FIG. 28 (Example 2P).

FIG. 41 is a diagram showing the results of flow cytometry analysis and gating of CD300a-expressing spleen cells (Example 2Q).

FIG. 42 is a diagram showing the amount of CD300a-expressing spleen cells (CD11b+ CD11c+) (Example 2Q).

FIG. 43 is a diagram showing the amount of CD300a-expressing spleen cells (CD11b+ CD11c−) (Example 2Q).

FIG. 44 is a diagram showing the amount of CD300a-expressing spleen cells (CD11b− CD11c+) (Example 2Q).

FIG. 45 is a diagram showing the results of flow cytometry analysis and gating of CD300a-expressing mediastinal lymph node cells (Example 2Q).

FIG. 46 is a diagram showing the amount of CD300a-expressing mediastinal lymph node cells (CD11b+ CD11c+) (Example 2Q).

FIG. 47 is a diagram showing the amount of CD300a-expressing mediastinal lymph node cells (CD11b+ CD11c−) (Example 2Q).

FIG. 48 is a diagram showing the amount of CD300a-expressing mediastinal lymph node cells (CD11b− CD11c+) (Example 2Q).

FIG. 49 is a diagram illustrating the protocol for observation of the influence of administration of a TX41 antibody on the disease state of asthma (Example 2R).

FIG. 50 is a diagram showing the influence of administration of a TX41 antibody on the total cell number in wild-type mice after induction of asthma (Example 2R).

FIG. 51 is a diagram showing the influence of administration of a TX41 antibody on the eosinophil number in wild-type mice after induction of asthma (Example 2R).

FIG. 52 is a diagram showing the influence of administration of a TX41 antibody on serum IgE in wild-type mice after induction of asthma (Example 2R).

FIG. 53 is a diagram showing the results of confirmation of whether regulatory T cells increase in mediastinal lymph nodes or not after administration of D89E MFG-E8 (Example 2S).

DESCRIPTION OF EMBODIMENTS

The activity modulator according to the present invention, a medicament comprising it, use of a CD300a gene-deficient mouse, and an anti-CD300a antibody, are described below in detail. Literatures used for mentioning conventional knowledge or a known test method on the immune mechanism, CD300a or the like are listed in the end of Examples.

[Activity Modulator]

The activity modulator in the present invention includes those for suppressing inhibitory signal transduction of a CD300a-expressing myeloid cell, as well as those for promoting such inhibitory signal transduction.

The "CD300a-expressing myeloid cell" herein includes a mast cell, macrophage, neutrophil, dendritic cell (e.g., CD11b+ dendritic cell) and the like. CD300a is a collective term for those expressed in mammals such as human and mouse, and the species of organism is not limited.

The "inhibitory signal transduction" is signal transduction that occurs by association of the inhibitory receptor CD300a with phosphatase via the ITIM (Immunoreceptor tyrosine-based inhibitory motif) sequence in the intracellular domain.

<First Activity Modulator>

The first activity modulator by the present invention comprises a component having an action to suppress inhibitory signal transduction via CD300a. In the present invention, as such a component, a substance that inhibits binding of phosphatidyl serine to CD300a, that is, a phosphatidyl serine-binding substance or CD300a-binding substance may be used. The first activity modulator may contain either one of these, or may contain both of these.

(Phosphatidyl Serine-Binding Substance)

The phosphatidyl serine-binding substance as a first activity modulator is not limited as long as it binds to phosphatidyl serine (PS), which is a ligand of CD300a, to inhibit interaction (binding) between the phosphatidyl serine and CD300a expressed in a myeloid cell.

Specific examples of the phosphatidyl serine-binding substance include MFG-E8 (Milk Fat Globular Protein EGF-8); T cell immunoglobulin; and soluble proteins such as soluble TIM-1, soluble TIM-4, soluble stabilin and soluble integrin αvβ3. Among these, MFG-E8 is preferred.

The phosphatidyl serine-binding substance is not limited to native proteins such as MFG-E8, and may be one having an amino acid sequence in which one or several amino acids are deleted, substituted and/or added (mutant) (for example, "D89E MFG-E8" in Examples) as long as the binding capacity to phosphatidyl serine is not lost.

Such a mutant can be prepared by a known method such as site-directed mutagenesis or random mutagenesis.

The "soluble protein" described above means a protein prepared by modifying a native protein, such as a membrane protein, insoluble to the later-described diluent or body fluid by, for example, deleting a hydrophobic domain or adding a hydrophilic peptide by a known genetic recombination technique such that the protein becomes soluble to the diluent or body fluid.

(CD300a-Binding Substance)

The CD300a-binding substance as a first activity modulator is not limited as long as it binds to CD300a to inhibit interaction (binding) between the CD300a expressed in a myeloid cell and phosphatidyl serine.

Specific examples of the CD300a-binding substance include neutralizing antibodies against CD300a. The neutralizing antibody may be a single particular type of monoclonal antibody, or may be a combination of 2 or more types of monoclonal antibodies (or polyclonal antibodies). Further, the neutralizing antibody may be either a full-length antibody or an antibody fragment (Fab fragment, F(ab')$_2$ fragment or the like).

The neutralizing antibody can be prepared by a known method. In cases of a monoclonal antibody, anti-CD300a monoclonal antibodies can be generally prepared by, for example, a procedure comprising immunization with CD300a, preparation of hybridomas, screening, culturing, and recovery. From the thus prepared antibodies, an appropriate monoclonal antibody that has a desired capacity (neutralizing action) to inhibit binding of CD300a to phosphatidyl serine and can exert the action and effect of the present invention may be selected.

(TX41, TX49, and Antibodies Similar to these)

TX41 is an anti-mouse CD300a monoclonal antibody (rat IgG2a), and TX49 is an anti-human CD300a monoclonal antibody (mouse IgG1). Both of these are monoclonal antibodies prepared and used in the later-described Examples, and excellent in the function to suppress signal transduction by inhibition of binding of CD300a to phosphatidyl serine. Therefore, these are preferred as the CD300a-binding substance in the present invention. However, anti-CD300a antibodies that can be used in the present invention are not limited to TX41, TX49, and antibodies similar to these (having a variable region with an equivalent amino acid sequence).

The variable region in the H-chain of TX41 has the amino acid sequence of SEQ ID NO:1; the variable region in the L-chain of TX41 has the amino acid sequence of SEQ ID NO:2; the variable region in the H-chain of TX49 has the amino acid sequence of SEQ ID NO:3; and the variable region in the L-chain of TX49 has the amino acid sequence of SEQ ID NO:4. Each of these variable regions contains 3 complementarity determining regions (CDRs) and 4 framework regions. FIG. 27 shows the results of analysis of homology between the amino acid sequences of the variable regions of TX41 and TX49 (for each of the H-chain and L-chain).

The binding substance for mouse CD300a is preferably an antibody in which the variable region in the H-chain has the amino acid sequence of SEQ ID NO:1, and the variable region in the L-chain has the amino acid sequence of SEQ ID NO:2, according to TX41.

The binding substance for human CD300a is preferably an antibody in which the variable region in the H-chain has the amino acid sequence of SEQ ID NO:3, and the variable region in the L-chain has the amino acid sequence of SEQ ID NO:4, according to TX49.

Further, the binding substance for mouse CD300a may also be an antibody in which the H-chain variable region has an amino acid sequence that is the same as the amino acid sequence of SEQ ID NO:1 except that 1, 2, 3, 4, or 5 amino acid(s) is/are substituted, added, inserted and/or deleted, or an antibody in which the L-chain variable region has an amino acid sequence that is the same as the amino acid sequence of SEQ ID NO except that 1, 2, 3, 4, or 5 amino acid(s) is/are substituted, added, inserted and/or deleted (one of the H-chain and the L-chain may have the above-described mutation(s), or both of these may have the above-described mutation(s)).

Further, the binding substance for human CD300a may also be an antibody in which the H-chain variable region has an amino acid sequence that is the same as the amino acid sequence of SEQ ID NO:3 except that 1, 2, 3, 4, or 5 amino acid(s) is/are substituted, added, inserted and/or deleted, or an antibody in which the L-chain variable region has an amino acid sequence that is the same as the amino acid sequence of SEQ ID NO:4 except that 1, 2, 3, 4, or 5 amino acid(s) is/are substituted, added, inserted and/or deleted (one of the H-chain and the L-chain may have the above-described mutation(s), or both of these may have the above-described mutation(s)).

The sites of such mutations are preferably not in the CDRs or vicinities thereof in the variable regions. Further, in cases where an amino acid is substituted, the substitution is preferably conservative amino acid substitution, in which substitution occurs between amino acids having similar side-chain structures and/or chemical properties.

The form (amino acid sequence, amino acid length) of the constant region, that is, the Fab region excluding the above-described variable region, and the Fc region, of the anti-CD300a antibody may be designed as appropriate as long as the action and effect of the present invention are not inhibited, since the form of the constant region hardly affects the binding capacity to CD300a, that is, the neutralizing action.

That is, the anti-CD300a antibody can be prepared as a fusion protein composed of the above prescribed amino acid sequence of the variable region and a known amino acid sequence of the constant region.

For example, use of a human constant region for preparation of an anti-human CD300a antibody as a human chimeric antibody is one of preferred embodiments. Such an anti-CD300a antibody can be prepared by a known method.

For example, by synthesizing a DNA encoding the above prescribed amino acid sequence of the variable region and linking the synthesized DNA to a DNA encoding an amino acid sequence of the constant region and another/other necessary DNA(s) (transcription factor(s) and/or the like), an expression vector for an anti-CD300a antibody gene can be constructed. By introducing this vector to a host cell and allowing expression of the gene, the anti-CD300a antibody of interest can be produced.

The above-mentioned TX41 and TX49, and antibodies similar to these can be potentially used also for an object other than the action and effect of the present invention, i.e., the inhibition of inhibitory signal transduction that occurs due to binding of phosphatidyl serine to CD300a.

(CD300a siRNA)

Moreover, by suppressing expression of CD300a in myeloid cells in the affected area using an siRNA designed based on a gene sequence of CD300a (available from DNA databases such as DDBJ/EMBL/GenBank=INSD), therapeutic effects for the various diseases described above can be obtained as in the cases where the CD300a gene is deleted or binding of CD300a to phosphatidyl serine is inhibited. In other words, an siRNA against the CD300a gene can also be said to be the substance that inhibits binding of CD300a to phosphatidyl serine in the present invention.

(Use of First Activity Modulator)

The first activity modulator in the present invention can be used for suppressing inhibitory signal transduction of a CD300a-expressing myeloid cell. In this case, the myeloid cell may be either a myeloid cell present in the body, or a myeloid cell separated from the body or cultured in vitro.

By maintaining or increasing activation signaling via CD300a of the myeloid cell by the above action, intercellular signal transduction via chemical mediators released from the myeloid cell is also maintained or increased, and inflammation, allergic reaction and the like that are caused by further intercellular signal transduction that occurs thereafter can then be influenced. Therefore, the first activity modulator can be used as an effective component of the specific medicaments described later. Further, the first activity modulator can also be used as an effective component of an agent to be used as a comparative analysis tool for comparative analysis performed after amelioration of the disease state of an allergic disease (e.g., asthma or atopic dermatitis) in a laboratory animal. For example, a first activity modulator D89E MFG-E8 is useful as an effective component of a medicament or comparative analysis tool since, as described in the Examples below, an effect to increase the number of regulatory T cells, which are involved in suppression of inflammation, can be obtained therewith.

Those skilled in the art can sufficiently presume that CD300a-binding substances (neutralizing antibodies such as TX41 and TX49) and phosphatidyl serine-binding substances (MFG-E8, D89E MFG-E8, and the like) can be therapeutic agents for allergic diseases that are found to show amelioration of symptoms when the CD300a gene is deleted (that is, when binding of CD300a to phosphatidyl serine is completely prevented).

<Second Activity Modulator>

The second activity modulator contains a component having an action to promote inhibitory signal transduction via CD300a (that is, to suppress activation signaling of CD300a). In the present invention, such a component may be a substance that promotes binding of phosphatidyl serine to CD300a. The substance is especially phosphatidyl serine, which is a ligand of CD300a.

In the present invention, the second activity modulator may be used as a comparative analysis tool for carrying out pathology analysis of an allergic disease, or for screening of a possible candidate substance for an effective component of a therapeutic agent or prophylactic agent for the disease.

Further, by performing screening using the CD300a gene-deficient mice provided by another aspect of the present invention, agonists (low molecular compounds, antibodies and the like) for CD300a having the same action as phosphatidyl serine may be discovered, and such agonists can also be used as substances that promote binding of phosphatidyl serine to CD300a.

(Phosphatidyl Serine)

Phosphatidyl serine (PS) is a ligand for CD300a expressed in myeloid cells, and interaction (binding) between PS and CD300a promotes inhibitory signaling of CD300a-expressing cells. For example, in mast cells, inflammatory reaction-associated activities that cause release of chemical mediators such as histamine, cytokines and chemokines are suppressed via this inhibitory signaling. PS is industrially produced, and can be easily obtained.

For CD300a-expressing myeloid cells placed in vitro (in a test environment), apoptotic cells presenting PS (it is known that PS is present inside the cell (in the cytoplasm-side layer of the lipid bilayer) in a normal cell, but presented outside the cell upon occurrence of apoptosis) can also be a second activity modulator. Further, liposomes and the like having a PS-containing lipid membrane formed in the outside can be potentially used as second activity modulators.

(Calcium Salt)

Since the interaction between PS and CD300a in mast cells requires calcium ions, the second activity modulator preferably contains a calcium salt that generates a calcium ion by ionization (e.g., calcium chloride).

The content of the calcium salt in the second activity modulator may be determined appropriately in consideration of the calcium ion concentration in the site of administration, the amount of PS contained in the second activity modulator, and the like.

(Use of Second Activity Modulator)

The second activity modulator according to the present invention can be used for promoting inhibitory signal transduction of a CD300a-expressing myeloid cell. In this case, the myeloid cell may be either a myeloid cell present in the body, or a myeloid cell separated from the body or cultured in vitro.

By suppressing activation signaling via CD300a of the myeloid cell by the above action, intercellular signal transduction via chemical mediators released from the myeloid cell is also suppressed, and inflammation, allergic reaction and the like that are caused by further intercellular signal transduction that occurs thereafter can then be influenced. Thus, for example, the second activity modulator can be used as an effective component of an agent to be used as a comparative analysis tool for comparative analysis performed after allowing exacerbation of an allergic disease (asthma or atopic dermatitis) in a laboratory animal.

[Medicament]

The medicament (pharmaceutical composition) according to the present invention contains the activity modulator as described above as an effective component, and may further contain various pharmaceutically acceptable additives (e.g., a carrier), if necessary.

Such a medicament can be formulated for treatment or prophylaxis of a disease or symptom (especially inflammation reaction) in which inhibitory signal transduction of a CD300a-expressing myeloid cell is involved.

More specifically, by blending the first activity modulator as an effective component, a medicament or the like for treatment or prophylaxis of an allergic disease (asthma or atopic dermatitis) can be prepared.

The site of administration of the medicament is not limited, and may be a site where excessive immune function (inflammation reaction) is occurring, depending on the disease or disease state to which the medicament is applied. Examples of the site include intraperitoneal, intratracheal, subcutaneous, intradermal, and intraurogenital sites.

Since myeloid cells that express CD300a are usually present in submucosal tissues and connective tissues in mammals, the medicament is preferably directly administered to the submucosal tissue or connective tissue at the above-described site, or in the vicinity thereof. The administration may be carried out by injection such as intravenous injection, intraarterial injection, subcutaneous injection, intradermal injection, intramuscular injection or intraperitoneal injection. For example, in cases of treatment or prophylaxis of an inflammatory infection (e.g., bacterial peritonitis), intraperitoneal injection is preferred.

The dose per administration and the number of doses of the medicament (or the effective component contained therein) vary depending on the age, sex and body weight of the patient; symptoms; degree of the therapeutic effect required; administration method; treatment period; type of the effective component; and the like; and may be appropriately controlled. The number of doses is, for example, 1 to several doses per day.

In cases where the medicament contains as an effective component a phosphatidyl serine-binding substance as the first activity modulator, the medicament may be formulated such that the dose per administration of the phosphatidyl serine-binding substance is usually 3 to 15 mg, preferably 5 to 10 mg per 1 kg of the human or animal subjected to the administration.

In cases where the medicament contains as an effective component a CD300a-binding substance as the first activity modulator, the medicament may be formulated such that the dose per administration of the CD300a-binding substance is usually 50 to 150 mg, preferably 50 to 100 mg per 1 kg of the human or animal subjected to the administration.

(Pharmaceutically Acceptable Carrier)

The medicament according to the present invention may contain a pharmaceutically acceptable carrier, if necessary.

The pharmaceutically acceptable carrier is not limited as long as it does not deteriorate the purpose of the medicament, and examples of the carrier include diluents such as aqueous diluents and nonaqueous diluents; stabilizers/preservatives such as antioxidants (e.g., sulfite); buffers such as phosphates; emulsifiers such as surfactants; coloring agents; thickeners; local anesthetics such as lidocaine; solubilizers such as glycols; isotonic agents such as sodium chloride and glycerin; and other additives.

For example, in cases where the dosage form of the medicament according to the present invention is an injection solution, the effective component is preferably dissolved or dispersed in a diluent by blending the diluent such that a desired viscosity and desired concentrations of components are achieved.

Examples of such a diluent include aqueous diluents such as physiological saline and commercially available distilled water for injection; and nonaqueous diluents such as polyethylene glycol, and alcohols including ethanol. The medicament whose dosage form is an injection solution may be sterilized by filtration through a filter, or may be sterilized by blending a microbicide or the like, according to a conventional method.

In cases where the medicament according to the present invention is administered as an injection solution, it may be in the form of an injection solution to be prepared at the time of use. For example, a solid dosage form containing the first activity modulator may be prepared by freeze-drying or the like, and may then be dissolved or dispersed in a diluent to prepare an injection solution at the time of administration.

<Medicament for Asthma>

Inhibition of binding of phosphatidyl serine to CD300a-expressing cells can suppress eosinophilic airway inflammation, and decrease the total serum IgE level. Thus, by using the first activity modulator as an effective component, a medicament for asthma can be obtained.

For example, as described in the Examples below, the airway pressure, and the total number of bronchial lavage cells and the number of eosinophils contained therein, in asthmatic patients can be decreased by administration of a first activity modulator TX41, and the disease state of asthma can therefore be ameliorated. Thus, by using TX41 as an effective component, a medicament useful for asthma can be obtained.

In addition, administration of D89E MFG-E8 increases the number of regulatory T cells, which suppress inflammation, and the disease state of asthma can therefore be ameliorated. Thus, D89E MFG-E8 is also useful as an effective component of a medicament for treatment of asthma.

CD300a is strongly expressed in CD11b+ CD11c+ dendritic cells. In view of this, an example of the mode of the medicament is a liposome preparation having, on its surface, a drug delivery system targeting CD300a as well as CD11b and/or CD11c, such as a hydrophilic polymer (e.g., PEG) to which TX41 (an anti-CD300a antibody) and an anti-CD11b antibody and/or anti-CD11c antibody are bound.

<Medicament for Atopic Dermatitis>

Inhibition of binding of phosphatidyl serine to CD300a-expressing cells can suppress cellular infiltration of eosinophils, mast cells (which are known to interact with skin Langerin-positive dendritic cells in the dermis to activate CD4-positive T cells) and monocytes; suppress hyperplasia of epidermis (fibroblasts); and decrease the total serum IgE level. Thus, by using the first activity modulator as an effective component, a medicament for atopic dermatitis can be obtained. For example, by using a first activity modulator D89E MFG-E8 as an effective component, a medicament which exerts a high inflammation-suppressing effect by increasing the number of regulatory T cells can be obtained.

At present, steroid drugs are widely used as therapeutic agents for atopic dermatitis. However these drugs are said to have only insufficient antipruritic actions. Immunosuppressants such as tacrolimus are also used, but side effects of these existing drugs have been a problem. The above-described medicament can be expected as a novel medicament for allergic diseases such as asthma and atopic dermatitis, which medicament has an antipruritic action and causes less side effects.

[Use of CD300a Gene-Deficient Mouse]
<Use for Asthma>

According to a discovery obtained in the present invention, the symptoms and diseased state of asthma are milder in CD300a-deficient mice than in wild-type mice in cases where the asthma is induced by administration of a substance that induces asthma (mite antigen, chicken ovalbumin, or the like).

For example, as shown in the Examples below, induction of asthma in CD300a-deficient mice with chicken ovalbumin (OVA) results in lower airway resistance and a smaller number of bronchial lavage cells (especially eosinophils, dendritic cells, B cells, and T cells); a significantly larger size of mediastinal lymph nodes, larger number of cells therein, larger number of regulatory T cells (Treg) involved in inhibitory regulation of the immune response (immunological tolerance), and higher levels of IgG2b and IgG2c; and significantly lower levels of IgE and chicken ovalbumin (OVA)-specific IgG1; as compared to wild-type mice. It is useful to analyze the mechanisms (that is, difference from wild-type mice) underlying such indices indicating the mildness of symptoms of asthma, or indices whose association with the mildness of symptoms of asthma is apparently unclear, found in the CD300a-deficient mice, and to analyze what factors are associated with such mechanisms.

That is, the CD300a gene-deficient mouse can be utilized as a model mouse in which asthma is hardly induced after administration of a substance that induces asthma, and can be used as a tool for elucidation of signaling pathways associated with the onset of asthma, and pathology analysis of asthma.

<Use in Relation to Atopic Dermatitis>

According to a discovery obtained in the present invention, administration of a substance that induces atopic dermatitis (mite antigen, chicken ovalbumin, or the like) to CD300a gene-deficient mice causes milder symptoms of atopic dermatitis than administration to wild mice.

That is, the CD300a gene-deficient mouse can be used as a model mouse that hardly develops atopic dermatitis. Further, the CD300a gene-deficient mouse can be used for analysis of signaling pathways involved in atopic dermatitis, pathology analysis of atopic dermatitis, and the like in relation to IL-4 and IL-13 production.

(Method for Preparing CD300a Gene-Deficient Mouse)

The CD300a gene-deficient mouse of the present invention is a mouse in which the CD300a gene on the chromosome is replaced by an inactive CD300a gene and hence the function of CD300a protein is deficient.

The "inactive CD300a gene" means a gene that is incapable of expressing normal CD300a protein due to, for example, partial deletion of the CD300a gene, insertion of another base sequence to the coding region of the CD300a gene, a point mutation(s) in the CD300a gene, or mutation in a regulatory region for expression of the CD300a gene. Examples of the deficient CD300a gene include, but are not limited to, genes in which at least one of the exons 1 to 6 contained in the CD300a gene is deleted.

The term "function of CD300a protein is deficient" means that at least a part of the function of CD300a protein involved in the inhibitory signal transduction related to the present invention is lost (for example, the function of CD300a protein is partially lost by replacement of one of the alleles by an inactive form, as in a heterozygous knockout mouse), preferably means that the function is completely lost.

A common method for obtaining a CD300a gene-deficient mouse using a gene cassette is as follows. However, the CD300a gene-deficient mouse in the present invention is not limited to those obtained by this method.

A targeting vector having a targeted allele (mutant allele) in which the exons of the wild-type allele of the CD300a gene are replaced by an antibiotic resistance gene (marker gene) is prepared. According to a conventional method, a chimeric mouse is obtained using the targeting vector and ES cells. The chimeric mouse is crossed with a wild-type mouse to obtain F1 mice (heterozygote (+/−)), and the F1 mice are crossed with each other to obtain F2 mice.

Genomic DNA is extracted from the F2 mice, and genomic DNA of each mouse is subjected to PCR to investigate the presence/absence of the wild-type allele and the mutant allele in the genomic DNA, to obtain an F2 mouse having only the mutant allele (homozygote (−/−)). Further, in order to confirm the absence of expression of CD300a, cells derived from the mouse are subjected to confirmation by Western blotting using an anti-CD300a antibody, to provide a CD300a gene-deficient mouse.

EXAMPLES

The present invention is described below more concretely by way of Examples. However, the present invention is not limited by the Examples below.

1. Preparation Example (1) Preparation of CD300a-Fc Fusion Protein, MFG-E8 and D89E MFG-E8

(1-1) A CD300a fusion protein having the Fc region of human IgG (CD300a-Fc) was prepared as described in the Document 25 listed below from a chimeric cDNA containing a cDNA of a gene encoding the whole extracellular domain of mouse or human CD300a and a cDNA of a gene encoding human IgG1Fc. The fusion protein in which the extracellular domain of CD300a is derived from mouse is referred to as "mouse CD300a-Fc", and the fusion protein in which the extracellular domain of CD300a is derived from human is referred to as "human CD300a-Fc".

(1-2) MFG-E8 was provided by Mr. Masato Tanaka (RCAI, Yokohama, Japan).

(1-3) D89E MFG-E8 is a mutant of MFG-E8 obtained by site-directed mutagenesis in the RGD motif of MFG-E8 as described in the Document 4 below.

In the obtained D89E MFG-E8, the 89th amino acid as counted from the N-terminus is substituted from aspartic acid to glutamic acid. MFG-E8 (native) binds to both phosphatidyl serine (PS) and $\alpha v \beta 3$ integrin to thereby cross-link apoptotic cells to phagocytes expressing $\alpha v \beta 3$ integrin (Document 4 listed below). On the other hand, D89E MFG-E8 does not bind to $\alpha v \beta 3$ integrin while it binds to phosphatidyl serine (PS).

(2) Mice, and Cecal Ligation and Puncture (CLP)

The knockout mice used in the Examples were prepared or provided as follows.

(i) CD300a Gene-Deficient (Cd300a$^{−/−}$) Mouse

Using a bacterial artificial chromosome (BAC) system, the exons 1 to 6 of the wild-type allele of the Cd300a gene were replaced by a neomycin resistance gene cassette (PGK-GB2-neo) to prepare a targeted allele (mutant allele) (FIG. 3A). Subsequently, a chimeric mouse was obtained according to a conventional method, and the chimeric mouse was crossed with a wild-type mouse to obtain F1 mice (heterozygote (+/−)). The F1 mice were crossed with each other to obtain F2 mice.

In order to select CD300a gene-deficient (Cd300a$^{-/-}$) mice from the F2 mice, genomic DNA was extracted from the tail of each F2 mouse, and the genomic DNA was subjected to PCR to investigate the presence/absence of the WT allele and the mutant allele in the genomic DNA.

As shown in FIG. 3B, the PCR product corresponding to the WT allele and the PCR product corresponding to the mutant allele are detected as a band of about 540 bp and a band of about 700 bp, respectively.

Further, in order to confirm the absence of expression of CD300a in the CD300a gene-deficient mice, cells derived from the CD300a gene-deficient mice were subjected to Western blot analysis using an anti-CD300a antibody. As shown in FIG. 3C, a wild-type mouse showed a band of about 50 kDa derived from CD300a, but this band was not detected in a CD300a gene-deficient mouse.

(ii) C57BL/6J-kit$^{W\text{-}sh/W\text{-}sh}$ Mouse

C57BL/6J-kit$^{W\text{-}sh/W\text{-}sh}$ mice (hereinafter referred to as "kit$^{W\text{-}sh/W\text{-}sh}$ mice" or "mast cell-deficient mice") were provided from RIKEN BioResource Center (Tsukuba, Japan). These mice are known to show deficiency of mast cells (Document 21 listed below), and to show incorporation of DNA by phagocytes without apoptotic DNA fragmentation, followed by degradation of DNA in the phagocytes (Document 12 listed below).

(iii) CAD-Deficient Mouse

The CAD (Caspase-activated DNase)-deficient mouse described in the Document 12 listed below was used.

(iv) In Vivo Removal of Macrophages and Neutrophils

According to description in the Document 30 listed below, clodronate liposomes and control PBS liposomes (Encapsula NanoSciences) were prepared. Subsequently, at Hour 24 after CLP, 0.5 mL of the liposomes were injected to the abdominal cavity of the mouse to remove macrophages.

Further, at Hour 24 after CLP, an anti-Gr-1 antibody was injected into the abdominal cavity of the mouse to remove neutrophils.

All the operations of preparation using mice and the evaluation tests in the Examples were carried out in accordance with the guideline prepared by Animal Care and Use Committee of Laboratory Animal Resource Center, University of Tsukuba.

(3) Antibodies

The manufacturer, or the method for preparation, of each antibody is shown in the Table 1 below.

TABLE 1

| Antibody name | Manufacturer or preparation method |
| --- | --- |
| Control rat antibody | BD Pharmingen |
| Anti-CD11b (M1/70) antibody | BD Pharmingen |
| Anti-F4/80 antibody | BD Pharmingen |
| Anti-c-Kit (2B8) antibody | BD Pharmingen |
| Anti-Gr-1 (RB6) antibody | BD Pharmingen |
| Anti-FcεRI (MAR-1) antibody | BD Pharmingen |
| Anti-TNF-α antibody | BD Pharmingen |
| Human CD300a monoclonal antibody TX49 (mouse IgG1) | Prepared according to a document listed below (*) |
| Mouse CD300a monoclonal antibody TX41 (rat IgG2a) | Prepared according to a document listed below (*) |
| Anti-MCP-1 antibody | BioLegend |
| Anti-IL-13 antibody | eBiosciences |
| Anti-SHP-1 (C-19) antibody | Upstate Biotechnology |
| Anti-SHP-2 (C-18) antibody | Upstate Biotechnology |

(*) Prepared according to the method described in the Document 1 listed below.

(4) Preparation of Each Type of Cells

Each type of cells were prepared as follows.

(i) Bone Marrow-Derived Mast Cells (BMMCs)

In complete RPMI 1649 medium supplemented with a cell growth factor (SCF) (10 ng/mL), IL-3 (4 ng/mL) and fetal bovine serum (FBS) (10%) placed in a 10-cm dish, $2\times10^8$ mouse bone marrow cells were cultured for not less than 5 weeks to prepare bone marrow-derived mast cells (BMMCs). The BMMCs were subcultured every week with fresh medium. Flow cytometry analysis showed that more than 95% of the prepared BMMCs were c-Kit$^+$ FcεRI$^+$ cells.

(ii) Bone Marrow-Derived Macrophages (BMMφ)

In complete RPMI 1649 medium supplemented with M-CSF (10 ng/mL) and fetal bovine serum (FBS) (10%) placed in a 10-cm dish, $2\times10^6$ mouse bone marrow cells were cultured for 1 week to prepare bone marrow-derived macrophages (BMMφ).

(iii) NIH3T3 Cell Transfectant

According to a conventional method, a pMX-neo retrovirus vector plasmid containing a cDNA of Flag-tagged CD300a or cDNA of Flag-tagged CD300d was prepared.

NIH3T3 cells were transfected with the thus prepared plasmid, to obtain a transfectant that stably expresses CD300a or CD300d. The transfectant that stably expresses CD300a and the transfectant that stably expresses CD300d obtained are referred to as "NIH3T3 transfectant (CD300a)" and "NIH3T3 transfectant (CD300d)", respectively.

The NIH3T3 cell transfectant that stably expresses TIM-4 was provided by Mr. T. Kitamura (University of Tokyo). This transfectant is referred to as "NIH3T3 transfectant (TIM-4)".

[Method of Evaluation]

Conditions for the method of evaluation are described below. In the survival test, the Kaplan-Meier log-rank test was used, and, in other evaluation tests, the unpaired Student's t test was used to perform statistical analysis. Statistical significance was assumed at P<0.05.

(5) Binding Assay Etc.

(i) Binding Assay

Cells were stained for 30 minutes in phosphate buffer supplemented with 2% FBS in the presence or absence of 1 mM CaCl$_2$ using CD300a or a control human IgG, and then washed twice with the same buffer, followed by incubation with the F(ab')$_2$ fragment of an FITC-conjugated goat anti-human IgG. Subsequently, for staining with annexin V, the cells were incubated in 10 mM HEPES-NaOH buffer supplemented with 140 mM NaCl and 2.5 mM CaCl$_2$ together with annexin V for 15 minutes at room temperature.

(ii) Binding Inhibition Assay

Cells were preincubated with a monoclonal antibody against mouse CD300a (TX41), control isotype antibody or MFG-E8 for 30 minutes, and then stained with CD300a-Fc as in the above binding assay. Further, in order to analyze whether CD300a-Fc was bound to phospholipid or not, an assay was carried out using a PIP Strip (manufactured by Echelon Biosciences) according to the manufacturer's instructions.

(6) Measurement of CFU (Colony Forming Unit) of Aerobic Bacteria

Serial dilutions of mouse peritoneal perfusate were plated, and the dilutions were cultured on plates containing brain-heart infusion (BHI) agar at 37° C. for 48 hours. Subsequently, the CFU of aerobic bacteria was calculated by measuring the number of colonies in 1 mL of the peritoneal perfusate as described in the Document 27 listed below.

Reference Example 1; Identification of CD300a Ligand

Reference Example 1A

In order to confirm expression of the mouse CD300a ligand in hematopoietic stem cell lines and tumor cell lines, the following test was carried out.

The bone marrow-derived macrophages (BMMφ) obtained in "1. Preparation Example", bone marrow-derived dendritic cells (BMDCs) or IL-3-dependent hematopoietic cell line cells (BaF/3 cells) ($2 \times 10^5$ cells per each type of cells) were incubated in PBS (phosphate buffered saline) containing CD300a-Fc (1 μg) and calcium chloride (1 mM) at 20° C. for 30 minutes, and then stained using a buffer containing an FITC-conjugated anti-human IgG antibody (0.1 μg) and propidium iodide (PI) (1 μg).

The stained cells of each type were subjected to analysis using a flow cytometer (FACSCalibur, manufactured by Becton Dickinson; model number, "E6133").

Further, a control test was carried out in the same manner as in the above test method except that a control human IgG (1 μg) was used instead of mouse CD300a-Fc.

The results of flow cytometry analysis for BMMφ, BMDC and BaF/3 cells are shown in FIG. 1A, FIG. 1B and FIG. 1C, respectively (the results of the control test are shown as "Ctrl Ig").

As shown in FIG. 1A to FIG. 1C, it was found that, in cases where calcium chloride is contained, mouse CD300a-Fc binds to PI$^-$ cells (live cells) but does not bind to PI$^+$ cells (dead cells). That is, the mouse CD300a ligand is suggested to be expressed in dead cells.

Reference Example 1B

In order to test whether mouse CD300a-Fc binds to apoptotic cells, which are a type of dead cells, the following test was carried out.

Thymocytes derived from a C57BL/6 mouse (wild-type mouse) were incubated with dexamethasone (manufactured by Sigma) (10 μM) in RPMI medium to prepare apoptotic thymocytes.

The obtained apoptotic cells (cell number, $2 \times 10^5$) were incubated in a medium (PBS) containing CD300a-Fc (1 μg), APC-conjugated annexin V (manufactured by BD Pharmingen) (1 μl) and calcium chloride (1 mM) at 20° C. for 30 minutes, and stained using a buffer containing an FITC-conjugated anti-human IgG antibody (0.1 μg) and propidium iodide (PI) (1 μg).

The stained cells of each type were subjected to analysis using a flow cytometer (FACSCalibur, manufactured by Becton Dickinson; model number, "E6133") (results: FIG. 2A).

Further, the cells were subjected to flow cytometry analysis under the same conditions as in the above test except that a medium supplemented with no calcium chloride was used instead of the medium supplemented with calcium chloride (results: FIG. 2B).

According to FIG. 2A, it can be seen that, in the presence of calcium chloride, mouse CD300a-Fc bound to thymocytes that are stained with annexin V but did not bind to thymocytes that are not stained with annexin V (annexin V$^-$). That is, it is suggested that mouse CD300a-Fc binds to apoptotic thymocytes.

On the other hand, it can be seen as shown in FIG. 2B that mouse CD300a-Fc did not bind to apoptotic thymocytes in the absence of calcium chloride.

From these test results, it can be understood that mouse CD300a binds to apoptotic cells dependently on calcium ions.

Reference Example 1C

The apoptotic cells obtained in Reference Example 1B (cell number, $2 \times 10^5$) were incubated in a medium (PBS) supplemented with CD300a-Fc (1 μg), APC-conjugated annexin V (manufactured by BD Pharmingen) (1 μl), control human IgG1 (1 μg) and calcium chloride (1 mM) at 20° C. for 30 minutes, and stained using a buffer containing an FITC-conjugated anti-human IgG antibody (0.1 μg) and propidium iodide (PI) (1 μg).

The stained cells of each type were subjected to analysis using a flow cytometer (FACSCalibur, manufactured by Becton Dickinson; model number, "E6133") (results: FIG. 2C "HuIgG1").

Further, the cells were subjected to flow cytometry analysis under the same conditions as in the above test method except that "TX41", which is a monoclonal antibody, or "MFG-E8", which is a protein expressed in the macrophage, was used instead of the control human IgG1 (results: FIG. 2C "TX41" and "MFG-E8").

As described above, the "TX41" used herein is an anti-mouse CD300a monoclonal antibody, and blocks binding of mouse CD300a to the ligand.

"MFG-E8" is known to bind to both phosphatidyl serine (PS) and αvβ3 integrin to thereby cross-link apoptotic cells to phagocytes expressing αvβ3 integrin (Document 4 listed below).

As can be seen by comparison among the results of flow cytometry shown in FIG. 2C, mouse CD300a did not bind to apoptotic cells in the presence of TX41 or MFG-E8.

From this viewpoint, it is suggested that mouse CD300a-Fc has binding capacity to PS (that is, the ligand of CD300a is PS).

Reference Example 1D

In order to test whether or not human CD300a binds to apoptotic cells similarly to mouse CD300a, the following test was carried out.

First, Jurkat cells (human T-cell line) were suspended in RPMI 1640 medium, and the resulting medium was irradiated with UV for 60 minutes to prepare apoptotic Jurkat cells.

Flow cytometry analysis was carried out under the same test conditions as in Reference Example 1A except that the "Jurkat cell-derived apoptotic cells" were used as apoptotic cells instead of the apoptotic cells derived from wild-type mouse thymocytes, and "human CD300a-Fc" was used instead of the "mouse CD300a-Fc" (results: FIG. 2D).

Further, cytometry analysis was carried out under the same test conditions as in Reference Example 1B except that the "Jurkat cell-derived apoptotic cells" were used as apoptotic cells instead of the apoptotic cells derived from wild-type mouse thymocytes; "human CD300a-Fc" was used instead of the "mouse CD300a-Fc"; and "TX49" or "control human IgG1" was used instead of "TX41" (results: FIG. 2E "TX49" or "HuIgG1"). "TX49" is an anti-human CD300a antibody (monoclonal antibody), and blocks binding of CD300a to the ligand.

As can be seen from FIG. 2D to FIG. 2E, human CD300a-Fc bound to annexin V$^+$ cells but did not bind thereto in the presence of the anti-human CD300a antibody. That is, it is suggested that, similarly to mouse CD300a-Fc, human CD300a also binds to apoptotic cells.

Reference Example 1E

Liquids (test liquids) containing various phospholipids (PS, PC, PE) (100 pmol) were spotted on a membrane (PIP-strip (manufactured by Echelon Bioscience)) to allow adsorption of the phospholipids on the membrane.

Subsequently, the membrane was immersed in TBST buffer (pH 8.0) containing mouse CD300a-Fc (1.5 µg/mL), supplemented with calcium chloride (1 mM) and BSA, at 20° C. for 2 hours.

Thereafter, the membrane was washed 3 times with TBST buffer that does not contain mouse CD300a-Fc (pH 8.0) to remove CD300a-Fc unbound to the phospholipids on the membrane. Detection was then carried out using TBST buffer (pH 8.0) containing HRP-conjugated anti-human IgG (manufactured by Jackson Immun), supplemented with BSA (results: FIG. 2F).

In FIG. 2F, "PE", "PC" and "PS" indicate the positions where phosphatidyl ethanolamine, phosphatidyl choline and phosphatidyl serine were spotted on the membrane, respectively, and "Blank" indicates a position where no phospholipid was spotted on the membrane.

According to FIG. 2F, CD300a bound to neither PE nor PC, and bound specifically to PS. From the results of Reference Examples 1A to 1E, it can be understood that CD300a binds to phosphatidyl serine (PS) dependently on calcium ions (that is, the ligand of CD300a is PS).

Reference Example 2: Functional Analysis of CD300a (1)

Some PS-binding receptors are known to be expressed in phagocytes and to be involved in removal of apoptotic cells under physiological and pathological conditions (Documents 4 to 9 listed below).

PS is known to mediate the so-called "eat me" signal in phagocytes (macrophages and the like), which are cells expressing CD300a (Documents 10 and 11 listed below). In view of this, the tests described in the Reference Examples 2A to 2C below were carried out to test whether CD300a is involved in phagocytosis of apoptotic cells or not.

Reference Example 2A

Thymocytes derived from a CAD-deficient mouse were treated in the same manner as in Reference Example 1B to prepare apoptotic thymocytes.

Subsequently, macrophages (thioglycolate-induced peritoneal macrophages) derived from a CD300a gene-deficient mouse ($2 \times 10^5$ cells) were co-cultured with the apoptotic thymocytes derived from a CAD-deficient mouse at a ratio of 1:5 (macrophages:apoptotic thymocytes (cell numbers)) in a 8-well Lab-TeK II chamber slide (manufactured by Nalge Nunc) at 37° C. for 1 hour.

Subsequently, as described in the Documents 5 and 26 listed below, the co-cultured macrophages were washed with cold PBS and fixed with a fixative containing paraformaldehyde (1%). The fixed macrophages where then subjected to TUNEL staining using a buffer containing FITC-labeled dUTP (manufactured by Roche).

Not less than 50 cells randomly selected from the stained macrophages were analyzed using a laser scanning confocal microscope ("FV10i", manufactured by Olympus Corporation; product number, 1B22358), and the number of TUNEL-positive cells (apoptotic cells) contained per one macrophage cell was counted. The ratios of macrophages containing apoptotic cells in the numbers of 0 to 8 (phagocytosis rates) were calculated as percentages with respect to the total number of macrophages (results: FIG. 4A "Cd300a$^{-/-}$").

Further, the phagocytosis rates were measured under the same conditions as in the above test except that macrophages derived from a wild-type mouse were used instead of the macrophages derived from a CD300a gene-deficient mouse (results: FIG. 4A "WT").

As shown in FIG. 4A, no evident difference in the phagocytosis rate was found between the case where the macrophages were derived from a CD300a gene-deficient mouse and the case where the macrophages were derived from a wild-type mouse.

Reference Example 2B

In order to test whether mast cells express known PS receptors (TIM-1, TIM-4, stabilin 2 and integrin αvβ3), the following test was carried out.

Bone marrow-derived mast cells (BMMCs) (cell number, $2 \times 10^5$) were incubated at 20° C. for 30 minutes in a medium (PBS) containing a PE (Phycoerythrin)-conjugated TIM-1 monoclonal antibody (0.1 µg), APC-conjugated TIM-4 monoclonal antibody (0.1 µg) and Alexa-conjugated anti-mouse CD300a monoclonal antibody (TX41) (0.5 µg).

Subsequently, the stained cells were washed twice using PBS, and subjected to analysis using a flow cytometer (FACSCalibur, manufactured by Becton Dickinson; model number, "E6133") (results: FIG. 5A "Bone marrow-derived mast cells").

Further, flow cytometry analysis was carried out under the same conditions as in the above test method except that peritoneal macrophages or BM-derived macrophages were used instead of the BMMCs (results: FIG. 5A "Peritoneal macrophages" and "Bone marrow-derived macrophages").

Further, using High Capacity cDNA Reverse Transcription Kit (manufactured by Applied Biosystems), cDNAs were prepared from peritoneal macrophages and BMMCs. Using each prepared cDNA, the expression levels of stabilin 2, BAI-1, αv integrin, Cd300a and β-actin (loading control) were analyzed by RT-PCR (results: FIG. 5B).

As can be seen from FIG. 5A and FIG. 5B, unlike the cases of macrophages, the mast cells expressed CD300a and αvβ3 integrin, but showed only low levels of expression of TIM-1, TIM-4 and stabilin 2, which are PS receptors involved in phagocytosis.

Reference Example 2C

The NIH3T3 transfectant (CD300a) (cell number, $6 \times 10^4$) was co-cultured with FITC-labeled cells (apoptotic thymocytes or thymocytes (live cells)) for 2 hours, and washed with PBS, followed by analysis under a light microscope (BZ-9000, manufactured by Keyence) (results: FIG. 4B).

Further, the cells obtained after the co-culture and washing were fixed with a fixative containing paraformaldehyde, Vectashield (manufactured by Vector Laboratories), and analyzed using a laser scanning confocal microscope (results: FIG. 4C). In FIG. 4C, green areas (indicated by arrows) indicate phagocytosed cells (apoptotic thymocytes or thymocytes (live cells)).

Further, analysis using a light microscope and a laser scanning confocal microscope was carried out under the same conditions as in the above test except that NIH3T3 untransfected cells (negative control) or "NIH3T3 transfectant (TIM-4)" cells (positive control) were used instead of the NIH3T3 transfectant (CD300a).

In FIG. 4B and FIG. 4C, "NIH-3T3" and "NIH-3T3/Tim4" show images of "NIH3T3" (untransfected cells) and "NIH3T3 transfectant (TIM-4)", respectively, which images were obtained using a light microscope and a laser scanning confocal microscope.

The images obtained with the laser scanning confocal microscope were used to measure the ratios of the number of untransfected cells and the number of cells of each transfectant that incorporated apoptotic thymocytes into the cytoplasm (percentages with respect to the number of co-cultured untransfected cells or to the number of co-cultured cells of each transfectant) (results: FIG. 4D "apoptotic").

Further, similarly, the ratios of the number of NIH3T3 cells and the number of cells of each transfectant that incorporated thymocytes (live cells) into the cytoplasm (percentages with respect to the number of co-cultured untransfected cells or to the number of co-cultured cells of each transfectant) were measured (results: FIG. 4D "Live").

As shown in FIG. 4B, unlike NIH3T3, both of the above transfectants adhered to apoptotic thymocytes. However, based on FIG. 4C and FIG. 4D, it can be seen that only the NIH3T3 transfectant (TIM-4) incorporated apoptotic thymocytes to show phagocytosis.

Although data are not shown, the NIH3T3 transfectant (CD300a) did not show phagocytosis of live cells (thymocytes), similarly to NIH3T3.

From the results of Reference Examples 2A to 2C, it can be understood that CD300a is not involved in phagocytosis of apoptotic cells by macrophages.

Reference Example 3; Functional Analysis of CD300a (2)

As shown in FIG. 5, mast cells express CD300a, but, unlike macrophages, the cells do not express TIM-1, TIM-4 and stabilin, which are PS receptors.

PS is known to bind to these PS receptors directly or indirectly, and contribution of these receptors to incorporation of apoptotic cells is known (Document 13 listed below). In view of this, the tests described below in the Reference Examples 3A to 3C were carried out in order to test whether CD300a also has such a function or not (whether or not there is functional overlap in incorporation of apoptotic cells).

Reference Example 3A

In complete RPMI 1649 medium supplemented with a cell growth factor (SCF) (10 ng/mL), IL-3 (4 ng/mL) and fetal bovine serum (FBS) (10%) placed in a 10-cm dish, $2\times10^8$ bone marrow cells (BM cells) derived from a CD300a gene-deficient mouse were cultured for 4 weeks to prepare bone marrow-derived mast cells (BMMCs) of the CD300a gene-deficient mouse. The BMMCs were subcultured every week with fresh medium.

Subsequently, the obtained BMMCs were incubated in RPMI1649 medium containing an FITC-conjugated anti-FcεRIα antibody (0.1 µg) and a PE-conjugated anti-c-Kit antibody (0.1 µg/mL) at 4° C. for 30 minutes, and analyzed by flow cytometry (results: FIG. 6A "CD300a$^{-/-}$").

Further, flow cytometry analysis was carried out under the same test conditions as in the above test except that BMMCs were prepared using bone marrow cells derived from a wild-type mouse instead of the bone marrow cells derived from a CD300a gene-deficient mouse (results: FIG. 6A "WT"). Each number in FIG. 6A indicates the ratio of the cells shown in each box. Each test was repeated 3 times independently.

Using each type of BMMCs, a β-hexosaminidase release assay (degranulation assay) was carried out as follows (for detailed conditions, see the Document 29 below).

First, $1\times10^5$ to $2\times10^5$ BMMCs of each type in the logarithmic growth phase were cultured at 37° C. for one day and night in a 24-well plate coated with gelatin (manufactured by Sigma), and then incubated at 37° C. for 1 hour in a medium that contains a biotin-conjugated mouse anti-trinitrophenol IgE (0.5 mg/mL) but does not contain a supplement.

Subsequently, streptavidin was added to the medium to cause cross-linking between the biotin-conjugated mouse anti-trinitrophenol IgE molecules, and culture was performed at 37° C. for 45 minutes, followed by collecting the supernatant.

To the collected supernatant, a buffer (pH 4.5) containing p-nitrophenyl-N-acetyl-β-D-glucosamide (manufactured by Sigma), citric acid (0.4 M) and sodium phosphate (0.2 M) was added, and the resulting mixture was incubated at 37° C. for 3 hours to allow hydrolysis reaction of p-nitrophenyl-N-acetyl-β-D-glucosamide by released β-hexosaminidase. This reaction was stopped by adding 0.2 M glycine-NaOH (pH 10.7), and the absorbance at a wavelength of 415 nm, which increases as hydrolysis of p-nitrophenyl-N-acetyl-β-D-glucosamide proceeds, was measured to quantify the amount of β-hexosaminidase released. The rate (%) of increase in the amount of β-hexosaminidase released with respect to the amount observed with untreated BMMCs of each type is shown in FIG. 6B.

FIG. 6B shows the ratio of BMMCs that released β-hexosaminidase. As shown in FIG. 6A and FIG. 6B, no significant difference was found in expression of FcεRIα and c-Kit (marker proteins for mast cells) and the rate of increase in the amount of β-hexosaminidase released between the case where the BMMCs were derived from a CD300a gene-deficient mouse and the case where the BMMCs were derived from a wild-type mouse.

That is, it can be seen that differentiation from bone marrow cells and degranulation mediated by FcεRI are not influenced by CD300a.

Reference Example 3B

BMMCs derived from a CD300a gene-deficient mouse and the apoptotic cells obtained in Reference Example 1B (BMMCs:apoptotic cells=10:1 (ratio in terms of the cell number)) were incubated in PBS containing calcium chloride (1 mM), APC-conjugated annexin V (1 µl), CD300a-Fc (1 µg/mL) and MFG-E8 (5 µg) at 20° C. for 30 minutes, and then stained using a buffer containing an FITC-conjugated anti-human IgG antibody (0.1 µg/mL) and propidium iodide (PI) (1 µg).

The stained cells were subjected to analysis using a flow cytometer (FACSCalibur, manufactured by Becton Dickinson; model number, "E6133") (results: FIG. 7A "MFG-E8").

Further, flow cytometry analysis was carried out under the same conditions as in the above test except that a control IgG was used instead of MFG-E8 (results: FIG. 7A "Ctrl Ig").

From the results shown in FIG. 7A, it can be seen that CD300a-Fc bound to apoptotic cells (annexin V$^+$) in the presence of the control IgG, but that the binding was specifically inhibited in the presence of MFG-E8 (PS-binding substance).

The concentrations of cytokines and chemokines in the supernatant of this sample mixture were quantified using ELISA kits manufactured by BD Pharmingen (TNF-α and IL-6) and R&D Systems (MIP-2, MCP-1, IL-13 and MIP-1α). As a result, none of the cytokines and chemokines could be detected.

Reference Example 3C

In order to test whether or not stimulation by LPS (lipopolysaccharide) changes the amounts of cytokines released in the coexistence of BMMCs and apoptotic cells, the following test was carried out.

BMMCs derived from a CD300a gene-deficient mouse and apoptotic cells (BMMCs:apoptotic cells=10:1 (ratio in terms of the cell number)) were incubated in RPMI containing LPS (1 µg/mL) for 4 hours, and the supernatant of the medium was then collected.

Subsequently, the levels of cytokines and chemokines were measured 3 times using ELISA kits manufactured by BD Pharmingen (TNF-α and IL-6) and R&D Systems (MIP-2, MCP-1, IL-13 and MIP-1α), and the rate of increase in the amount of each cytokine or chemokine released with respect to the amount observed with the BMMCs that had not been subjected to the above LPS treatment was calculated (results: FIG. 7B "Cd300a$^{-/-}$").

Further, the rate of increase in the amount of each cytokine or chemokine was calculated under the same conditions as in the above test except that BMMCs derived from a wild-type mouse were used instead of the BMMCs derived from a CD300a gene-deficient mouse (results: FIG. 7B "WT").

As shown in FIG. 7B, LPS increased the amounts of cytokines released in both types of BMMCs. However, the BMMCs derived from a CD300a gene-deficient mouse showed significantly larger increases in the amounts of TNF-α, IL-13 and MCP-1 than the BMMCs derived from a wild-type mouse.

Reference Example 3D

Further, the following test was carried out in order to test the rates of increase in intracellular cytokines and chemokines in BMMCs.

BMMCs derived from a CD300a gene-deficient mouse and the apoptotic cells obtained in Reference Example 1B (BMMCs:apoptotic cells=10:1 (ratio in terms of the cell number)) were incubated in a medium (RPMI) containing LPS (lipopolysaccharide) (1 µg/mL) for 4 hours, and the BMMCs and apoptotic cells after the incubation were then incubated in a medium (FIX & PERM, manufactured by Invitrogen) supplemented with fluorescently labeled antibodies against various cytokines and chemokines and formaldehyde at 4° C. for 20 minutes. The stained cells were subjected to analysis using a flow cytometer (FACSCalibur, manufactured by Becton Dickinson; model number, "E6133") (results: FIG. 8, arrows (1)). Further, flow cytometry analysis was carried out under the same conditions as in the above test except that a control antibody was used instead of the fluorescently labeled antibodies against various cytokines and chemokines (control test (results: FIG. 8, arrows (2))).

Further, flow cytometry analysis was carried out under the same conditions as in the above test except that BMMCs derived from a wild-type mouse were used instead of the BMMCs derived from a CD300a gene-deficient mouse (results: FIG. 8, arrows (3)). Further, flow cytometry analysis was carried out under the same conditions as in the above test except that a control antibody was used instead of the fluorescently labeled antibodies against various cytokines and chemokines (control test (results: FIG. 8, arrows (4))).

Each graph in FIG. 8 shows the amount of increase in MFI (mean fluorescence intensity) observed for each cytokine or chemokine in each type of BMMCs, relative to that of LPS-untreated BMMCs.

According to FIG. 8, in both types of BMMCs, the amounts of cytokines and chemokines in the cytoplasm increased compared to the case where the LPS treatment was not carried out. In particular, it can be seen that the BMMCs derived from a CD300a gene-deficient mouse showed significantly larger increases in the amounts of TNF-α and the like in the cytoplasm than the BMMCs derived from a wild-type mouse.

Reference Example 3E

D89E MFG-E8 is a variant (mutant) of MFG-E8 and has a point mutation (D89E) in the RGD motif. D89E MFG-E8 binds to PS, but does not bind to αvβ3 integrin.

In view of this, the following test was carried out in order to test whether or not the amounts of cytokines and chemokines released from BMMCs change in the presence of D89E MFG-E8.

TNF-α, IL-13, MCP-1 and IL-6 were quantified in the same manner as in Reference Example 3C except that LPS as well as D89E MFG-E8 (5 µg/mL) were added to the medium containing BMMCs derived from a CD300a gene-deficient mouse and apoptotic cells (results: FIG. 7C "CD300a$^{-/-}$").

Further, TNF-α, IL-13, MCP-1 and IL-6 were quantified under the same conditions as in the above test except that BMMCs derived from a wild-type mouse were used instead of the BMMCs derived from a CD300a gene-deficient mouse (results: FIG. 7C "WT").

As shown in FIG. 7C, in the presence of D89E MFG-E8, no significant difference was found in the concentrations of cytokines between the case where the BMMCs were derived from a CD300a gene-deficient mouse and the case where the BMMCs were derived from a wild-type mouse.

Reference Example 3F

CD300a is known to have an immunoreceptor tyrosine-based inhibitory motif (ITIM) in the intracellular domain, and to induce SHP-1 upon cross-linking by an anti-CD300a antibody (Document 14 listed below).

In view of this, the following test was carried out in order to test whether CD300a interacts with SHP-1 or not. As in Reference Example 3C, BMMCs derived from a CD300a gene-deficient mouse or wild-type mouse were co-cultured with apoptotic cells in the presence of LPS for 4 hours, and a homogenate of the cells was subjected to immunoprecipitation with an anti-CD300a antibody (TX41).

Using the thus obtained immunoprecipitates, immunoblotting with an anti-SHP-1 antibody or an anti-CD300a antibody was carried out as described in Document 14 listed below (results: FIG. 7D).

As can be seen from these results, the BMMCs responded to the stimulation with LPS to induce (recruit) SHP-1 when they were co-cultured with apoptotic cells. However, CD300a did not recruit SHP-1 in the presence of D89E MFG-E8.

That is, it is thought that induction (recruitment) of SHP-1 by CD300a in response to LPS stimulation requires binding of PS to CD300a.

Reference Example 3G

In order to investigate whether SHP-1 is involved in CD300a-mediated signaling or not, first, Ptpn6 (SHP-1 gene) of BMMCs derived from a wild-type mouse was knocked out with an siRNA to prepare SHP-1-deficient (Ptpn6-KD) wild-type mouse-derived BMMCs under the following conditions. Further, similarly, SHP-1-deficient (Ptpn6-KD) CD300a gene-deficient mouse-derived BMMCs were prepared from BMMCs derived from a CD300a gene-deficient mouse.

With 1 mL of X-treme Gene siRNA transfection reagent (manufactured by Roche), 0.5 mM siRNA (SHP-1 siRNA) (siGENOME SMARTpool; ThermoScientific Dharmacom) targeting the SHP-1 gene (Ptpn6 gene) in BMMCs was mixed, and $5 \times 10^5$ BMMCs derived from a CD300a gene-deficient mouse were transfected therewith as described in the Document 28 listed below, to prepare SHP-1 knockdown BMMCs derived from a CD300a gene-deficient mouse (BMMCs (CD300a$^{-/-}$•Ptpn6-KD)).

Further, SHP-1 knockdown BMMCs derived from a wild-type mouse (BMMCs (WT•Ptpn6-KD)) were prepared under the same conditions as in the above test except that BMMCs derived from a wild-type mouse were used instead of the BMMCs derived from a CD300a gene-deficient mouse.

Here, in order to confirm that the BMMCs of each type were transfected with the SHP-1 siRNA and that the expression level of SHP-1 was decreased, a lysate of BMMCs (CD300a$^{-/-}$•Ptpn6-KD) or BMMCs (WT•Ptpn6-KD) was subjected to immunoblotting analysis using an anti-SHP-1 antibody, anti-SHP-2 antibody or anti-β-actin antibody (results: FIG. 7E).

As can be seen from FIG. 7E, the BMMCs transfected with the SHP-1 siRNA showed a decreased expression level of SHP-1. "Ctrl" shows results of immunoblotting analysis using BMMCs transfected with a control siRNA instead of the SHP-1 siRNA.

Subsequently, BMMCs (CD300a$^{-/-}$•Ptpn6-KD) or BMMCs (WT•Ptpn6-KD), and the apoptotic cells obtained in Reference Example 1B (BMMCs:apoptotic cells=10:1 (ratio in terms of the cell number)) were incubated in RPMI supplemented with calcium chloride (1 mM) and LPS (lipopolysaccharide) (1 μg/mL) for 4 hours, and the amount of TNF-α released was measured in the same manner as in Reference Example 3B (results: FIG. 7F).

As shown in FIG. 7F (left graph), the BMMCs derived from a CD300a gene-deficient mouse produced a significantly larger amount of TNF-α than the BMMCs derived from a wild-type mouse. On the other hand, as shown in FIG. 7F (right graph), in the cases where the BMMCs derived from a wild-type mouse or a CD300a gene-deficient mouse were transfected with the SHP-1 siRNA, the amount of TNF-α released was almost the same between the BMMCs derived from a wild-type mouse and the BMMCs derived from a CD300a gene-deficient mouse, and no significant difference was found between these.

These results suggest that binding of PS to CD300a causes CD300a to induce SHP-1 and to thereby mediate signaling that causes suppression of the activity of BMMCs, resulting in suppression of secretion of TNF-α.

From the results of Reference Example 3, it can be understood that the interaction between PS and CD300a inhibits production of inflammation-inducing (LPS-inducing) cytokines and chemokines from BMMCs, and that the interaction recruits SHP-1, resulting in suppression of secretion of TNF-α.

Reference Example 4; Functional Analysis of CD300a (3)

TNF-α, IL-3 and MCP-1 produced by mast cells are chemoattractants for neutrophils, and known to play important roles in bacterial clearance in CLP peritonitis mice (Patent Documents 15 to 19 listed below).

In view of this, in order to study whether CD300a has a bacterial clearance function or not, the Reference Examples 4A to 4H below were carried out.

Reference Example 4A

A wild-type mouse was subjected to midline incision of 1 to 2 cm on the cecum (ventral region), and the end portion was ligated. After performing two times of puncture using a 27-gauge needle in the ligated area, the cecum was returned to the abdomen. Thereafter, 1 mL of sterile physiological saline was subcutaneously injected for rehydration, and the incision site was closed by suturing. Details of the procedure and conditions for the CLP are described in the Document 16 listed below.

Before performing the CLP and 4 hours after performing the CLP, peritoneal perfusate was collected. Subsequently, APC-conjugated annexin V (1 μg) and CD300-Fc (1 μg) were added to the peritoneal perfusate, and staining was performed with an FITC-conjugated anti-human IgG and PI (propidium iodide), followed by performing analysis by flow cytometry (results: FIG. 12A).

As can be seen from the results shown in FIG. 12A, the site of peritonitis was a site where a number of cells were undergoing apoptosis, as described in the Document 20 listed below.

That is, the immune regulation by mast cells in the site of peritonitis is suggested to be influenced by CD300a.

Reference Example 4B

In order to test the relationship between CD300a and the immune regulation by mast cells, proteome analysis was carried out as follows.

First, CLP was carried out in the same manner as in Reference Example 4A using a wild-type mouse and a mast cell-deficient mouse (kit$^{W\text{-}sh/W\text{-}sh}$).

Four hours after performing the CLP, peritoneal perfusate was collected from each mouse, and the collected peritoneal perfusate was subjected to proteome analysis of cytokines and chemokines using Proteome Profiler Array (manufactured by R&D Systems) according to the manufacturer's instructions.

FIG. 9A shows the results of densitometry analysis (proteome analysis) using the peritoneal perfusate from each of the wild-type mouse and the mast cell-deficient mouse (kit$^{W\text{-}sh/W\text{-}sh}$ mouse) (in FIG. 9A, "PC" indicates a positive control).

FIG. 9B shows the pixel densities of the signals for the chemokines and cytokines, which were obtained from the densitometry images shown in FIG. 9A.

As can be seen from the results shown in FIG. 9B, at Hour 4 after the CLP, the concentrations of chemokines were higher in the kit$^{W-sh/W-sh}$ mouse than in the wild-type mouse. Similar results were obtained in 2 replicates of the test.

Reference Example 4C

In the same manner as in Reference Example 4B, peritoneal perfusate was collected from wild-type mice and mast cell-deficient mice (kit$^{W-sh/W-sh}$ mice) (n=3 per each type of mice).

Subsequently, a dilution series of each peritoneal perfusate was prepared, and the prepared serial dilutions of peritoneal perfusate were plated to perform culture on plates containing brain-heart infusion (BHI) agar at 37° C. for 48 hours. Thereafter, the CFU of aerobic bacteria was calculated by measuring the number of colonies in 1 mL of the peritoneal perfusate as described in the Document 27 listed below (results: FIG. 10A).

Further, the numbers of neutrophils and macrophages in each peritoneal perfusate were also counted. The results are shown in FIG. 10B as "neutrophil" and "macrophage", respectively.

From a wild-type mouse and mast cell-deficient mouse (kit$^{W-sh/W-sh}$), BM-derived macrophages were prepared. These macrophages (cell number: 1×10$^6$) were co-cultured for 1 hour in a medium containing fluorescein-labeled *E. coli* placed in a 24-well plate, and the number of each type of macrophages that phagocytosed *E. coli* was counted by flow cytometry to calculate the ratio of phagocytosing macrophages (results: FIG. 11 "BM macrophage").

A test was carried out under the same conditions as in the above test except that PEC macrophages derived from a wild-type mouse or mast cell-deficient mouse (kit$^{W-sh/W-sh}$ mouse) were used instead of the BM-derived macrophages derived from a wild-type mouse or mast cell-deficient mouse (kit$^{W-sh/W-sh}$ mouse), to calculate the ratio of phagocytosing macrophages (results: FIG. 11 "PEC macrophage").

As shown in FIG. 10A, it can be seen that, at Hour 4 after the CLP, the mast cell-deficient mouse (kit$^{W-sh/W-sh}$ mouse) showed a lower intraperitoneal bacterial CFU and a larger number of neutrophils than the wild-type mouse. On the other hand, as shown in FIG. 10B and FIG. 11, the number of macrophages and their phagocytosis were not significantly different between the genotypes.

Reference Example 4D

In order to test whether CD300a is involved in induction (recruitment) of neutrophils or not, the following Example was carried out.

To mast cell-deficient mice (Kit$^{W-sh/W-sh}$ mice), PBS buffer containing BMMCs derived from a wild-type mouse (cell number, 1×10$^6$) was administered by intraperitoneal injection (n=20). On Day 28 after the administration, CLP was performed in the same manner as in Reference Example 4A, and the survival rate of the mice was measured (results: FIG. 12B "WT BMMCs→Kit$^{W-sh/W-sh}$").

Further, a test was carried out under the same conditions as in the above test except that BMMCs derived from a CD300a gene-deficient mouse were used instead of the BMMCs derived from a wild-type mouse, and the survival rate of mice was measured (results: FIG. 12B "CD300a$^{-/-}$ BMMCs→Kit$^{W-sh}$/Kit$^{W-sh}$"). "Kit$^{W-sh}$/Kit$^{W-sh}$" in FIG. 12B indicates the survival rate of mast cell-deficient mice (Kit$^{W-sh/W-sh}$ mice) subjected to CLP without administration of BMMCs.

According to FIG. 12B, the mast cell-deficient mice (Kit$^{W-sh/W-sh}$ mice) subjected to administration of BMMCs derived from a wild-type mouse showed a higher survival rate even after the CLP, compared to the case where administration of BMMCs was not carried out.

However, it can be seen that the mast cell-deficient mice (Kit$^{W-sh/W-sh}$ mice) subjected to administration of BMMCs derived from a CD300a gene-deficient mouse showed a significantly higher survival rate even after CLP, compared to the mice subjected to administration of BMMCs derived from a wild-type mouse and the mice that had not been subjected to administration of BMMCs (FIG. 12B).

Further, as a result of measuring the bacterial CFU in the same manner as in Reference Example 4C using peritoneal perfusate of each type of mice at Hour 4 after the CLP, the mast cell-deficient mice (Kit$^{W-sh/W-sh}$ mice) subjected to administration of BMMCs derived from a CD300a gene-deficient mouse showed a significantly higher bacterial clearance than other mice (results: FIG. 12C).

Reference Example 4E

In order to test whether or not the amount of TNF-α released increases by intraperitoneal administration of BMMCs to a mast cell-deficient mouse (Kit$^{W-sh/W-sh}$ mouse), the following Example was carried out.

Twenty four hours before CLP, a CFSE-labeled BMMC mixture (BMMCs derived from a CD300a gene-deficient mouse:BMMCs derived from a wild-type mouse=1:1 (ratio in terms of the cell number)) was administered to mast cell-deficient mice (Kit$^{W-sh/W-sh}$ mice) by intraperitoneal injection.

The mice after injection of the BMMC mixture was subjected to CLP in the same manner as in Reference Example 4A, and, at Hour 4 after the CLP, peritoneal perfusate was collected. Each type of BMMCs contained in the peritoneal perfusate were subjected to analysis using a flow cytometer (FACSCalibur, manufactured by Becton Dickinson; model number, "E6133") (results: FIG. 12D).

As shown in FIG. 12D, it can be seen that, at Hour 4 after the CLP, the BMMCs derived from a CD300a gene-deficient mouse (CD300a$^-$CFSE$^+$ cells) showed production of a significantly larger amount of TNF-α than the BMMCs derived from a wild-type mouse (CD300a 'CFSE' cells).

Reference Example 4F

In order to test the influence of administration of an anti-CD300a monoclonal antibody (TX41) on CD300a, the following Example was carried out.

First, CLP was carried out in the same manner as in Reference Example 4A except that 500 μg of an anti-CD300a monoclonal antibody (TX41) (n=13) was intraperitoneally injected to wild-type mice 1 hour or 18 hours before the CLP, and the survival rate of the mice was measured in the same manner as in Reference Example 4D (results: FIG. 12E "Antibody to CD300a").

Further, a test was carried out under the same conditions as in the above test except that an isotype control antibody (n=11) was used as a control instead of TX41 (n=13), and the survival rate of the mice was measured (results: FIG. 12E "Control antibody").

As shown in FIG. 12E, it was found that the survival time of wild type mice was longer in the cases where CLP was carried out 1 hour or 18 hours after administration of TX41 by intraperitoneal injection, compared to the cases of administration of the control antibody.

Reference Example 4G

From each mouse at Hour 4 after the CLP in Reference Example 4F, peritoneal perfusate was collected. The obtained peritoneal perfusate was treated in the same manner as in Reference Example 4C to measure the bacterial CFU and the number of neutrophils (control antibody: n=5 and anti-CD300a monoclonal antibody: n=5) (FIG. 12F and FIG. 12G, respectively).

The administration of TX41 by intraperitoneal injection did not cause damage to myeloid cells including mast cells in the mice.

As shown in FIG. 12F and FIG. 12G, the administration of TX41 to wild-type mice by intraperitoneal injection 1 hour or 18 hours before CLP resulted in a significant increase in neutrophils and an increased bacterial clearance in the abdominal cavity.

From the results of Reference Example 4, it can be understood that inhibition of the interaction between PS and CD300a by TX41 or the like allows prevention of sepsis induced by peritonitis.

Under physiological conditions, a number of cells undergo apoptosis. In this process, PS receptors play a central role in incorporation of the apoptotic cells, and are indispensable for preventing the progression of autoimmune diseases (Document 22 listed below).

On the other hand, it is known that, under pathological conditions such as microbial infection, cell death due to apoptosis remarkably increases, and this causes inflammation reaction by mast cells via receptors (e.g., Toll-like receptors) against pathogen-associated molecular patterns (PAMPs) (Documents 15, 23 and 24 listed below). Further, mast cells are known to play important roles in immune reaction against pathogens.

Thus, from the results in the above Examples, it can be understood that PS not only provides an incorporation signal for phagocytes via several kinds of PS receptors, but also has an effect to effectively suppress inflammation reaction caused by mast cells via CD300a, as newly discovered in the present invention.

It can therefore be understood that phosphatidyl serine-binding substances (e.g., MFG-E8) and CD300a-binding substances (e.g., neutralizing antibodies against CD300a) inhibit the interaction between PS and CD300a in mast cells to thereby activate the mast cells or maintain such an activity.

That is, it can be understood that these substances are useful as effective components of medicaments used for prophylaxis of, for example, various LPS-inducing inflammatory infections (and sepsis caused thereby).

<Asthma>
(Materials and Methods)
(Mice)

C57BL/6J mice were purchased from Clea Japan, Inc. CD300a gene-deficient mice (CD300a$^{-/-}$ mice) were obtained by crossing Balb/c CD300a gene-deficient mice prepared in the inventors' laboratory with the purchased WT C57BL/6J mice for 12 generations, and then performing back-crossing. Male and female mice that were 8 to 10 weeks old at the beginning of induction of asthma were used.

(OVA-Induced Asthma)

FIG. 13A shows the protocol for inducing asthma with chicken ovalbumin. On Days 0, 7 and 14 after the beginning of induction of asthma, a mixture of 100 µg of chicken ovalbumin (OVA, chicken egg albumin, manufactured by Sigma) and 100 µL of aluminum hydroxide gel (ALUM, ALhydrogel 2%, manufactured by Invitrogen) was intraperitoneally injected to each mouse.

Further, on Days 21, 22 and 23 after the beginning of induction of asthma, each mouse was subjected to inhalation of 10% chicken ovalbumin prepared by dilution with PBS, for 30 minutes using an ultrasonic nebulizer (NE-U17, Omuron). On Day 25 after the beginning of induction of asthma, each mouse was subjected to bronchoalveolar lavage (BAL), and serum was collected from each mouse.

Example 1A

FIG. 13A, FIG. 13B (Bronchoalveolar Lavage BAL)

After subjecting each mouse to tracheotomy, washing was performed 3 times with 1 mL of 2% FBS/PBS, followed by collecting the washing liquid and measuring the cell number. As shown in FIGS. 13A and B, the cell number in the bronchoalveolar lavage fluid (BAL fluid) of each mouse on Day 25 after the beginning of induction of asthma was significantly smaller in the CD300a gene-deficient mice than in the WT mice in terms of both the total cell number and the number of eosinophils. This result indicates that CD300a exacerbated eosinophilic airway inflammation caused by ovalbumin (OVA), and that the CD300a gene-deficient mice showed amelioration of symptoms of eosinophilic airway inflammation.

Example 1B

Analysis of Cells in Bronchoalveolar Lavage Fluid (FIG. 13C)

With CD45.2-FITC, Siglec-F-PE, CD11b-APC Cy7, CD11c-PEC Cy7 and F4/80-Alexa (all of these were purchased; BD), $1 \times 10^6$ cells in the collected bronchoalveolar lavage fluid were stained, and CD45$^+$SiglecF$^-$CD11b$^+$CD11c$^-$F4/80$^-$ was analyzed as the eosinophil fraction by flow cytometry (FACS).

FACS analysis of cells in the bronchoalveolar lavage fluid of the mice on Day 25 after the beginning of induction of asthma showed the ratio of eosinophils among CD45-positive cells (CD45$^+$SiglecF$^-$CD11b$^+$CD11c$^-$F4/80$^-$). The CD300a gene-deficient mice showed a significantly smaller ratio of infiltrating eosinophils in the BAL fluid than the WT mice.

Example 1C

Measurement of Serum IgE Value (FIG. 14)

Serum IgE was measured by ELISA using a rat anti-mouse IgE (BD) and a biotinylated anti-mouse IgE (BD).

As shown in FIG. 14, the CD300a gene-deficient mice showed significantly lower serum IgE values during the period of sensitization to cause chicken ovalbumin-induced asthma. Based on comparison of the serum IgE value (index of the degree of allergy) among the OVA-induced asthma model mice on Disease Day 14, the CD300a gene-deficient mice showed significantly lower serum IgE values than the WT mice.

It is thought that administration of an anti-CD300a antibody, which suppresses signal transduction of CD300a, causes significant suppression of serum IgE in chicken-ovalbumin-induced asthma.

<Atopic Dermatitis>

Involvement of CD300a in atopic dermatitis was investigated. The materials and methods, and Examples are shown below.

(Experimental Animals)

Balb/c mice were purchased from Clea Japan, Inc., and kept in the inventors' laboratory under approved breeding room conditions. The mice used in this study were 8 CD300a (MAIR-I) gene-deficient mice and 8 Balb/c wild-type (WT: Wild Type) mice. During the experimental period, each mouse was provided with food and water ad libitum, and kept under normal laboratory conditions.

(Percutaneous Sensitization)

Each mouse was mildly anesthetized with isoflurane (Mylan, Osaka, Japan), and the hair on the back was shaved with an electric shaver. An area (1 cm$^2$) on the back skin of each mouse was subjected to at least 10 times of tape stripping using adhesive cellophane tape.

On the gauze of Band Aid (registered trademark) tape, 100 µg of chicken ovalbumin (OVA) in 100 µL of phosphate buffered saline was placed, and the resulting tape was applied to the bodies of 5 mice in each group subjected to the tape stripping. To the remaining 3 mice, PBS was applied with tape. The tape was once replaced on Day 2, and OVA sensitization with the tape was carried out every day for 1 week.

Each mouse was kept without OVA sensitization during Week 2. During Week 3, the mouse was subjected again to OVA sensitization in the same manner as described above. At the end of Week 3, each mouse was sacrificed, and samples for histology and ELISA were collected.

(Number of Times of Scratching Behavior)

The number of times of scratching behavior was counted by careful observation of each mouse for 30 minutes at the end of each of Week 1 to Week 3.

(Histology)

For histological observation, the skin of the OVA-sensitized area in each mouse was collected. Each collected skin sample was cut into small tissue blocks, and immersed in 4% paraformaldehyde at 4° C. for 24 hours.

After this fixation, a dehydration step was carried out. All skin samples were then quickly frozen in acetone in a container containing dry ice. The samples were stored at −30° C. until use.

The skin samples were then cut into sections with a thickness of 4 µm using a frozen section preparation apparatus, Coldtome HM560E (manufactured by Carl Zeiss, Jena, Germany), and placed on slide glasses precoated with New Silane III (Muto Pure Chemicals, Co., Ltd., Tokyo, Japan).

The tissue sections were stained with hematoxylin-eosin (manufactured by Sakura Finetek Japan), and then stained with toluidine blue (manufactured by Santa Cruz Biotechnology, Inc.).

Evaluation of histological finding of the tissue was performed for the skin depth (cell layer); infiltration of eosinophils, monocytes and mast cells; and the level of hyperplasia of fibroblasts.

Example 2A

Number of Times of Scratching Behavior (FIG. 15)

FIG. 15 shows the number of times of scratching behavior per 30 minutes in each mouse. Pruritus (a disease that causes itch without causing eruption) is a common condition for atopic dermatitis. Therefore, the evaluation was carried out by counting the number of times of scratching behavior by careful observation of each animal for 30 minutes during the OVA sensitization.

As shown in FIG. 15, the OVA-sensitized WT mice (♦) showed a severe condition of scratching behavior after the OVA sensitization, and a larger number of times of scratching behavior than the OVA-sensitized CD300a gene-deficient mice (▲). The largest number of times of scratching behavior was observed at the end of the 4th OVA sensitization.

During the OVA sensitization, the most severe symptom of scratching behavior was observed in the WT mice (FIG. 15). Appearance of a severe symptom of scratching behavior is one of the most common pathological features of atopic dermatitis. Thus, involvement of CD300a (MAIR-I)-positive cells in an important role in atopic dermatitis might become clear.

Example 2B

Observation (See FIG. 16)

The skin of each OVA-sensitized mouse was observed.

FIG. 16(A) shows the skin of a WT mouse that had not undergone chicken-OVA sensitization. In untreated WT mice, which had not been subjected to the chicken-ovalbumin sensitization, cellular infiltration was not found in the dermis, and a thin epidermis could be observed. The lower panels in FIG. 16 show magnified views of the rectangular areas in the upper panels. The length of each thick bar corresponds to 10 µm.

On the other hand, as shown in FIG. 16(B), the skin of the OVA-sensitized WT mice showed hyperplasia of the epidermis and hyperplasia of fibroblasts. Obvious infiltration of eosinophils (see white arrowheads) and monocytes was found in the dermis of the skin in the WT mice subjected to sensitization with chicken ovalbumin.

As shown in FIG. 16(C), in the epidermis of the CD300a gene-deficient mice that had not been subjected to OVA sensitization, cellular infiltration was not found, and a thin epidermis could be observed similarly to FIG. 16(A).

Surprisingly, as shown in FIG. 16(D), the skin of the OVA-sensitized CD300a gene-deficient mice showed an increased thickness of the epidermis, but did not show hyperplasia of the epidermis. Further, the dermis showed neither cellular infiltration nor hyperplasia of fibroblasts.

Example 2C

Staining of Mast Cells

See FIG. 17

As shown in FIG. 17, all mouse skin samples were subjected to toluidine blue staining. Toluidine blue staining is a staining method that preferentially stains intracellular granules in mast cells.

FIG. 17(A) shows the skin of a WT mouse that had not been subjected to OVA sensitization. FIG. 17(B) shows the skin of an OVA-sensitized WT mouse. FIG. 17(C) shows the skin of a CD300a gene-deficient mouse that had not been subjected to OVA sensitization. FIG. 17(D) shows the skin of an OVA-sensitized WT mouse. Stained mast cells are indicated by open arrowheads.

As shown in FIG. 17, after the OVA sensitization, an increased number of mast cells were found in the skin of the WT mouse. Moreover, the epidermis in the mouse was thicker than that in the CD300a gene-deficient mouse.

Example 2D

Measurement of Number of Cell Layers

FIG. 18A

All mouse skin samples were subjected to counting of the number of cell layers in the epidermis (see FIG. 18A). After the OVA sensitization, the WT mice showed the largest number of cell layers. On the other hand, in the OVA-sensitized CD300a gene-deficient mice, the number of cell layers was less than half of this number.

Example 2E

Counting of Number of Eosinophils and Number of Mast Cells

FIG. 18B

As shown in FIG. 18B, all mouse epidermal samples were subjected to counting of the number of eosinophils and the number of mast cells showing infiltration into the dermis, which are indices for atopic dermatitis. The largest cell numbers were observed in the epidermis of the WT mice after the sensitization with chicken ovalbumin.

On the other hand, in the OVA-sensitized CD300a gene-deficient mice, the increases in the number of eosinophils and the number of mast cells were milder than those in the WT mice. After the OVA sensitization, hyperplasia of epidermis and hyperplasia of fibroblasts appeared most severely in the WT mice (FIG. 16 and FIG. 18A). Hyperplasia of epidermis and fibroblasts is another major pathological feature of atopic dermatitis.

Further, a high level of infiltration of eosinophils, mast cells and monocytes was found in the skin of the OVA-sensitized WT mice (FIG. 16 to FIG. 18B). Interaction between infiltrating eosinophils and hyperplasia of fibroblasts causes secretion of IL-31. IL-31 is an itch-inducing cytokine (Document 34 listed below: Wong C K et al., 2012).

Therefore, after OVA sensitization, WT mice show more severe features of atopic dermatitis than CD300a gene-deficient mice.

(Immunohistology)

In order to detect CD300a (MAIR-I) and the Langerin antigen on serial sections of the skin, the single-step or two-step method of enzyme immunohistochemistry was carried out. First, all sections were rinsed 3 times with phosphate-buffered saline supplemented with 0.05% Tween (TPBS, pH 7.4). The sections were then immersed for 30 minutes in each of cold absolute methanol and 0.5% $H_2O_2$.

After the washing in TPBS, the sections were subjected to blocking treatment using the Blocking One Histo reagent (Nacalai Tesque, Inc., Kyoto, Japan) for 10 minutes, and then washed with TPBS. The skin sections were cultured at 4° C. for 18 hours in the presence of anti-Langerin goat IgG (Santa Cruz Biotechnology, Inc., Santa Cruz, Calif., US) and biotinylated anti-CD300a (MAIR-I) rat IgG 2aλ (prepared in the inventors' laboratory), and then at room temperature for 1 hour in the presence of biotinylated donkey anti-goat IgG as the secondary antibody for Langerin.

Finally, these were cultured in the presence of DAB/Metal Concentrate (Thermo Scientific, Waltham, Mass., US), and counterstained with hematoxylin. Negative control sections were cultured in the presence of TPBS or an isotype control antibody instead of the primary antiserum.

Example 2F

Langerin Immunostaining

FIG. 19

The epidermis of each mouse was investigated to see whether or not it is positive for Langerin, which is a dendritic cell marker in immunostaining. Langerin is a C-type lectin expressed in Langerhans cells, and also expressed in part of dermal dendritic cells. Langerin is involved in recognition and incorporation of antigens, and formation of Birbeck granules, which are responsible for intracellular antigen delivery.

(Results)

FIG. 19(A) shows the epidermis of an untreated WT mouse (mouse without OVA sensitization). FIG. 19(B) shows the epidermis of an OVA-sensitized WT mouse. FIG. 19(C) shows the epidermis of an untreated CD300a gene-deficient mouse. FIG. 19(D) shows the epidermis of an OVA-sensitized CD300a gene-deficient mouse. The panels a, b, c and d are magnified views of the rectangular areas in the upper panels.

After the OVA sensitization, a significantly larger number of Langerin-positive cells were found in the epidermis of WT mice than in the epidermis of CD300a gene-deficient mice. The arrowheads indicate Langerin-positive cells. Each scale bar represents 10 µm.

Example 2G

Counterstaining after Langerin Immunostaining

FIG. 20

Immunopositivity of the Langerin antibody was evaluated by counterstaining with toluidine blue. The skin of the WT mouse showed an increased number of Langerin-positive cells in the dermis. In the dermis, interaction of several Langerin-positive cells with mast cells was found. Mast cells were stained in purple. Each scale bar represents 10 µm.

Langerhans cells and skin dendritic cells are major antigen-presenting cells in the skin. Langerhans cells are positive for the Langerin antigen in their cell membranes, and Langerin-positive cells are also present among skin dendritic cells (Document 35 listed below: Nakajima S. et al, 2012).

Skin Langerin-positive dendritic cells interact with mast cells to activate CD4-positive T cells (Document 36 below: Otsuka A. et al., 2011). In the OVA-sensitized model, the numbers of mast cells (FIG. 17 and FIG. 18B) and Langerin-positive cells (see FIG. 19) largely increased in the skin of the OVA-sensitized WT mice (see white arrowheads in FIG. 19 for comparison). In the skin of the OVA-sensitized WT mice, interaction between mast cells and Langerin-positive skin cells was found (FIG. 20).

(Discussion)

Thus, it can be deduced that atopic dermatitis more severely appears in the skin of WT mice than the skin of CD300a gene-deficient mice. These results suggest that CD300a (MAIR-I) plays an important role in atopic dermatitis.

In the dermis of the WT skin, CD300a (MAIR-I)-positive cells largely increased after the OVA sensitization (FIG. 20).

This result further confirms that CD300a (MAIR-I)-positive cells play an important role in atopic dermatitis.
(Treatment of Atopic Dermatitis)
(Treatment with Anti-CD300a (MAIR-I) Antibody)

In the present experiment, 6 Balb/c mice of 7 weeks old were used. According to the protocol shown in FIG. 22, 3 animals out of the 6 animals were subjected to intravenous injection of anti-CD300a (MAIR-I) rat IgG 2aλ (TX41), and the remaining 3 animals were subjected to intravenous injection of a rat IgG 2aλ control antibody (TX74). Both of these antibodies were prepared and checked in the inventors' laboratory. "TX74" is an isotype control antibody of TX41, and does not have a neutralizing action as described below. Each antibody was diluted with sterile PBS to an antibody concentration of 1600 µg/mL, and 150 µL of the dilution was injected at once.
<Blocking of CD300a (MAIR-I) Antigen by Injection of CD300a (MAIR-I) Antibody>

FIG. 22 shows the procedure to block the CD300a (MAIR-I) antigen in a Balb/c WT mouse. Each thick line indicates the period of OVA sensitization. The arrowheads indicate the schedule of injection of the antibodies.

Total serum IgE was evaluated at the end of each week of sensitization. Histological samples were collected after the continuous sensitization. The anti-rat CD300a (MAIR-I) antibody IgG 2aλ (TX41), and the control antibody (TX74), which is an isotype thereof, were used for intravenous injection.
(ELISA)

Peripheral blood was collected from the retro-orbital cavity using a plain glass hematocrit tube (Drummond Scientific Company, Broomall, Pa., US), and centrifuged at 12000 rpm for 5 minutes.

Serum was collected by cutting the tube, and the whole serum was diluted with a blocking serum before use in ELISA. The ELISA experiment was carried out according to the standard protocol for total IgE, recommended by BD Biosciences, California, US.

Example 2H

Immunoreaction with Anti-CD300a Antibody (Confirmation of Presence of Receptors)

FIG. 21

Immunopositivity of an anti-CD300a antibody was evaluated with a skin sample of each mouse. FIG. 21(A) shows untreated epidermis of a WT mouse, and (B) shows OVA-sensitized epidermis of a WT mouse.

The epidermis of WT mice after OVA sensitization showed cells that are significantly immunopositive. The epidermis of CD300a gene-deficient mice did not show immunopositive reaction. The arrowheads in (B) indicate CD300a (MAIR-I)-positive cells. Each scale bar represents 10 µm.

Example 2I

Treatment by Administration of CD300a Antibody (FIG. 23)

(ELISA)

As shown in FIG. 22, each of TX41 and TX74 was administered to WT mice according to the above-described procedure, and the IgE level, which is an index of atopic dermatitis, was measured.

FIG. 23 shows the total serum IgE level measured by ELISA. The IgE level after OVA sensitization was higher in the mice to which TX74 was injected than in the mice to which TX41 was injected.

Example 2J

Treatment by Administration of Anti-CD300a Antibody (FIG. 24)

As shown in FIG. 24, after the OVA sensitization, the WT mice to which TX74 was injected showed a more severe scratching behavior than the WT mice to which TX41 was injected.

Example 2K

H&E Staining (FIG. 25)

As shown in FIG. 25, skin sections of the WT mice in Example 2I were subjected to H&E staining. After the OVA sensitization, the skin of the WT mice to which TX74 was injected showed higher levels of hyperplasia of the epidermis and infiltration of monocytes than the skin of the WT mice to which TX41 was injected. In FIG. 25, the scale bar in the lower right corner of each photograph represents 10 µm.

Example 2L

Toluidine Blue Staining (FIG. 26)

As shown in FIG. 26, the skin of each WT mouse was subjected to toluidine blue staining. After the OVA sensitization, the skin of the WT mice to which TX71 was injected showed more mast cells than the skin of the WT mice to which TX41 was injected. Each scale bar represents 10 µm, similarly to FIG. 25.
(Discussion)

The total IgE and the number of scratching behavior were higher in the mice to which TX74 was injected than the mice to which TX41 was injected (see FIG. 23 and FIG. 24). The epidermal thickness, number of infiltrating cells, number of fibroblasts and number of mast cells were also higher in the mice to which TX74 was injected than the mice to which TX41 was injected (see FIG. 25 and FIG. 26).

From these results, it could be further confirmed that CD300a (MAIR-I) plays an important role in atopic dermatitis, and the effect of TX41, which is an anti-CD300a antibody, as a therapeutic agent for atopic dermatitis could be confirmed.

Example 2M

Observation of Disease State of Asthma in CD300a Gene-Deficient Mice

Method: CD300a gene-deficient mice and wild-type mice were subjected to intraperitoneal administration of 100 µg OVA/100 µL aluminium hydrogel on Days 0, 7, and 14, and then to intranasal administration of a spray liquid of 10% OVA/PBS on Days 21, 22, and 23 to induce asthma (FIG. 28). On Day 25, the mice were subjected to inhalation of methacholine, and measurement of the airway pressure with a high-performance respiratory function analysis system ("FLexivent™", manufactured by Primetech Corporation). Bronchial lavage was performed with 3 mL of PBS to collect lavage fluid. Cells were collected from the bronchial lavage fluid by centrifugation, and the cell population was analyzed based on surface markers by flow cytometry.

Result: Compared to the wild-type mice, the CD300a gene-deficient mice showed lower airway pressure after the inhalation of methacholine (FIG. 29), and smaller total cell numbers and eosinophil numbers in the bronchial lavage fluid (FIG. 30). It can be seen that the CD300a gene-deficient mice showed milder disease states than the wild-type mice.

Example 2N

IgE Value Etc. in CD300a Gene-Deficient Mice

Method: Asthma was induced in the same manner as in Example 2M (FIG. 28). On Day 25, serum was collected, and serum IgE, OVA-specific IgG1, IgG2b, IgG2c, and IgG3 were measured by ELISA.

Result: Compared to the wild-type mice, the CD300a gene-deficient mice showed lower IgE and OVA-specific IgG1, and higher IgG2b and IgG2c (FIG. 31 to FIG. 35).

Since IgE and OVA-specific IgG1 are indices of immune response by Th2 cells, their lower values indicate reduced induction of Th2 cells, and therefore reduced allergic reaction in the CD300a gene-deficient mice (FIG. 31 and FIG. 32).

The blood level of IgG2c, which is an index of immune response by Th1 cells, was higher in the CD300a gene-deficient mice than in the WT mice. Thus, the results suggested enhanced immune reaction by Th1 cells in the CD300a gene-deficient mice relative to the WT mice. This enhancement of immune reaction by Th1 cells indicates relative reduction of immune reaction by Th2 cells (FIG. 33).

Example 2O

Observation of Mediastinal Lymph Nodes of CD300a Gene-Deficient Mice after Immunization Method: CD300a gene-deficient mice and wild-type mice were subjected to intraperitoneal administration of 100 μg OVA/100 μL aluminium hydrogel, and their mediastinal lymph nodes were collected on Day 3, followed by isolation of cells therefrom and measurement of the cell number.

Result: Compared to the wild-type mice, the CD300a gene-deficient mice showed enlarged lymph nodes (FIG. 36), and larger numbers of cells therein (FIG. 37).

Example 2P

Observation of Number of Regulatory T Cells in Lamina Propria in CD300a Gene-Deficient Mice Method: CD300a gene-deficient mice and wild-type mice were subjected to intraperitoneal administration of 100 μg OVA/100 μL aluminium hydrogel, and their mediastinal lymph nodes were collected on Day 7. Cells were isolated therefrom and stained, and expression of intracellular transcription factors was analyzed by flow cytometry.

Result: Compared to the wild-type mice, the CD300a gene-deficient mice showed larger numbers of CD25-positive FOXP3-positive cells among CD4-positive cells, that is, CD4+ CD25+ FOXP3+ Treg cells in mediastinal lymph nodes (FIG. 38 to FIG. 40). The increase in Treg cells, which have various immunosuppressive functions, indicates that immune functions of the CD300a gene-deficient mice were suppressed relative to the wild-type mice, and that the disease state of asthma was milder in the CD300a gene-deficient mice as a result.

Example 2Q

Observation of CD300a Expression in CD11b+ Dendritic Cells

Method: Expression of CD300a in the spleen and mediastinal lymph nodes was analyzed by flow cytometry.

Result: Strong expression of CD300a in CD11b-positive CD11c-positive cells could be found in both spleen cells and mediastinal lymph node cells of wild-type mice (FIG. 41 to FIG. 48).

Example 2R

Observation of Influence of Administration of TX41 Antibody on Disease State of Asthma Method: Wild-type mice were subjected to intraperitoneal administration of 100 μg OVA/100 μL aluminium hydrogel on Day 0, Day 7, and Day 14, and then to intranasal administration of a spray liquid of 10% OVA/PBS on Day 21, Day 22, and Day 23 to induce asthma (FIG. 49). During this process, 300 μg of a TX41 antibody or control IgG antibody was intraperitoneally administered on Days 0, 3, 7, and 10. On Day 25, the mice were subjected to inhalation of methacholine, and measurement of the airway pressure with a high-performance respiratory function analysis system ("FLexivent™", manufactured by Primetech Corporation). Bronchial lavage was performed with 3 mL of PBS to collect lavage fluid. Cells were collected from the bronchial lavage fluid by centrifugation, and the number of eosinophils was analyzed by flow cytometry.

Results: Compared to the mice to which the control antibody was administered, the mice to which the TX41 antibody was administered showed lower airway pressure after the inhalation of methacholine, and smaller total cell numbers and eosinophil numbers in the bronchial lavage fluid (FIG. 50 to FIG. 52). It can be seen that the TX41 antibody (anti-CD300a antibody) has an effect to ameliorate the disease state of asthma.

Example 2S

Confirmation of Increase in Regulatory T Cells in Mediastinal Lymph Nodes after Administration of D89E MFG-E8

Methods: Wild-type mice were subjected to intraperitoneal administration of 100 μg OVA/100 μL aluminium hydrogel, and their mediastinal lymph nodes were collected on Day 7. During this process, 100 μg of D89E MFG-E8 or a control protein (EPT MFG-E8) was intraperitoneally administered on Days 1 and 2. Cells were isolated from mediastinal lymph nodes and stained, and expression of intracellular transcription factors was analyzed by flow cytometry.

Results: Compared to the mice to which the control protein (EPT MFG-E8) was administered, the mice to which D89E MFG-E8 was administered showed larger numbers of CD25-positive FOXP3-positive cells among CD4-positive cells in the mediastinal lymph nodes (FIG. 53). D89E MFG-E8 has been suggested to have an effect to ameliorate the disease state of asthma by increasing Treg cells, which have various immunosuppressive functions.

1. K. Yotsumoto et al., J Exp Med 198, 223 (Jul. 21, 2003).
2. H. kumagai et al., Biochem Biopys Res Commun 307, 719 (Aug. 1, 2003).
3. D. H. Chung et al., J Immunol 171, 6541 (Dec. 15, 2003).
4. R. Hanayama et al., Nature 417, 182 (May 9, 2002).
5. M. Miyanishi et al., Nature 450, 435 (Nov. 15, 2007).
6. N. Kobayasi et al., immunity 27, 927 (December 2007).
7. S. Y. Park et al., Cell Death Differ 15, 192 (January 2008).
8. D. Park et al., Nature 450, 430 (Nov. 15, 2007).
9. R. S. Scott et al., Nature 411, 207 (May 10, 2001).
10. V. A. Fadok et al., J Immunol 148, 2207 (Apr. 1, 1992).
11. J. Savill, I. Dransfield, C. Gregory, C. Haslett, Nat Rev Immunol 2, 965 (December, 2002)
12. S. Nagata, Annu Rev Immunol 23, 853 (2005)
13. V. K. Kuchroo, V. Dardalon, S. Xiao, A. C. Anderson, Nat Rev Immuno 8, 577 (August 2008)
14. Y. Okosi et al., Int Immunol 17, 65 (January 2005).
15. J. S. marshall, Nat Rev Immunol 4, 787 (October 2004).
16. B. Echtenacher, D. N. Mannel, L, Hultner, Nature 381, 75 (May 2, 1996).
17. R. Malaviya, T. Ikeda, E. Ross, S. N. Abraham, Nature 381, 77 (May 2, 1996).
18. A. Matsukawa et al., J Immunol 163, 6148 (Dec. 1, 1992).
19. J. M. Baumhofer et al., Eur J Immunol 28, 610 (February 1998)
20. R. S. Hotchkiss, D. W. Nicholson, Nat Rev Immunol 6, 813 (November 2006).
21. M. A. Grimbaldeston et al., Am J Pathol 835 (September 2005).
22. R. Hanayama et al., Science 304, 1147 (May 21, 2004).
23. S. C. Bischoff, Nat Rev Immunol 7, 93 (February 2007).
24. S. N. Abraham, A. L. St John, Nat Rev Immunol 10, 440 (January).
25. S. Tahara-Hanaoka et al., Int Immunol 16, 533 (April 2004).
26. Y. Yamanisi et al., J Exp Med 207, 1501 (July 5).
27. G. Plitas, B. M. Burt, H. M. Nguyen, Z. m. Bamboat, R. P. DeMatteo, J Exp Med 205, 1277 (Jun. 9, 2008).
28. H. An et al., Immunity 25, 919 (December 2006).
29. Y. Yang, B. Seed, Nat Biotechnol 21, 447 (April 2003).
30. N. Van Roollen, J Immunol Methods 124, 1 (Nov. 13, 1989).
31. Miho Masuoka et. al J Clin Invest. 2012; doi: 10.1172/JC158978
32. Asano. K et al. Nature Genetics 41. 1325-1329 (2009)
33. Proc Natl Acad Sci USA. 2012 Mar. 27; 109(13): 5010-5 Epub 2012 Mar. 7.
34. Wong C K, et al. PloS One. 2012: 7. Epub 2012 Jan. 17.
35. Nakajima S, et al. J Allergy Clin Immunol. 2012; 129. Epub 2012 Mar. 3.
36. Otsuka A, et al. PLoS One. 2011; 6. Epub 2011 Sep. 30.
37. Rakoff-Nahoum S et al, Cell, 2004; 118: 229-241.
38. Freitag T L et al, Gut, 2009; 58:1597-1605., Ohta N et al, J Immunol, 2002; 169: 460-468.
39. DePaolo R W et al, Nature, 2011; 471: 220-224
40. Freitag T L, et al, Gut, 200958: 1597-1605
41. Denning T L et al. Nat Immunol, 2007; 8: 1086-1094.
42. Wang X et al, Nucleic Acids Research, 2003; 31: e154
43. Maiuri L et al, Lancet, 2003; 362:30-37., Karen E et al, J. Immunol. 2006; 176; 2512-2521.
44. Karen E et al, J. Immunol. 2006; 176; 2512-2521.
45. Weber B et al, Semin Immunopathol, 2009; 31: 171-184., Serbina N V et al, Annu Rev Immunol. 2008; 26: 421-452.
46. Okoshi Y et al, Int Immunol. 2005; 17: 65-72.
47. Reinke Y et al, Exp Cell Res, 2011 in press.
48. Barone M V et al, PLoS ONE, 2010; 5: e12246.
49. Barone M V et al, PLoS ONE 2011; 62: e17039.

---

The invention claimed is:

1. A method of treatment or prophylaxis of an allergic disease, the method comprising:
administering an effective amount of an activity modulator for suppressing inhibitory signal transduction of a CD300a-expressing myeloid cell to a human, said activity modulator comprising a substance that inhibits binding of CD300a to phosphatidyl serine, which substance is an anti-human CD300a antibody comprising:
an H-chain variable region having the amino acid sequence of SEQ ID NO:3 or an amino acid sequence that is the same as the amino acid sequence of SEQ ID NO:3 except that 1, 2, 3, 4, or 5 amino acid(s) is/are substituted in one or more regions other than in a complementarity determining region; and
an L-chain variable region having the amino acid sequence of SEQ ID NO:4 or an amino acid sequence that is the same as the amino acid sequence of SEQ ID NO:4 except that 1, 2, 3, 4, or 5 amino acid(s) is/are substituted in one or more regions other than in a complementarity determining region.

2. The method according to claim 1, wherein said allergic disease is atopic dermatitis or asthma.

3. A method of treatment of an allergic disease, the method comprising:
administering an effective amount of an activity modulator for suppressing inhibitory signal transduction of a CD300a-expressing myeloid cell to a human, said activity modulator comprising an anti-human CD300a antibody comprising
an H-chain variable region having the amino acid sequence of SEQ ID NO:3; and
an L-chain variable region having the amino acid sequence of SEQ ID NO:4.

4. The method according to claim 3, wherein said allergic disease is atopic dermatitis or asthma.

* * * * *